United States Patent
Bain et al.

(10) Patent No.: US 10,632,104 B2
(45) Date of Patent: Apr. 28, 2020

(54) AUTOTAXIN INHIBITORS AND USES THEREOF

(71) Applicant: Sabre Therapeutics LLC, South San Francisco, CA (US)

(72) Inventors: Gretchen Bain, San Diego, CA (US); Jillian Frances Evans, San Diego, CA (US); John Howard Hutchinson, San Diego, CA (US); David Lonergan, San Marcos, CA (US)

(73) Assignee: SABRE THERAPEUTICS LLC, South San Francisco, CA (US)

( * ) Notice: Subject to any disclaimer, the term of this patent is extended or adjusted under 35 U.S.C. 154(b) by 11 days.

(21) Appl. No.: 15/574,769

(22) PCT Filed: May 24, 2016

(86) PCT No.: PCT/US2016/033933
§ 371 (c)(1),
(2) Date: Apr. 19, 2018

(87) PCT Pub. No.: WO2016/191427
PCT Pub. Date: Dec. 1, 2016

(65) Prior Publication Data
US 2018/0147185 A1 May 31, 2018

Related U.S. Application Data

(60) Provisional application No. 62/167,216, filed on May 27, 2015.

(51) Int. Cl.
*A61K 31/415* (2006.01)
*A61K 31/44* (2006.01)
(Continued)

(52) U.S. Cl.
CPC ........ *A61K 31/4155* (2013.01); *A61K 9/0014* (2013.01); *A61K 9/0019* (2013.01);
(Continued)

(58) Field of Classification Search
CPC .............. A61K 31/4155; A61K 31/404; A61K 31/4439; A61K 31/4418
(Continued)

(56) References Cited

U.S. PATENT DOCUMENTS 5,186,522 A 2/1993 Spencer
5,210,574 A 5/1993 Kita
(Continued)

FOREIGN PATENT DOCUMENTS

CL 2016001118 A1 12/2016
CL 2016001079 A1 1/2017
(Continued)

OTHER PUBLICATIONS

Albers et al. Boronic acid-based inhibitor of autotaxin reveals rapid turnover of LPA in the circulation. PNAS USA 107:7257-7262 (2010).
(Continued)

*Primary Examiner* — Shengjun Wang
(74) *Attorney, Agent, or Firm* — Wilson Sonsini Goodrich & Rosati

(57) ABSTRACT

Described herein are methods and compositions for the treatment of conditions, diseases, or disorders associated with autotaxin activity. The methods and compositions disclosed herein include the use of at least one autotaxin inhibitor compound.

9 Claims, 4 Drawing Sheets

****p<0.0001 comparison to Bleo
One-Way ANOVA (Dunnett's test)

(51) Int. Cl.

| | | |
|---|---|---|
| *A61K 31/4155* | (2006.01) | |
| *A61P 7/06* | (2006.01) | |
| *A61P 19/04* | (2006.01) | |
| *A61P 27/02* | (2006.01) | |
| *A61P 17/06* | (2006.01) | |
| *A61P 21/04* | (2006.01) | |
| *A61P 9/10* | (2006.01) | |
| *A61P 25/28* | (2006.01) | |
| *A61P 1/16* | (2006.01) | |
| *A61P 11/06* | (2006.01) | |
| *A61P 3/04* | (2006.01) | |
| *A61P 15/02* | (2006.01) | |
| *A61P 17/00* | (2006.01) | |
| *A61P 19/02* | (2006.01) | |
| *A61P 9/12* | (2006.01) | |
| *A61P 13/10* | (2006.01) | |
| *A61P 1/00* | (2006.01) | |
| *A61P 5/00* | (2006.01) | |
| *A61P 11/00* | (2006.01) | |
| *A61P 25/00* | (2006.01) | |
| *A61P 29/00* | (2006.01) | |
| *A61P 17/04* | (2006.01) | |
| *A61P 35/00* | (2006.01) | |
| *A61K 9/00* | (2006.01) | |
| *A61K 9/08* | (2006.01) | |
| *A61K 9/20* | (2006.01) | |
| *A61K 9/48* | (2006.01) | |
| *A61K 31/4439* | (2006.01) | |

(52) U.S. Cl.
CPC .............. *A61K 9/0053* (2013.01); *A61K 9/08* (2013.01); *A61K 9/20* (2013.01); *A61K 9/48* (2013.01); *A61K 31/4439* (2013.01); *A61P 1/00* (2018.01); *A61P 1/16* (2018.01); *A61P 3/04* (2018.01); *A61P 5/00* (2018.01); *A61P 7/06* (2018.01); *A61P 9/10* (2018.01); *A61P 9/12* (2018.01); *A61P 11/00* (2018.01); *A61P 11/06* (2018.01); *A61P 13/10* (2018.01); *A61P 15/02* (2018.01); *A61P 17/00* (2018.01); *A61P 17/04* (2018.01); *A61P 17/06* (2018.01); *A61P 19/02* (2018.01); *A61P 19/04* (2018.01); *A61P 21/04* (2018.01); *A61P 25/00* (2018.01); *A61P 25/28* (2018.01); *A61P 27/02* (2018.01); *A61P 29/00* (2018.01); *A61P 35/00* (2018.01)

(58) Field of Classification Search
USPC ........................................ 514/406, 341, 337
See application file for complete search history.

(56) References Cited

U.S. PATENT DOCUMENTS

| | | |
|---|---|---|
| 5,538,444 A | 7/1996 | Strand et al. |
| 5,564,676 A | 10/1996 | Goloff et al. |
| 5,564,949 A | 10/1996 | Wellinsky |
| 5,711,925 A | 1/1998 | Noda et al. |
| 5,761,473 A | 6/1998 | Kahle et al. |
| 6,143,757 A | 11/2000 | Daugan et al. |
| 6,890,933 B1 | 5/2005 | Feng et al. |
| 7,060,697 B2 | 6/2006 | Marsilje et al. |
| 7,839,888 B2 | 11/2010 | Jung et al. |
| 7,905,958 B2 | 3/2011 | Sasaki et al. |
| 7,921,385 B2 | 4/2011 | Abrams et al. |
| 8,022,239 B2 | 9/2011 | Parrill-Baker et al. |
| 8,268,891 B1 | 9/2012 | Parrill-Baker et al. |
| 8,329,907 B2 | 12/2012 | Schultz et al. |
| 8,343,934 B2 | 1/2013 | Parrill-Baker et al. |
| 8,378,100 B2 | 2/2013 | Lynch et al. |
| 8,497,371 B2 | 7/2013 | Parrill-Baker et al. |
| 8,530,650 B2 | 9/2013 | Schiemann et al. |
| 8,552,001 B2 | 10/2013 | Schiemann et al. |
| 8,557,824 B2 | 10/2013 | Schiemann et al. |
| 8,673,882 B2 | 3/2014 | Gupte et al. |
| 9,000,025 B2 | 4/2015 | Roppe et al. |
| 9,051,320 B1 * | 6/2015 | Evans ................. A61K 31/405 |
| 9,334,261 B2 * | 5/2016 | Hutchinson ............ A61K 45/06 |
| 9,468,628 B2 * | 10/2016 | Hutchinson ............ A61K 45/06 |
| 9,999,615 B2 * | 6/2018 | Hutchinson ............ A61K 45/06 |
| 2005/0004156 A1 | 1/2005 | Feng et al. |
| 2005/0267108 A1 | 12/2005 | Hsieh et al. |
| 2006/0270634 A1 | 11/2006 | Miller et al. |
| 2010/0016258 A1 | 1/2010 | Lynch et al. |
| 2010/0136650 A1 | 6/2010 | Parrill-Baker et al. |
| 2010/0222341 A1 | 9/2010 | Schiemann et al. |
| 2010/0240676 A1 | 9/2010 | Schiemann et al. |
| 2010/0249132 A1 | 9/2010 | Schultz et al. |
| 2010/0267037 A1 | 10/2010 | Westbrook et al. |
| 2011/0110886 A1 | 5/2011 | Braddock |
| 2011/0160148 A1 | 6/2011 | Parrill-Baker et al. |
| 2011/0230471 A1 | 9/2011 | Staehle et al. |
| 2011/0237583 A1 | 9/2011 | Schiemann et al. |
| 2012/0015959 A1 | 1/2012 | Staehle et al. |
| 2012/0015976 A1 | 1/2012 | Schultz et al. |
| 2012/0059016 A1 | 3/2012 | Schiemann et al. |
| 2012/0100592 A1 | 4/2012 | Parrill-Baker et al. |
| 2012/0115852 A1 | 5/2012 | Schultz et al. |
| 2012/0190650 A1 | 7/2012 | Gupte et al. |
| 2012/0202827 A1 | 8/2012 | Schiemann et al. |
| 2012/0316162 A1 | 12/2012 | Schiemann et al. |
| 2013/0012505 A1 | 1/2013 | Staehle et al. |
| 2013/0023556 A1 | 1/2013 | Schultz et al. |
| 2013/0029948 A1 | 1/2013 | Roppe et al. |
| 2013/0150326 A1 | 6/2013 | Roppe et al. |
| 2013/0229948 A1 | 9/2013 | Stewart |
| 2013/0251728 A1 | 9/2013 | Harp et al. |
| 2013/0270634 A1 | 10/2013 | Huang et al. |
| 2014/0086839 A1 | 3/2014 | Achiron et al. |
| 2014/0113953 A1 | 4/2014 | Stoffel et al. |
| 2014/0171361 A1 | 6/2014 | Jonker et al. |
| 2014/0171403 A1 | 6/2014 | Legrand et al. |
| 2014/0171404 A1 | 6/2014 | Furminger et al. |
| 2014/0200231 A1 | 7/2014 | Beauchamp et al. |
| 2016/0264575 A1 | 9/2016 | Hutchinson et al. |
| 2016/0374991 A1 | 12/2016 | Hutchinson et al. |

FOREIGN PATENT DOCUMENTS

| | | |
|---|---|---|
| CL | 2016001080 A1 | 1/2017 |
| CN | 1095841 C | 12/2002 |
| JP | 2013129632 A | 7/2013 |
| WO | WO-0130343 A1 | 5/2001 |
| WO | WO-0228865 A2 | 4/2002 |
| WO | WO-02083126 A1 | 10/2002 |
| WO | WO-03029212 A1 | 4/2003 |
| WO | WO-2004019869 A2 | 3/2004 |
| WO | WO-2004020408 A1 | 3/2004 |
| WO | WO-2004020409 A1 | 3/2004 |
| WO | WO-2005061455 A1 | 7/2005 |
| WO | WO-2006041961 A1 | 4/2006 |
| WO | WO-2006050236 A2 | 5/2006 |
| WO | WO-2006134499 A2 | 12/2006 |
| WO | WO-2007134169 A2 | 11/2007 |
| WO | WO-2008157361 A1 | 12/2008 |
| WO | WO-2009046804 A1 | 4/2009 |
| WO | WO-2009046841 A1 | 4/2009 |
| WO | WO-2009046842 A2 | 4/2009 |
| WO | WO-2009151644 A2 | 12/2009 |
| WO | WO-2010040080 A1 | 4/2010 |
| WO | WO-2010060532 A1 | 6/2010 |
| WO | WO-2010063352 A1 | 6/2010 |
| WO | WO-2010112116 A1 | 10/2010 |
| WO | WO-2010112124 A1 | 10/2010 |
| WO | WO-2010115491 A1 | 10/2010 |
| WO | WO-2010132479 A2 | 11/2010 |
| WO | WO-2011002918 A1 | 1/2011 |
| WO | WO-2011006569 A1 | 1/2011 |
| WO | WO2011/049433 A1 * | 4/2011 |
| WO | WO-2011044978 A1 | 4/2011 |

(56) References Cited

FOREIGN PATENT DOCUMENTS

| | | |
|---|---|---|
| WO | WO-2011053597 A1 | 5/2011 |
| WO | WO-2011103430 A1 | 8/2011 |
| WO | WO-2011116867 A1 | 9/2011 |
| WO | WO-2012024620 A2 | 2/2012 |
| WO | WO-2012100018 A1 | 7/2012 |
| WO | WO-2012112964 A2 | 8/2012 |
| WO | WO-2012112966 A1 | 8/2012 |
| WO | WO-2012166415 A1 | 12/2012 |
| WO | WO-2013054185 A1 | 4/2013 |
| WO | WO-2013061297 A1 | 5/2013 |
| WO | WO-2013186159 A1 | 12/2013 |
| WO | WO-2014031170 A1 | 2/2014 |
| WO | WO-2014048865 A1 | 4/2014 |
| WO | WO-2014097151 A2 | 6/2014 |
| WO | WO-2015042052 A1 | 3/2015 |
| WO | WO-2015042053 A1 | 3/2015 |
| WO | WO-2015048301 A1 | 4/2015 |
| WO | WO-2015077502 A1 | 5/2015 |
| WO | WO-2015077503 A1 | 5/2015 |
| WO | WO-2016191427 A1 | 12/2016 |

OTHER PUBLICATIONS

Albers et al. Chemical evolution of autotaxin inhibitors. Chem. Rev. 112:2593-2603 (2012).

Albers et al. Discovery and optimization of boronic acid based inhibitors of autotaxin. J. Med. Chem. 53:4958-4967 (2010).

Albers et al. Structure-based design of novel boronic acid-based inhibitors of autotaxin. J. Med. Chem. 54:4619-4626 (2011).

Aljammal et al. Serum Autotaxin Correlates with Insulin Resistance and Features of the Metolic syndrom in Humans. Poster and Abstract (3 pgs.) (Jun. 2014).

American Diabetes Association. Diagnosis and Classification of Diabetes Mellitus. Diabetes Care 37(Supp. 1):S81-S90 (2014).

American Diabetes Association. Standards of Medical care in Diabetes—2014. Diabetes Care 37(Supp. 1):S14 (2014).

Antunes et al. In silico prediction of novel phosphodiesterase type-5 inhibitors derived from Sildenafil, Vardenafil and Tadalafil. Bioorganic & Medicinal Chemistry 16:7599-7606 (2008).

Baker et al. Carba analogs of cyclic phosphatidic acid are selective inhibitors of autotaxin and cancer cell invasion and metastasis. J. Biol. Chem. 281:22786-22793 (2006).

Barbayianni et al. Autotaxin inhibitors: a patent review. Expert Opin Ther Pat. 23(9):1123-1132 (2013).

Bosarge et al. Stress-induced Hyperglycemia. Is It Harmful Following Trama? Advances in Surgery 47:287-297 (2013).

Boucher et al. Potential involvement of adipocyte insulin resistance in obesity-associated upregulation of adipocyte lysophospholipase D/autotaxin expression. Diabetologia 48:569-577 (2005).

Cui et al. alpha- and beta-substituted phosphonate analogs of LPA as autotaxin inhibitors. Bioorg. Med. Chem. 16:2212-2225 (2008).

Cui et al. Synthesis and biological evaluation of phosphonate derivatives as autotaxin (ATX) inhibitors. Bioorg. Med. Chem. Lett. 17:1634-1640 (2007).

Daugan et al. The Discovery of Tadalafil: A Novel and Highly Selective PDE5 Inhibitor. 2: 2,3,6,7,12,12a-hexahydropyrazino[1',2':1,6]pyrido[3,4-b]indole-1,4-dione Analogues. J Med Chem 46:4525-4532 (2003).

Durgam et al. Synthesis and pharmacological evaluation of second-generation phosphatidic acid derivatives as lysophosphatidic acid receptor ligands. Bioorg. Med. Chem. Lett. 16:633-640 (2006).

Durgam et al. Synthesis, structure-activity relationships, and biological evaluation of fatty alcohol phosphates as lysophosphatidic acid receptor ligands, activators of PPARgamma, and inhibitors of autotaxin. J. Med. Chem. 48:4919-4930 (2005).

Dusaulcy et al. Adipose-specific disruption of autotaxin enhances nutritional fattening and reduces plasma lysophosphatidic acid. J of Lipid Research. 52:1247-1255 (2011).

East et al. Synthesis and structure-activity relationships of tyrosine-based inhibitors of autotaxin (ATX). Bioorg. Med. Chem. Lett. 20:7132-7136 (2010).

Federico et al. Autotaxin and its product lysophosphatidic acid suppress brown adipose differentiation and promote diet-induced obesity in mice. Mol. Endocr. 26:786-797 (2012).

Federico et al. Therapeutic potential of autotaxin/lysophospholipase d inhibitors. Curr Drug Targets 9(8):698-708 (2008).

Ferry et al. S32826, A Nanomolar Inhibitor of Autotaxin: Discovery, Synthesis and Applications as a Pharmacological Tool. J. Pharmacol. Exp. Ther. 327:809-819 (2008).

Gajewak et al. Synthesis, pharmacology, and cell biology of sn-2-aminooxy analogues of lysophosphatidic acid. Org. Lett. 10:1111-1114 (2008).

Gendaszewska-Darmach et al. The chemical synthesis of metabolically stabilized 2-OMe-LPA analogues and preliminary studies of their inhibitory activity toward autotaxin. Bioorg. Med. Chem. Lett. 22:2698-2700 (2012).

Gierse et al. A novel autotaxin inhibitor reduces lysophosphatidic acid levels in plasma and the site of inflammation. J. Pharmacol. Exp. 334:310-317 (2010).

Gududuru et al. Identification of Darmstoff analogs as selective agonists and antagonists of lysophosphatidic acid receptors. Bioorg. Med. Chem. Lett. 16:451-456 (2006).

Gupte et al. Benzyl and naphthalene methylphosphonic acid inhibitors of autotaxin with anti-invasive and anti-metastatic activity. ChemMedChem 6:922-935 (2011).

Gupte et al. Synthesis and pharmacological evaluation of the stereoisomers of 3-carba cyclic-phosphatidic acid. Bioorg. Med. Chem. Lett. 20:7525-7528 (2010).

Higazi et al. Immunomodulatory effects of plasminogen activators on hepatic fibrogenesis. Clin Exp Immunol 152(1):163-173 (2008).

Hoeglund et al. Characterization of non-lipid autotaxin inhibitors. Bioorg. Med. Chem. 18:769-776 (2010).

Hoeglund et al. Optimization of a pipemidic acid autotaxin inhibitor. J. Med. Chem. 53:1056-1066 (2010).

Humphrey et al. Practical methodologies for the synthesis of indoles. Chem Rev. 106(7):2875-2911 (2006).

Jiang et al. Alpha-substituted phosphonate analogues of lysophosphatidic acid (LPA) selectively inhibit production and action of LPA. ChemMedChem 2:679-690 (2007).

Jiang et al. Aromatic phosphonates inhibit the lysophospholipase D activity of autotaxin. Bioorg. Med. Chem. Lett. 21:5098-5101 (2011).

Kano et al. LPA and its analogs—attractive tools for elucidation of LPA biology and drug development. Curr. Med. Chem. 15:2122-2131 (2008).

Klein et al. Solid-phase synthesis of new fused tetra, penta and hexacyclic β-carboline derivatives. Tetrahedron Letters 44:2211-2215 (2003).

Moulharat et al. Molecular pharmacology of adipocyte-secreted autotaxin. Chem.-Biol. Interact. 172:115-124 (2008).

Nishimura et al. ENPP2 contributes to adipose tissue expansion in diet-induced obesity. Diabetes. 2014. Epub ahead of print. Published online Jun. 26, 2014. doi: 10.2337/db13-1694. 45 pages.

North et al. Pharmacophore development and application toward the identification of novel, small-molecule autotaxin inhibitors. J. Med. Chem. 53:3095-3105 (2010).

Parrill et al. Autotaxin Inhibitors: A Perspective on Initial Medicinal Chemistry Efforts. Expert Opin Ther Pat 20(12):1619-1625 (2010).

Parrill et al. Virtual screening approaches for the identification of non-lipid autotaxin inhibitors. Bioorg. Med. Chem. 16:1784-1795 (2008).

PCT/US2014/066705 International Preliminary Report on Patentability dated Jun. 2, 2016.

PCT/US2014/066705 International Search Report and Written Opinion dated Mar. 9, 2015.

PCT/US2014/066706 International Preliminary Report on Patentability dated Jun. 2, 2016.

PCT/US2014/066706 International Search Report and Written Opinion dated Mar. 13, 2015.

PCT/US2016/33933 International Preliminary Report on Patentability dated Dec. 7, 2017.

(56) References Cited

OTHER PUBLICATIONS

PCT/US2016/33933 International Search Report and Written Opinion dated Aug. 25, 2016.

Rancoule et al. Depot-specific regulation of autotaxin with obesity in human adipose tissue. J Physiol Biochem.68:635-644 (2012).

Rancoule et al. Lysophosphatidic acid impairs glucose homeostasis and inhibits insulin secretion in high-fat diet obese mice. Diabetolgia (9 pgs) (2013).

Rehman et al. Drug-Induced Glucose Alterations Part 2: Drug-Induced Hyperglycemia. Diabetes Spectrum 24(4):234-238 (2011).

Saunders et al. Identification of small-molecule inhibitors of autotaxin that inhibit melanoma cell migration and invasion. Mol. Cancer Ther. 7:3352-3362 (2008).

Skyler. Effects of Glycemic Control on Diabetes Complications and on the Prevention of Diabetes. Clinical Diabetes 22(4):162-166 (2004).

Tanaka et al. Efficient synthesis of 3-O-thia-cPA and preliminary analysis of its biological activity toward autotaxin. Bioorg. Med. Chem. Lett. 21:4180-4182 (2011).

Turner et al. Glycemic Control With Diet, Sulfonylurea, Metformin, or Insulin in Patients With Type 2 Diabetes Mellitus: Progressive Requirement for Multiple Therapies (UUKPDS 49). JAMA 281(21):2005-2012 (1999).

Van Meeteren et al. Anticancer activity of FTY720: phosphorylated FTY720 inhibits autotaxin, a metastasis-enhancing and angiogenic lysophospholipase D. Cancer Lett. 266:203-208 (2008).

Van Meeteren et al. Inhibition of autotaxin by lysophosphatidic acid and sphingosine 1-phosphate. J. Biol. Chem. 280:21155-21161 (2005).

Widder et al. Section III: Prodrugs Kinetics. Method in Enzymology. 112:309-396 (1985).

Yamamoto et al. Animal Model of Sclerotic Skin. I: Local Injections of Bleomycin Induce Sclerotic Skin Mimicking Scleroderma. J Invest Dermatol 112(4):456-462 (1999).

Zhang et al. Dual activity lysophosphatidic acid receptor pan-antagonist/autotaxin inhibitor reduces breast cancer cell migration in vitro and causes tumor regression in vivo. Cancer Res 69:5441-5449 (2009).

Zou et al. Use of pioglitazone in the treatment of diabetes: effect on cardiovascular risk. Vasc. Health and Risk Management 9:429-433 (2013).

* cited by examiner

****p<0.0001 comparison to Bleo
One-Way ANOVA (Dunnett's test)

AUTOTAXIN INHIBITORS AND USES THEREOF

RELATED APPLICATIONS

This application is filed pursuant to 35 U.S.C. § 371 as a United States National Phase Application of International Application No. PCT/US2016/033933 entitled "AUTOTAXIN INHIBITORS AND USES THEREOF" filed May 24, 2016, which claims the benefit of U.S. Provisional Patent Application No. 62/167,216 filed on May 27, 2015, each of which is herein incorporated by reference in its entirety.

FIELD OF THE INVENTION

Described herein are methods of using autotaxin inhibitors, and pharmaceutical compositions and medicaments thereof, in the treatment of conditions, diseases, or disorders associated with autotaxin activity.

BACKGROUND OF THE INVENTION

Autotaxin (ATX), also known as ectonucleotide pyrophosphatase/phosphodiesterase family member 2 or ENNP2, is an adipocyte secreted lysophospholipase D that catalyzes the formation of the lipid mediator, lysophosphatidic acid (LPA). Autotaxin expression is enhanced in individuals with certain conditions or diseases.

SUMMARY OF THE INVENTION

The autotaxin-lysophosphatidic acid signaling pathway has been implicated in a variety of signaling pathways involved in cell migration, proliferation, and survival. Due to its role in these pathways, autotaxin has been explored as a drug discovery target for the treatment of chronic inflammation, neuropathic pain, fibrotic disease, and various cancers. Intensive efforts have focused on identifying autotaxin inhibitors in the treatment of these disorders.

In one aspect, provided herein are methods of using one or more autotaxin inhibitors for the treatment or prevention of diseases or conditions in which autotaxin and/or LPA participates, is involved in the etiology or pathology of the disease, or is otherwise associated with at least one symptom or complication of the disease. Inhibition of the physiological activity of autotaxin and/or LPA is useful in a variety of diseases or conditions. The autotaxin-LPA signaling pathway has been implicated in fibrotic diseases, colitis, cancer, pruritus, angiogenesis, inflammation, autoimmune diseases, reproduction, neurological diseases, and tumor progression.

In one aspect, the methods described herein involve the use of one or more autotaxin inhibitor compounds for the treatment of diseases or conditions in which autotaxin activity contributes to the symptomology or progression of the disease, disorder or condition. These diseases, disorders, or conditions may arise from one or more of a genetic, iatrogenic, immunological, infectious, metabolic, oncological, toxic, surgical, and/or traumatic etiology. In one aspect, the methods, compounds, pharmaceutical compositions, and medicaments described herein comprise autotaxin inhibitors.

In one aspect, the autotaxin inhibitors are useful for the treatment of diseases or conditions such as, but not limited to, fibrosis, colitis, cell proliferative disease, inflammatory disease, autoimmune diseases, reproductive diseases, abnormal angiogenesis-associated disease, scleroderma, brain or heart reperfusion injury, neurodegenerative disease, neuropathic pain, peripheral neuropathy, ocular disease, diabetic retinopathy, proliferative vitreoretinopathy, cicatricial pemphigoid, metabolic disorder, and glaucoma.

In one aspect, provided herein are pharmaceutical compositions comprising one or more autotaxin inhibitors, pharmaceutically acceptable salts, or solvates thereof useful for the treatment or prevention of one or more diseases or conditions. In some embodiments, the pharmaceutical composition attenuates or reverses one or more signs or symptoms associated with the one or more disease or conditions. In some embodiments, the pharmaceutical composition prevents the onset of one or more complications associated with the one or more diseases or conditions. In some embodiments, the pharmaceutical composition comprises autotaxin inhibitor A. In some embodiments, the pharmaceutical composition comprises autotaxin inhibitor B. In some embodiments, the pharmaceutical composition comprises autotaxin inhibitor C. In some embodiments, the pharmaceutical composition comprises autotaxin inhibitor D. In some embodiments, the pharmaceutical composition comprises autotaxin inhibitor E. In some embodiments, the pharmaceutical composition comprises autotaxin inhibitor F. In some embodiments, the pharmaceutical composition comprises autotaxin inhibitor G. In some embodiments, the pharmaceutical composition comprises autotaxin inhibitor H. In some embodiments, the pharmaceutical composition comprises autotaxin inhibitor I. In some embodiments, the pharmaceutical composition further comprises an additional therapeutic agent. In some embodiments, the pharmaceutical composition is administered in combination with one or more additional treatments for a disease, disorder or condition. In some embodiments, the pharmaceutical composition comprises at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is in the form of a tablet, a pill, a capsule, a liquid, a suspension, a gel, a dispersion, a solution, an emulsion, an ointment, or a lotion.

In one aspect, described herein is a method of treating or preventing any one of the diseases or conditions described herein comprising administering a therapeutically effective amount of an autotaxin inhibitor, or a pharmaceutically acceptable salt, or solvate thereof, to a mammal in need thereof.

In one aspect, described herein is a method of treating or preventing any one of the diseases or conditions described herein comprising administering a therapeutically effective amount of an autotaxin inhibitor, or a pharmaceutically acceptable salt, or solvate thereof, to a mammal in need thereof, wherein the autotaxin inhibitor, or the pharmaceutically acceptable salt or solvate thereof, does not cause hepatobiliary damage in the mammal.

In one aspect, described herein is a method of treating or preventing any one of the diseases or conditions described herein comprising administering a therapeutically effective amount of an autotaxin inhibitor, or a pharmaceutically acceptable salt, or solvate thereof, to a mammal in need thereof; wherein one or more liver proteins are not significantly elevated in the subject after the administration of the autotaxin inhibitor, or the pharmaceutically acceptable salt or solvate thereof. In some embodiments, a significant elevation in the concentration of a liver protein is at least a 50%, 100%, 200% or 500% increase in the concentration of the liver protein. In some embodiments, the liver protein is aspartate transaminase. In some embodiments, the liver protein is alkaline phosphatase. In some embodiments, the liver protein is bilirubin.

In another aspect, described herein is a method for treating or preventing fibrosis, pruritus, colitis, cancer, an inflammatory disease or condition, an airway disease or condition, an autoimmune disease or condition, a neurological disease or condition, obesity, intraocular pressure, neuropathic pain, or combinations thereof in a mammal comprising administering a therapeutically effective amount of an autotaxin inhibitor, or a pharmaceutically acceptable salt, or solvate thereof, to the mammal. In some embodiments, the administration of an autotaxin inhibitor, or a pharmaceutically acceptable salt, or solvate thereof attenuates at least one symptom of fibrosis, pruritus, colitis, cancer, an inflammatory disease or condition, an airway disease or condition, an autoimmune disease or condition, neurological disease or condition, obesity, intraocular pressure, neuropathic pain, or combinations thereof.

In one aspect, described herein is a method for treating or preventing a disease, disorder or condition described herein, the method comprising administering an autotaxin inhibitor to a mammal in need thereof; wherein following the administration of the autotaxin inhibitor, blood lysophosphatidic acid levels in the mammal decrease by at least about 5%, 10%, 20%, 30%, 40% or 50%.

In one aspect, described herein is a method for treating or preventing a disease, disorder or condition described herein, the method comprising administering an autotaxin inhibitor to a mammal in need thereof; wherein following the administration of the autotaxin inhibitor, blood autotaxin levels in the mammal decrease by at least about 5%, 10%, 20%, 30%, 40% or 50%.

In one aspect, described herein is a method for treating or preventing a disease, disorder or condition described herein, the method comprising administering an autotaxin inhibitor, or a pharmaceutically acceptable salt or solvate thereof, wherein the autotaxin inhibitor is formulated for administration to a mammal in need thereof by intravenous administration, subcutaneous administration, oral administration, inhalation, nasal administration, dermal administration, or ophthalmic administration.

In one aspect, described herein is a method for treating or preventing a disease, disorder or condition described herein, the method comprising administering an autotaxin inhibitor, or a pharmaceutically acceptable salt or solvate thereof, wherein the autotaxin inhibitor is in a pharmaceutical composition having the form of a tablet, a pill, a capsule, a liquid, a suspension, a gel, a dispersion, a solution, an emulsion, an ointment, or a lotion.

In one aspect, described herein is a method for the treatment or prevention of fibrosis in a mammal comprising administering a therapeutically effective amount of an autotaxin inhibitor, or a pharmaceutically acceptable salt, or solvate thereof, to the mammal. In some embodiments, accumulation of extracellular matrix or the rate of accumulation of extracellular matrix in a tissue having fibrosis is reduced following administration of the autotaxin inhibitor, or a pharmaceutically acceptable salt, or solvate thereof. In some embodiments, the fibrosis comprises peritoneal fibrosis, lung fibrosis, liver fibrosis, kidney fibrosis, ocular fibrosis or cutaneous fibrosis. As an example, the method comprises administering an autotaxin inhibitor to a mammal having liver fibrosis. In some instances, the onset of cirrhosis or liver failure is delayed or prevented following administration of the autotaxin inhibitor, or a pharmaceutically acceptable salt, or solvate thereof. In some instances, the accumulation of fibrogenic cells and/or the deposition of extracellular matrix proteins within the liver is attenuated or prevented following administration of the autotaxin inhibitor, or a pharmaceutically acceptable salt, or solvate thereof. In one example, the method comprises administering an autotaxin inhibitor to a mammal having kidney fibrosis. In some instances, administration of an autotaxin inhibitor to the mammal prevents renal failure. As another example, the method comprises administering an autotaxin inhibitor to a mammal having peritoneal fibrosis. As a further example, the method comprises administering an autotaxin inhibitor to a mammal having skin fibrosis. In some instances, dermal thickness of a skin sample having fibrosis is decreased by at least about 10%, 20%, 30%, 40%, 50%, 60%, 70%, 80% or 90% following administration of the autotaxin inhibitor, or a pharmaceutically acceptable salt, or solvate thereof.

In one aspect, described herein is a method for the treatment or prevention of fibrosis in a mammal comprising administering to the mammal a therapeutically effective amount of an autotaxin inhibitor, or a pharmaceutically acceptable salt, or solvate thereof and a second therapeutic agent. In some embodiments, the second therapeutic agent comprises an angiotensin inhibitor, colchicine, corticosteroid, an endothelin inhibitor, interferon-alpha, interleukin 10, an antioxidant, a hepatic stellate cell (HSC) inhibitor, an ACE inhibitor, an ADAM inhibitor, a metalloenzyme, pirfenidone, tranilast, fluorofenidone, an anti-inflammatory agent, an immunosuppressant, or a combination thereof.

In one aspect, described herein is a method for the treatment or prevention of colitis in a mammal comprising administering a therapeutically effective amount of an autotaxin inhibitor, or a pharmaceutically acceptable salt, or solvate thereof, to the mammal. In one aspect, described herein is a method for the treatment or prevention of inflammatory bowel disease in a mammal comprising administering a therapeutically effective amount of an autotaxin inhibitor, or a pharmaceutically acceptable salt, or solvate thereof, to the mammal. In some instances, the colitis is acute colitis. In some instances, the colitis is chronic colitis. In some embodiments, the colitis is autoimmune colitis, idiopathic colitis, Iatrogenic colitis, vascular disease or infectious colitis.

In one aspect, described herein is a method for the treatment or prevention of ulcerative colitis in a mammal comprising administering a therapeutically effective amount of an autotaxin inhibitor, or a pharmaceutically acceptable salt, or solvate thereof, to the mammal. In some embodiments, administration of the autotaxin inhibitor, or a pharmaceutically acceptable salt, or solvate thereof, reduces ulcer size in ulcerative colitis by at least about 10%, 20%, 30%, 40%, 50%, 60%, 70%, 80% or 90% following the administration.

In some embodiments, one or more signs or symptoms of colitis are reduced in the mammal following administration of the autotaxin inhibitor. Signs or symptoms include, without limitation, abdominal pain, diarrhea, mucus in stool, cramping, abdominal tenderness, fever, bloody stool, distension, colonic mucosal erythema and ulcers.

In one aspect, described herein is a method for the treatment or prevention of colitis in a mammal comprising administering to the mammal a therapeutically effective amount of an autotaxin inhibitor, or a pharmaceutically acceptable salt, or solvate thereof and a second therapeutic agent. In some embodiments, the second therapeutic agent comprises a steroid, an anti-inflammatory agent, an immunosuppressant, or a combination thereof. In one aspect, provided herein is a method for the treatment or prevention of colitis in a mammal, the method comprising the administration of an autotaxin inhibitor and cyclosporine A. In one aspect, provided herein is a method for the treatment or prevention of colitis in a mammal, the method comprising the administration of an autotaxin inhibitor and sulfasalazine.

In one aspect, described herein is a method for the treatment or prevention of a neurological disease or disorder in a mammal comprising administering a therapeutically effective amount of an autotaxin inhibitor, or a pharmaceutically acceptable salt, or solvate thereof, to the mammal. In one aspect, described herein is a method for the treatment or prevention of multiple sclerosis in a mammal comprising administering a therapeutically effective amount of an autotaxin inhibitor, or a pharmaceutically acceptable salt, or solvate thereof, to the mammal. In some embodiments, administration of the autotaxin inhibitor, or a pharmaceutically acceptable salt, or solvate thereof, attenuates, reverses, or inhibits demyelination in the mammal. In some embodiments, administration of the autotaxin inhibitor, or a pharmaceutically acceptable salt, or solvate thereof to a mammal having multiple sclerosis, decreases the frequency, severity and/or duration of a relapse of multiple sclerosis symptoms in the mammal. Multiple sclerosis symptoms include, without limitation, numbness or weakness in a limb, partial or complete loss of vision, double vision, blurring of vision, tingling sensation, tremors, lack of coordination, unsteady gait, slurred speech, fatigue and dizziness.

In one aspect, described herein is a method for the treatment or prevention of a neurological disease in a mammal, the method comprising administering to the mammal a therapeutically effective amount of an autotaxin inhibitor, or a pharmaceutically acceptable salt, or solvate thereof and a second therapeutic agent. In some embodiments, the second therapeutic agent comprises a corticosteroid, a beta interferon, glatiramer acetate, dimethyl fumarate, fingolimod, teriflunomide, natalizumab, mitoxantrone, a muscle relaxant, or a combination thereof. In some instances, the neurological disease is multiple sclerosis.

In one aspect, described herein is a method for treating or preventing pruritus in a mammal comprising administering a therapeutically effective amount of an autotaxin inhibitor, or a pharmaceutically acceptable salt, or solvate thereof, to the mammal. In some embodiments, the pruritus is associated with dermatitis herpetiformis, dermatomyositis, pemphigoid, Sjögren's syndrome, Darier's disease, Hailey-Hailey disease, Ichthyoses, Sjögren-Larsson syndrome, dermatophytosis, folliculitis, impetigo and other bacterial infections, insect bites, pediculosis, scabies, viral infection, asteatosis, atopic eczema, contact dermatitis, drug reaction, lichen planus, lichen simplex chronicus, mastocytosis (urticaria pigmentosa), miliaria, psoriasis, scar(s), urticaria, cutaneous T-cell lymphoma or mycosis fungoides, cutaneous B-cell lymphoma, leukemia cutis, pemphigoid gestationis, polymorphic eruption of pregnancy or prurigo gestationis. In one aspect, described herein is a method for treating or preventing cholestatic pruritus in a mammal comprising administering a therapeutically effective amount of an autotaxin inhibitor, or a pharmaceutically acceptable salt, or solvate thereof, to the mammal in need thereof. In some embodiments, following administration of the autotaxin inhibitor, the number of scratch movements exhibited by a mammal having pruritus decreases by at least about 10%, 20%, 30%, 40%, 50%, 60%, 70%, 80%, or 90%. In one aspect, described herein is a method for the treatment or prevention of a pruritus in a mammal, the method comprising administering to the mammal a therapeutically effective amount of an autotaxin inhibitor, or a pharmaceutically acceptable salt, or solvate thereof and a second therapeutic agent. In some embodiments, the second therapeutic agent comprises topical capsaicin.

In one aspect, described herein is a method for treating or preventing cancer in a mammal comprising administering a therapeutically effective amount of an autotaxin inhibitor, or a pharmaceutically acceptable salt, or solvate thereof, to the mammal. In some embodiments, the cancer is a solid tumor. In some embodiments, the cancer is bladder cancer, colon cancer, brain cancer, breast cancer, endometrial cancer, heart cancer, kidney cancer, lung cancer, liver cancer, uterine cancer, blood and lymphatic cancer, ovarian cancer, pancreatic cancer, prostate cancer, thyroid cancer, or skin cancer. In some embodiments, the cancer is a sarcoma, carcinoma, or lymphoma. In some embodiments, the cancer is amenable to treatment with an autotaxin inhibitor. In some embodiments, the method further comprises administering a second therapeutic agent to the mammal in addition to the autotaxin inhibitor, or a pharmaceutically acceptable salt, or solvate thereof. In one aspect, described herein is a method for the treatment or prevention of cancer in a mammal, the method comprising administering to the mammal a therapeutically effective amount of an autotaxin inhibitor, or a pharmaceutically acceptable salt, or solvate thereof and a second anti-cancer agent or therapy.

In one aspect, described herein is a method of reducing or inhibiting angiogenesis in a mammal comprising administering a therapeutically effective amount of an autotaxin inhibitor, or a pharmaceutically acceptable salt, or solvate thereof, to the mammal. In some embodiments, reducing or inhibiting angiogenesis in the mammal treats atherosclerosis, hypertension, tumor growth, inflammation, rheumatoid arthritis, wet-form macular degeneration, choroidal neovascularization, retinal neovascularization, or diabetic retinopathy. In one aspect, described herein is a method for the reduction or inhibition of angiogenesis in a mammal, the method comprising administering to the mammal a therapeutically effective amount of an autotaxin inhibitor, or a pharmaceutically acceptable salt, or solvate thereof and a second therapeutic agent or therapy. In some instances, the second therapeutic agent comprises an angiogenesis inhibitor, for example, a VEGF inhibitor (bevacizumab), sorafenib, sunitinib, pazopanib, everolimus, or a combination thereof.

In another aspect, described herein is a method of treating or preventing an inflammatory disease or condition in a mammal comprising administering a therapeutically effective amount of an autotaxin inhibitor, or a pharmaceutically acceptable salt, or solvate thereof, to the mammal. In some embodiments, the inflammatory disease or condition is psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, lupus erythematosus, dermatomyositis, Sjogren's syndrome, thyroiditis, myasthenia gravis, autoimmune hemolytic anemia, multiple sclerosis, cystic fibrosis, chronic relapsing hepatitis, primary biliary cirrhosis, primary sclerosing cholangitis, allergic conjunctivitis or atopic dermatitis. In one aspect, described herein is a method for treating or preventing an inflammatory disease or condition in a mammal, the method comprising administering to the mammal a therapeutically effective amount of an autotaxin inhibitor, or a pharmaceutically acceptable salt, or solvate thereof and an anti-inflammatory drug. In some embodiments, the anti-inflammatory drug comprises a non-steroidal anti-inflammatory drug.

In another aspect, described herein is a method of treating or preventing an autoimmune disease or condition in a mammal comprising administering a therapeutically effective amount of an autotaxin inhibitor, or a pharmaceutically acceptable salt, or solvate thereof, to the mammal. In one aspect, described herein is a method for treating or preventing an autoimmune disease or condition in a mammal comprising administering to the mammal a therapeutically effective amount of an autotaxin inhibitor, or a pharmaceutically acceptable salt, or solvate thereof and an immunosuppressant. In some embodiments, the immunosuppressant comprises a glucocorticoid, cytostatic, antibody, drug, or a combination thereof.

In another aspect, described herein is a method of treating or preventing an airway disease or condition in a mammal comprising administering a therapeutically effective amount of an autotaxin inhibitor, or a pharmaceutically acceptable salt, or solvate thereof, to the mammal. In some embodiments, the airway disease is chronic obstructive pulmonary disease, cystic fibrosis or asthma.

In another aspect, described herein is a method of treating or preventing intraocular pressure in a mammal comprising administering a therapeutically effective amount of an autotaxin inhibitor, or a pharmaceutically acceptable salt, or solvate thereof, to the mammal. In some embodiments, the intraocular pressure is associated with glaucoma.

In another aspect, described herein is a method of treating or preventing neuropathic pain in a mammal comprising administering a therapeutically effective amount of an autotaxin inhibitor, or a pharmaceutically acceptable salt, or solvate thereof, to the mammal. In some embodiments, the neuropathic pain is the result of a nerve injury.

In one aspect, described herein is a method of treating or preventing a metabolic disorder, and/or one or more conditions associated with a metabolic disorder, the method comprising administering an autotaxin inhibitor to a mammal in need thereof. In another aspect, described herein is a method for preventing or delaying the onset of at least one metabolic disorder in a mammal at risk for developing a metabolic disorder, comprising administering to the mammal an autotaxin inhibitor. In some embodiments, the metabolic disorder is treated by reducing blood glucose levels. In some instances, blood glucose levels decrease in the subject by at least bout 10% following administration of the autotaxin inhibitor. In some embodiments, the metabolic disorder is treated by reducing plasma lysophosphatidic acid levels. In some embodiments, the metabolic disorder is treated by improving insulin sensitivity. In some embodiments, the metabolic disorder is treated by increasing insulin secretion. In some embodiments, the metabolic disorder is treated by improving glucose tolerance. In some embodiments, the metabolic disorder is treated by decreasing adipose tissue expansion. In some embodiments, the metabolic disorder does not induce hypoglycemia. In some embodiments, the metabolic disorder is selected from the group consisting of: metabolic syndrome, elevated blood glucose levels, insulin resistance, glucose intolerance, type 2 diabetes, type 1 diabetes, pre-diabetes, non-alcoholic fatty liver disease (NAFLD), nonalcoholic steatohepatitis (NASH), obesity, or a combination thereof. In some embodiments, the mammal has a body mass index of at least 25 kg/m2 and at least one or more of the diabetes risk factors selected from the group consisting of: physical inactivity, a first-degree relative with diabetes, a high-risk race or ethnicity, a woman that delivered a baby weighing more than 9 pounds, a woman previously diagnosed with gestational diabetes, hypertensive, HDL cholesterol levels lower than at least 0.9 mmol/L (35 mg/dL), triglyceride levels at least 2.82 mmol/L (250 mg/dL) or greater, a woman with polycystic ovarian syndrome, severe obesity, acanthosis nigrican, and cardiovascular disease.

In another aspect, described herein is a method of treating or preventing obesity in a mammal comprising administering a therapeutically effective amount of an autotaxin inhibitor, or a pharmaceutically acceptable salt, or solvate thereof, to the mammal.

In one aspect, described herein is a method for reducing blood glucose levels of a mammal comprising administering to the mammal an autotaxin inhibitor, thereby decreasing the blood glucose levels of the mammal. Further provided is a method for preventing or delaying the onset of an elevated blood glucose level in a mammal at risk for developing an elevated glucose level, the method comprising administering to the mammal an autotaxin inhibitor. In some embodiments, the mammal has an elevated blood glucose level. In certain embodiments, the method comprises measuring the blood glucose level of the mammal. In certain embodiments, the method comprises selecting a mammal having an elevated blood glucose level. The measured blood glucose level is inclusive of fasted blood glucose level, post-prandial blood glucose level, whole blood glucose level and plasma blood glucose level. In some embodiments, the blood glucose level is reduced to below 200 mg/dL, 175 mg/dL, 150 mg/dL, 125 mg/dL, 120 mg/dL, 115 mg/dL, 110 mg/dL, 105 mg/dL, or 100 mg/dL after treatment with an autotaxin inhibitor.

In one aspect, described herein is a method for reducing plasma lysophosphatidic acid levels of a mammal comprising administering to the mammal an autotaxin inhibitor; and thereby decreasing plasma lysophosphatidic acid levels of the mammal. In some embodiments, the mammal has an elevated blood glucose level. In some embodiments the mammal is insulin resistant.

In one aspect, described herein is a method for improving insulin sensitivity, delaying the onset of insulin resistance, and/or increasing insulin secretion in a mammal comprising administering to the mammal an autotaxin inhibitor; and thereby improving insulin resistance in the mammal.

In one aspect, described herein is a method for improving glucose tolerance in a mammal comprising administering to the mammal an autotaxin inhibitor; and thereby improving glucose tolerance.

In one aspect, described herein is a method for decreasing adipose tissue expansion in a mammal comprising administering to the mammal an autotaxin inhibitor; and thereby decreasing adipose tissue expansion in the mammal. In some embodiments, the mammal has an elevated blood glucose level. In some embodiments, the mammal is insulin resistant.

In any of the aforementioned aspects are further embodiments in which the effective amount of the autotaxin inhibitor, or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the autotaxin inhibitor, including further embodiments in which the autotaxin inhibitor is administered once a day to the mammal or the autotaxin inhibitor is administered to the mammal multiple times over the span of one day. In some embodiments, the autotaxin inhibitor is administered on a continuous dosing schedule. In some embodiments, the autotaxin inhibitor is administered on a continuous daily dosing schedule.

In any of the aforementioned aspects involving the treatment of autotaxin dependent diseases or conditions are further embodiments comprising administering at least one additional agent in addition to the administration of an autotaxin inhibitor, or a pharmaceutically acceptable salt thereof. In various embodiments, each agent is administered in any order, including simultaneously.

In any of the embodiments disclosed herein, the mammal is a human.

In some embodiments, autotaxin inhibitors provided herein are administered to a human.

In some embodiments, autotaxin inhibitors provided herein are orally administered.

Articles of manufacture, which include packaging material, an autotaxin inhibitor, or a pharmaceutically acceptable salt thereof, within the packaging material, and a label that indicates that the autotaxin inhibitor or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for inhibiting the activity of autotaxin, or for the treatment, prevention or amelioration of one or more symptoms of a disease or condition that would benefit from inhibition of the activity of autotaxin, are provided.

Other objects, features and advantages of the autotaxin inhibitors, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Autotaxin and LPA

Figure 1:
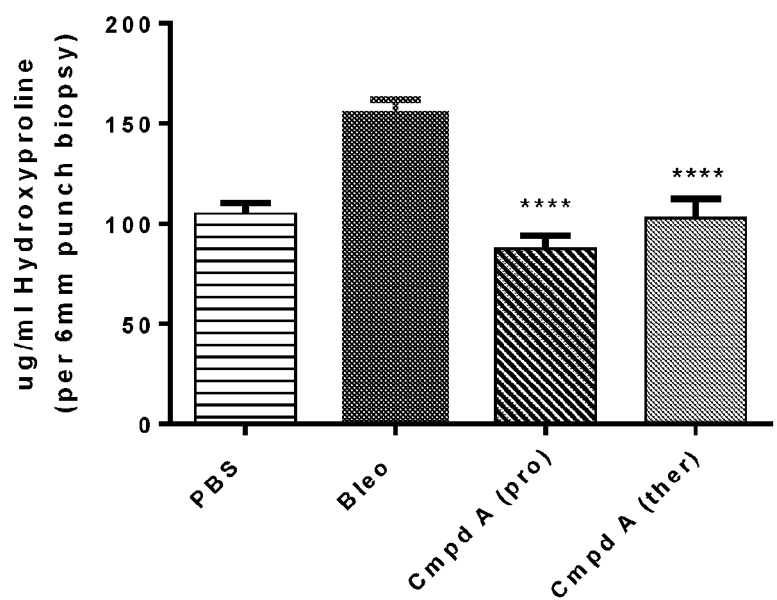
FIG. 1 provides hydroxyproline levels in skin biopsies from PBS-injected or bleomycin-injected mice treated with an autotaxin inhibitor. Cmpd A attenuates skin fibrosis when dosed prophylactically (pro) or therapeutically (ther) in a mouse subcutaneous bleomycin model.

Autotaxin (ATX, NPP2, or ENPP2), an approximately 120 kDa glycoprotein, is a secreted nucleotide pyrophosphatase/phosphodiesterase (NPP) with lysophospholipase D activity that converts extracellular lysophosphatidylcholine (LPC) and other lysophospholipids to lysophosphatidic acid (LPA). Autotaxin is considered to be responsible for the majority of circulating LPA production.

LPA acts through sets of specific G protein-coupled receptors (GPCRs), such as LPA1, LPA2, LPA3, LPA4, LPA5, LPA6, LPA7, LPA8, in an autocrine and paracrine fashion to produce a variety of biological responses. For example, lysophospholipids, such as LPA, are known to affect such biological functions as cellular proliferation, differentiation, survival, migration, adhesion, invasion, and morphogenesis. In addition, LPA is known to play a role in such processes as platelet activation, smooth muscle contraction, actin stress fiber formation, and cell migration.

Autotaxin and LPA have been detected in various biological fluids such as serum, plasma, cerebrospinal fluid, seminal fluid, urine, and saliva, both in animals and humans, suggesting that they are potential biomarkers to predict certain diseases. For example, serum autotaxin concentration and activity is elevated in patients with chronic liver diseases and in pregnant women. As another example, autotaxin activity is increased in cerebrospinal fluid and serum of relapse/remitting multiple sclerosis patients compared to patients with other neurological diseases. In addition, autotaxin is known to be essential for normal development. For example, autotaxin-deficient mice die at embryonic day 9.5 with profound vascular defects in both the yolk sac and the embryo. Furthermore, at embryonic day 8.5, autotaxin-deficient embryos were found to have malformed allantois, neural tube defects, and asymmetric headfolds.

In one aspect, provided herein are methods of using autotaxin inhibitors and pharmaceutical compositions comprising autotaxin inhibitors for the prevention and/or treatment of a condition, disease or disorder associated with autotaxin activity. In some embodiments, the methods disclosed herein comprise the administration of an autotaxin inhibitor to a subject having a disease, condition or disorder described herein. In some embodiments, the methods disclosed herein comprise the administration of an autotaxin inhibitor to a subject suspected of having or developing a disease, condition or disorder described herein.

In one aspect, provided herein are methods for the treatment or prevention of one or more signs, symptoms or complications in a subject resulting from a disease, condition or disorder described herein, the methods comprising administration of an autotaxin inhibitor to the subject.

In one aspect, provided herein are methods for the prevention of a condition, disease or disorder associated with autotaxin activity, the methods comprising administering an autotaxin inhibitor in combination with another preventative therapy.

In one aspect, provided herein are methods for the treatment of a condition, disease or disorder associated with autotaxin activity, the methods comprising administering an autotaxin inhibitor in combination with another treatment.

In one aspect, provided herein are methods for the attenuation, reversal and/or inhibition of a sign, symptom or complication of a condition, disease or disorder associated with autotaxin activity, the methods comprising administering an autotaxin inhibitor.

In one aspect, provided herein are methods for the attenuation, reversal and/or cessation of a sign, symptom or complication of a condition, disease or disorder associated with autotaxin activity, the methods comprising administering an autotaxin inhibitor in combination with one or more additional therapies.

In some embodiments, the administration of an autotaxin inhibitor or the administration of a pharmaceutical composition comprising an autotaxin inhibitor described herein, comprises the administration of an autotaxin inhibitor at a therapeutically effective dose. In some embodiments, a therapeutically effective dose is between about 0.01 mg to 5000 mg. For example, a therapeutic dose is between about 0.1 mg and about 5000 mg, between about 0.1 mg and about 1000 mg, between about 0.1 mg and about 500 mg, between about 0.1 mg and about 250 mg, between about 1 mg and about 1000 mg, between about 1 mg and about 100 mg, between about 1 mg and about 10 mg, or any integer between the aforementioned values. In some embodiments, a therapeutically effective dose is administered continuously. In some implementations, a therapeutically effective dose is administered 4 times a day, 3 times a day, 2 times a day, once a day, 6 times a week, 5 times a week, 4 times a week, 3 times a week, twice per week, once per week, or less often. In some embodiments, an autotaxin inhibitor is administered for a therapeutically effective amount of time in any of the methods described herein comprising the administration of an autotaxin inhibitor or pharmaceutical composition comprising an autotaxin inhibitor. In some instances, a therapeutically effective amount of time is the time it takes to decrease or eliminate one or more signs or symptoms of a disease, condition or disorder described herein. For example, a therapeutically effective amount of time is between 1 day and 1 year. The aforementioned therapeutic dosage examples are not limiting. Additional therapeutic regimens are further described elsewhere herein.

Fibrosis

In some embodiments, disclosed herein are methods of treating fibrosis with an autotaxin inhibitor. In some embodiments, disclosed herein are methods of preventing fibrosis with an autotaxin inhibitor. In some embodiments, disclosed herein are methods of attenuating, reversing, or inhibiting a sign or symptom of fibrosis.

In some embodiments, disclosed herein are methods comprising the administration of an autotaxin inhibitor to a subject having fibrosis. In some embodiments, disclosed herein are methods comprising the administration of an autotaxin inhibitor to a subject susceptible to fibrosis.

In some embodiments, disclosed herein are methods of reducing fibrosis in a tissue comprising contacting a fibrotic cell or tissue with an autotaxin inhibitor, in an amount sufficient to decrease and/or inhibit the fibrosis. In some embodiments, the fibrosis includes a fibrotic condition. In some cases, the amount sufficient to decrease and/or inhibit fibrosis is a therapeutically effective amount.

In some embodiments, reducing fibrosis, or treatment of a fibrotic condition, includes reducing or inhibiting one or more of: formation or deposition of extracellular matrix proteins; the number of pro-fibrotic cell types (e.g., fibroblast or immune cell numbers); cellular collagen or hydroxyproline content within a fibrotic lesion; expression or activity of a fibrogenic protein; reducing fibrosis associated with an inflammatory response; or a combination thereof.

"Fibrosis," as used herein, refers to the accumulation of extracellular matrix constituents that occurs following trauma, inflammation, tissue repair, immunological reactions, cellular hyperplasia, and/or neoplasia. Examples of tissue fibrosis include, but are not limited to, pulmonary fibrosis, renal fibrosis, cardiac fibrosis, cirrhosis and fibrosis of the liver, ocular fibrosis, skin scars and keloids, kidney fibrosis, peritoneal fibrosis, adhesions, fibromatosis, atherosclerosis, and amyloidosis.

In some embodiments, the fibrotic condition is primary fibrosis. In some embodiments, the fibrotic condition is idiopathic. In some embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In some embodiments, the fibrotic condition is a fibrotic condition of the lung, a fibrotic condition of the liver, a fibrotic condition of the heart or vasculature, a fibrotic condition of the kidney, a fibrotic condition of the skin, a fibrotic condition of the gastrointestinal tract, a fibrotic condition of the eye, a fibrotic condition of the bone marrow or a hematopoietic tissue, a fibrotic condition of the nervous system, fibrotic condition of the peritoneum, or a combination thereof.

In some embodiments, the fibrotic condition affects a tissue chosen from one or more of muscle, tendon, cartilage, skin (e.g., skin epidermis or endodermis), cardiac tissue, vascular tissue (e.g., artery, vein), pancreatic tissue, lung tissue, liver tissue, kidney tissue, uterine tissue, ovarian tissue, neural tissue, testicular tissue, peritoneal tissue, colon, small intestine, biliary tract, gut, bone marrow, or hematopoietic tissue.

In some embodiments, the fibrotic condition is a fibrotic condition of the liver. In certain embodiments, the fibrotic condition of the liver is chosen from one or more of: fatty liver disease, steatosis (e.g., nonalcoholic steatohepatitis (NASH)), cholestatic liver disease (e.g., primary biliary cirrhosis (PBC)), cirrhosis, alcohol-induced liver fibrosis, biliary duct injury, biliary fibrosis, cholestasis or cholangiopathies. In some embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, and exposure to toxins or irritants (e.g., alcohol, pharmaceutical drugs and environmental toxins).

In some embodiments, described herein are methods for the treatment or prevention of fibrosis of the liver in a subject, the methods comprising administration of an autotaxin inhibitor to the subject. In some instances, the fibrosis is chronic or acute. In some cases, administration of an autotaxin inhibitor results in the attenuation, delay or prevention of a sign, symptom and/or complication of liver fibrosis. For example, the method attenuates, delays or prevents the onset of cirrhosis, liver failure, portal hypertension, and/or complications thereof. Exemplary complications of cirrhosis include ascites, renal failure, hepatic encephalopathy, and variceal bleeding. In some cases, administration of an autotaxin inhibitor inhibits the accumulation of fibrogenic cells and/or prevents the deposition of extracellular matrix proteins (e.g., collagen) within the liver. Autotaxin inhibitors used in a method provided herein are useful for the treatment of liver fibrosis caused by any source of liver damage. Examples of liver fibrosis causes include, without limitation, viral infection (e.g., hepatitis C), autoimmune hepatitis, congenital hepatic fibrosis, bacterial infection (e.g., Brucellosis), parasitic infection (e.g., Echinococcosis), alcohol abuse, primary sclerosing cholangitis, drugs (e.g., amiodarone, chlorpromaxine, isoniazid, methotrexate, methyldopa, oxyphenisatin, tolbutamide), mechanical obstruction (e.g., surgery) nonalcoholic steatohepatitis (NASH), and combinations thereof.

In some cases, described herein are methods for the reversal of fibrosis or fibrosis regression of the liver in a subject, the methods comprising administration of an autotaxin inhibitor to the subject.

In some embodiments, any method provided herein comprising the administration of an autotaxin inhibitor, further comprises the administration of one or more additional fibrosis therapies. Additional fibrosis therapies include, for example, the administration of an angiotensin inhibitor, colchicine, corticosteroid, endothelin inhibitor, interferon-alpha, interleukin 10, antioxidant, hepatic stellate cell (HSC) inhibitor, or combination thereof.

In some embodiments, the fibrotic condition is a fibrotic condition of the kidney. In some embodiments, the fibrotic condition of the kidney is chosen from one or more of: renal fibrosis (e.g., chronic kidney fibrosis), nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathy renal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, or a chemotherapeutic agent.

In some embodiments, described herein are methods for the treatment or prevention of fibrosis of the kidney in a subject, the methods comprising the administration of an autotaxin inhibitor to the subject. In some instances, administration of an autotaxin inhibitor to the subject attenuates, delays or inhibits the progression of kidney fibrosis. In some cases, administration of an autotaxin inhibitor results in the attenuation, delay or prevention of a sign, symptom and/or complication of kidney fibrosis. In some instances, administration of an autotaxin inhibitor reduces the accumulation of extracellular matrix or the rate of accumulation of extracellular matrix in the kidney. In some cases, kidney fibrosis is the result of acute or chronic, sustained injury to kidney tissue. In some cases, kidney fibrosis is characterized by glomerulosclerosis. In some cases, kidney fibrosis is characterized by tubulointerstitial fibrosis.

In some cases, described herein are methods for the reversal of fibrosis or fibrosis regression of the kidney in a subject, the methods comprising administration of an autotaxin inhibitor to the subject.

In some embodiments, any method provided herein comprising the administration of an autotaxin inhibitor, further comprises the administration of one or more additional fibrosis and/or kidney disease therapies. An additional therapy comprises, for example, inhibiting profibrotic TGF-β/Smad signaling. As another example, an additional therapy comprises increasing the concentration of antifibrotic factors in the kidney, for example, hepatocyte growth factor (HGF) and bone morphogenetic protein-7 (BMP-7), which can antagonize fibrogenic action of TGF-β. Exemplary fibrosis treatments also include, without limitation, the administration of one or more of: pirfenidone (5-methyl-N-phenyl-2-(1H)-pyridone), tranilast, fluorofenidone, blockade of renin-angiotensin-aldosterone, ACE inhibitors, ADAM inhibitors, and an anti-CTGF monoclonal antibody.

In some embodiments, the fibrotic condition is a fibrotic condition of the skin. In some embodiments, the fibrotic condition of the skin is chosen from one or more of: skin fibrosis, scleroderma, nephrogenic systemic fibrosis (e.g., resulting after exposure to gadolinium which is frequently used as a contrast substance for MRIs in patients with severe kidney failure), scarring and keloid.

In some embodiments, described herein are methods for the treatment or prevention of fibrosis of the skin in a subject, the methods comprising the administration of an autotaxin inhibitor to the subject. In some instances, administration of an autotaxin inhibitor to the subject attenuates, delays or inhibits the progression of skin fibrosis. In some cases, administration of an autotaxin inhibitor results in the attenuation, delay or prevention of a sign, symptom and/or complication of skin fibrosis. In some instances, administration of an autotaxin inhibitor reduces the accumulation of extracellular matrix or the rate of accumulation of extracellular matrix in the skin. In some cases, skin fibrosis is the result of acute or chronic, sustained injury to skin tissue.

In some embodiments, following administration of an autotaxin inhibitor to a subject having skin fibrosis, the dermal thickness of the fibrotic skin decreases. For example, administration of an autotaxin inhibitor decreases dermal thickness of skin fibrosis by at least about 5%, 10%, 20%, 30%, 40% or 50% as compared to dermal thickness prior to autotaxin inhibitor administration.

In some embodiments, described herein are methods for the reversal of fibrosis or fibrosis regression of the skin of a subject, the methods comprising administration of an autotaxin inhibitor to the subject.

In some embodiments, any method provided herein comprising the administration of an autotaxin inhibitor, further comprises the administration of one or more additional fibrosis and/or skin disease therapies. Skin fibrosis therapies include, without limitation, administration of D-penicillamine, bovine collagen, methotrexate, mycophenolate mofetil, human relaxin, interferon-alpha, anti-transforming growth factor beta antibodies, or a combination thereof.

In some embodiments, the fibrotic condition is a fibrotic condition of the eye. In some embodiments, the fibrotic condition of the eye is chosen from one or more of: glaucoma, subretinal fibrosis, age-related macular degeneration (ARMD), diabetic retinopathy (DR), retinopathy of prematurity (ROP), fibrosis following eye surgery (glaucoma surgery, cataract surgery, LASIK surgery).

In some embodiments, described herein are methods for the treatment or prevention of fibrosis of the eye of a subject, the methods comprising the administration of an autotaxin inhibitor to the subject. In some instances, administration of an autotaxin inhibitor to the subject attenuates, delays or inhibits the progression of ocular fibrosis. In some cases, administration of an autotaxin inhibitor results in the attenuation, delay or prevention of a sign, symptom and/or complication of ocular fibrosis. In some instances, administration of an autotaxin inhibitor reduces the accumulation of extracellular matrix or the rate of accumulation of extracellular matrix in the eye. In some cases, ocular fibrosis is the result of acute or chronic, sustained injury to eye tissue.

In some embodiments, following administration of an autotaxin inhibitor to a subject having ocular fibrosis, the extent of fibrosis of the eye decreases. For example, administration of an autotaxin inhibitor decreases fibrosis of the bleb following trabeculectomy surgery and reduces the failure rate of the bleb due to fibrosis by about 5%, 10%, 20%, 30%, 40% or 50% as compared to patients without treatment with an autotaxin inhibitor.

In some embodiments, described herein are methods for the reversal of fibrosis or fibrosis regression of the eye of a subject, the methods comprising administration of an autotaxin inhibitor to the subject.

In some embodiments, any method provided herein comprising the administration of an autotaxin inhibitor, further comprises the administration of one or more additional fibrosis and/or eye disease therapies. Eye fibrosis therapies include, without limitation, administration of mitomycin, 5-fluorouracil, corticosteroids, antibiotics, anti-transforming growth factor beta antibodies, or a combination thereof.

In some embodiments, the fibrotic condition is a fibrotic condition of the peritoneum. In some embodiments, described herein are methods for the treatment or prevention of fibrosis of the peritoneum a subject, the methods comprising the administration of an autotaxin inhibitor to the subject. In some instances, administration of an autotaxin inhibitor to the subject attenuates, delays or inhibits the progression of peritoneal fibrosis. In some cases, administration of an autotaxin inhibitor results in the attenuation, delay or prevention of a sign, symptom and/or complication of peritoneal fibrosis. In some instances, administration of an autotaxin inhibitor reduces the accumulation of extracellular matrix or the rate of accumulation of extracellular matrix in the peritoneum.

In some embodiments, fibrosis of the peritoneum is caused by long-term peritoneal dialysis. In some embodiments, an autotaxin inhibitor is administered to a subject having peritonitis. In some embodiments, peritoneal fibrosis is caused by one or more of the following insults: bioincompatible dialysates, peritonitis, uremia, and/or chronic inflammation.

In some cases, described herein are methods for the reversal of fibrosis or fibrosis regression of the peritoneum of a subject, the methods comprising administration of an autotaxin inhibitor to the subject.

In some embodiments, any method provided herein comprising the administration of an autotaxin inhibitor, further comprises the administration of an anti-inflammatory agent or an immunosuppressant.

In some embodiments, the fibrotic condition is a fibrotic condition of the gastrointestinal tract. In some embodiments, the fibrotic condition is chosen from one or more of fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease.

In some embodiments, the fibrotic condition is a fibrotic condition of the lung. In some embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiolitis obliterans, or bronchiectasis. In some embodiments, the fibrosis of the lung is secondary to a disease, a toxin, an insult, a medical treatment, or a combination thereof. In some embodiments, fibrosis of the lung is associated with one or more of: a disease process such as asbestosis and silicosis; an occupational hazard; an environmental pollutant; cigarette smoking; an autoimmune connective tissue disorders (e.g., rheumatoid arthritis, scleroderma and systemic lupus erythematosus (SLE)); a connective tissue disorder such as sarcoidosis; an infectious disease, e.g., infection, particularly chronic infection; a medical treatment, including but not limited to, radiation therapy, and drug therapy, e.g., chemotherapy (e.g., treatment with as bleomycin, methotrexate, amiodarone, busulfan, and/or nitrofurantoin). In some embodiments, the fibrotic condition of the lung treated with the methods of the invention is associated with (e.g., secondary to) a cancer treatment, e.g., treatment of a cancer (e.g. squamous cell carcinoma, testicular cancer, Hodgkin's disease with bleomycin).

In some embodiments, the fibrotic condition is a fibrotic condition of the heart. In certain embodiments, the fibrotic condition of the heart is myocardial fibrosis (e.g., myocardial fibrosis associated with radiation myocarditis, a surgical procedure complication (e.g., myocardial post-operative fibrosis), infectious diseases (e.g., Chagas disease, bacterial, trichinosis or fungal myocarditis)); granulomatous, metabolic storage disorders (e.g., cardiomyopathy, hemochromatosis); developmental disorders (e.g., endocardial fibroelastosis); arteriosclerotic, or exposure to toxins or irritants (e.g., drug induced cardiomyopathy, drug induced cardiotoxicity, alcoholic cardiomyopathy, cobalt poisoning or exposure). In some embodiments, the myocardial fibrosis is associated with an inflammatory disorder of cardiac tissue (e.g., myocardial sarcoidosis).

In some embodiments, the fibrotic condition is adhesions. In some embodiments, the adhesions are chosen from one or more of: abdominal adhesions, peritoneal adhesions, pelvic adhesions, pericardial adhesions, peridural adhesions, peritendinous or adhesive capsulitis.

In some embodiments, the fibrotic condition is a fibrotic condition of the eye. In some embodiments, the fibrotic condition of the eye involves diseases of the anterior segment of the eye such as glaucoma and corneal opacification; in some embodiments, the fibrotic condition of the eye involves disease of the posterior segment of the eye such as age-related macular degeneration, diabetic retinopathy, retinopathy of prematurity and neovascular glaucoma; in some embodiments, the fibrotic condition of the eye results from fibrosis following ocular surgery.

In some embodiments, the fibrotic condition is a fibrotic condition of the bone marrow or a hematopoietic tissue. In some embodiments, the fibrotic condition of the bone marrow is an intrinsic feature of a chronic myeloproliferative neoplasm of the bone marrow, such as primary myelofibrosis (also referred to herein as agnogenic myeloid metaplasia or chronic idiopathic myelofibrosis). In some embodiments, the bone marrow fibrosis is associated with (e.g., is secondary to) a malignant condition or a condition caused by a clonal proliferative disease. In some embodiments, the bone marrow fibrosis is associated with a hematologic disorder (e.g., a hematologic disorder chosen from one or more of polycythemia vera, essential thrombocythemia, myelodysplasia, hairy cell leukemia, lymphoma (e.g., Hodgkin or non-Hodgkin lymphoma), multiple myeloma or chronic myelogeneous leukemia (CML)). In some embodiments, the bone marrow fibrosis is associated with (e.g., secondary to) a non-hematologic disorder (e.g., a non-hematologic disorder chosen from solid tumor metastasis to bone marrow, an autoimmune disorder (e.g., systemic lupus erythematosus, scleroderma, mixed connective tissue disorder, or polymyositis), an infection (e.g., tuberculosis), or secondary hyperparathyroidism associated with vitamin D deficiency.

Colitis

In some embodiments, disclosed herein are methods of treating colitis with an autotaxin inhibitor. In some embodiments, disclosed herein are methods of preventing colitis with an autotaxin inhibitor. In some embodiments, disclosed herein are methods of attenuating, reversing, or inhibiting a sign or symptom of colitis.

In some embodiments, disclosed herein are methods comprising the administration of an autotaxin inhibitor to a subject having colitis. In some embodiments, disclosed herein are methods comprising the administration of an autotaxin inhibitor to a subject susceptible to colitis.

In some embodiments, disclosed herein are methods of reducing colitis in a tissue, the methods comprising contacting a tissue with an autotaxin inhibitor, in an amount sufficient to decrease or inhibit the colitis. In some cases, the amount sufficient to decrease and/or inhibit colitis is a therapeutically effective amount.

"Colitis," as used herein, refers to an inflammation of colon tissue. Colitis includes acute, self-limited and chronic colitis. Colitis includes autoimmune colitis, idiopathic colitis, latrogenic colitis, vascular disease and infectious colitis. Autoimmune types of colitis include inflammatory bowel disease and ulcerative colitis. Idiopathic types of colitis include microscopic colitis, lymphocytic colitis and collagenous colitis. Latrogenic types of colitis include diversion colitis and chemical colitis. Colitis caused by vascular disease includes ischemic colitis. Infectious colitis includes colitis caused by *Clostridium difficile*, *Shigella dysenteriae* or Shigatoxigenic group of *Escherichia coli*. In some embodiments, colitis comprises ulcerative colitis.

In some embodiments, disclosed herein are methods of treating colitis in a subject by administering an autotaxin inhibitor to the subject. In some embodiments, one or more signs or symptoms of colitis are reduced in a subject after administration of an autotaxin inhibitor. Signs or symptoms of colitis include, without limitation, abdominal pain, loss of appetite, fatigue, diarrhea, mucus in the stool, cramping, urgency, bloating, abdominal tenderness, weight loss, changes in bowel habits such as increased frequency, fever, bleeding, bloody stool, distension, colonic mucosal erythema and ulcers.

In some embodiments, following administration of an autotaxin inhibitor to a subject having colitis, the subject shows improvement in colitis clinical signs, symptoms or histopathology. In one example, following autotaxin inhibitor administration, colon inflammation is decreased. In another example, following autotaxin inhibitor administration, tissue damage is reversed. In another example, following autotaxin inhibitor administration, tissue damage progression is attenuated. In yet another example, following autotaxin inhibitor administration, tissue damage is inhibited. Tissue damage can be visualized, for example, by histology using a stain such as trichrome stain (Masson).

In some embodiments, following autotaxin inhibitor administration to a subject having ulcerative colitis, ulcer area is decreased, for example, by at least about 1%, 2%, 3%, 4%, 5%, 10%, 15%, 20%, 50%, 90%, 99% of its size prior to autotaxin inhibitor administration. In another example, following autotaxin inhibitor administration, ulcer area is at least about 2-fold, 3-fold or 5-fold smaller in size than prior to autotaxin inhibitor administration or as compared to administration of a control.

In some embodiments, following autotaxin inhibitor administration to a subject having colitis, the subject's body weight does not increase or decrease by more than about 2%, 5% or 10%.

In some embodiments, following autotaxin inhibitor administration to a subject having colitis, the subject has an increase in stool consistency.

In some embodiments, a subject having colitis is treated by administration of an autotaxin inhibitor and one or more additional treatments. Addition treatments include hydration therapy and administration of a steroid, anti-inflammatory agent, and/or immunosuppressant. In one example, the additional treatment is cyclosporin A (CsA). In another example, the additional treatment is sulfasalazine.

In some embodiments, an animal model induced with colitis (e.g., DSS-induced colitis or DNBS-induced colitis) is administered (prophylactically or therapeutically) an autotaxin inhibitor; wherein following autotaxin inhibitor administration, the animal exhibits an increase in colon length, an increase in colon weight, or both an increase in colon length and weight. For example, following administration of an autotaxin inhibitor to a mouse or rat induced with colitis, the colon length increases by at least about 0.1 cm, 0.2 cm, 0.3 cm, 0.4 cm, 0.5 cm, 1 cm, 2 cm or 3 cm as compared to administration of a vehicle or control. In another example, following administration of an autotaxin inhibitor to a mouse or rat induced with colitis, the colon weight increases by at least about 0.05 g as compared to administration of a vehicle or control. In some embodiments, following autotaxin inhibitor treatment of a mouse or rat induced with colitis, the mouse or rat has a reduction in ulcer area by at least about 10%, 20%, 50% or 90% as compared to ulcer area prior to administration. In some embodiments, following autotaxin inhibitor treatment of a mouse or rat induced with colitis, the mouse or rat has an ulcer area less than about 90%, 80%, 70%, 50%, 20%, or 10% of ulcer area size in an untreated or control mouse or rat having induced colitis.

Pruritus

In some embodiments, disclosed herein are methods of treating pruritus with an autotaxin inhibitor. In some embodiments, disclosed herein are methods of preventing pruritus with an autotaxin inhibitor. In some embodiments, disclosed herein are methods of attenuating, reversing or inhibiting at least one sign or symptom of pruritus.

In some embodiments, disclosed herein are methods comprising the administration of an autotaxin inhibitor to a subject having pruritus. In some embodiments, disclosed herein are methods comprising the administration of an autotaxin inhibitor to a subject susceptible to pruritus.

In some embodiments, disclosed herein are methods of reducing pruritus in a tissue, the methods comprising contacting a tissue with an autotaxin inhibitor, in an amount sufficient to decrease or inhibit the pruritus.

Pruritus is a condition involving localized or general itching that is a common and distressing symptom in a variety of diseases. Although usually occurring in the skin, pruritus can also occur in non-cutaneous sites such as mucous membranes. Pruritus is a frequent manifestation of localized skin disorders caused by hypersensitivity reactions such as allergic reactions to insect bites or to environmental allergens, urticaria, dermatoses of fungal and bacterial origins, ectoparasite infections, and hemorrhoids. In some embodiments, disclosed herein are method of treating pruritus caused by systemic diseases, including, for example, hypothyroidism, thyrotoxicosis, mucocandiasis in diabetes mellitus, and Hodgkin's disease. In some embodiments, disclosed herein are methods of treating bouts of persistent or recurrent pruritus associated with many systemic diseases and skin disorders. Pruritus includes, without limitation, renal pruritus, cholestatic pruritus, hematologic pruritus and endocrine pruritus.

In some embodiments, disclosed herein are methods of treating pruritus associated with liver diseases and intrahepatic or posthepatic cholestasis. Hepatic diseases leading to pruritus include primary biliary cirrhosis, B and C viral hepatitis, primary sclerosing cholangitis, carcinoma of bile ducts, alcoholic cirrhosis, autoimmune hepatitis and others.

In some embodiments, disclosed herein are methods of treating pruritus arising from a variety of causes such as xerosis, skin conditions (such as psoriasis, eczema, sunburn, athlete's foot), insect bites, poisonous plants (such as poison ivy, poison oak, poison sumac), Hodgkin's disease, jaundice, polycythemia, scabies, lice, worms, thyroid illness, diabetes mellitus, dandruff, iron deficiency anemia, parasitic infections, medications, cholestasis, pruritus related to pregnancy, HIV infection, other causes of itching or pruritus, or combinations thereof.

In some embodiments, disclosed herein are methods of treating or preventing pruritus in a subject in need thereof, the methods comprising the administration of an autotaxin inhibitor to the subject. In some embodiments, administration of an autotaxin inhibitor reduces pruritus by at least about 10%, 20%, 30%, 50%, or 90%.

In some embodiments, following autotaxin inhibitor administration to a subject having pruritus, the subject has a decrease in total number of scratch movements as compared to scratch number before autotaxin inhibitor administration. For example, scratch movements decrease by at least about 10%, 20%, 50%, or 90%. In some embodiments, pruritus is prevented or treated by the administration of an autotaxin inhibitor and one or more additional pruritus therapies or therapeutic agents. Pruritus therapies include, without limitation, use of skin creams and lotions to prevent skin dryness and use of an antihistamine, steroid or antibiotic. Pruritus therapeutic agents include, doxepin, mirtazapine, gabapentin, aprepitant, capsaicin, tacrolimus, gamma linolenic acid, cholestyramine, rifampin, an opioid antagonist, ondansetron, and activated charcoal.

In some embodiments, described herein are methods for the prevention or treatment of renal pruritus in a subject, the methods comprising administration of an autotaxin inhibitor to the subject. In some embodiments, described herein are methods for the prevention or treatment of cholestatic pruritus in a subject, the methods comprising administration of an autotaxin inhibitor to the subject. In some embodiments, described herein are methods for the prevention or treatment of hematologic pruritus in a subject, the methods comprising administration of an autotaxin inhibitor to the subject. In some embodiments, described herein are methods for the prevention or treatment of endocrine pruritus in a subject, the methods comprising administration of an autotaxin inhibitor to the subject.

Neurological Disease

In some embodiments, disclosed herein are methods of treating a neurological disease, condition or disorder with an autotaxin inhibitor. In some embodiments, disclosed herein are methods of preventing a neurological disease, condition or disorder with an autotaxin inhibitor. In some embodiments, disclosed herein are methods of attenuating, reversing or inhibiting a sign or symptom of a neurological disease, condition or disorder.

In some embodiments, disclosed herein are methods comprising the administration of an autotaxin inhibitor to a subject having a neurological disease, condition or disorder. In some embodiments, disclosed herein are methods comprising the administration of an autotaxin inhibitor to a subject susceptible to having a neurological disease, condition or disorder.

In some embodiments, the neurological disease is multiple sclerosis. In some instances, the neurological disease is caused by a genetic disorder. In some instances, the neurological disease is developmental, for example, spina bifida. In some instances, the neurological disease is a degenerative disease, for example, Parkinson's disease or Alzheimer's disease. In some instances, the neurological disease results from a stroke. Neurological diseases, conditions and disorders or characteristics of neurological diseases, conditions and disorders suitable for treatment with an ATX inhibitor include, without limitation, Amyotrophic lateral sclerosis (ALS), Arteriovenous malformations (AVMs), brain aneurysm, brain tumor, Dural arteriovenous fistulae, epilepsy, headache, memory disorders, Parkinson's disease, peripheral neuropathy, post-herpetic neuralgia, spinal cord tumor and stroke. In certain instances, autotaxin activity is increased in CSF (cerebrospinal fluid) and serum of relapse/remitting multiple sclerosis patients compared to patients with other neurological diseases.

In some embodiments, the mutiple sclerosis is relapsing-remitting multiple sclerosis, relapsing multiple sclerosis, primary-progressive multiple sclerosis, or secondary-progressive multiple sclerosis.

In some embodiments, the mutiple sclerosis is relapsing-remitting multiple sclerosis (RRMS). People with this type of MS have clearly defined attacks of worsening neurologic function. These attacks are followed by partial or complete recovery periods called remissions. During remission, symptoms often improve and there is no apparent worsening or progression of disease. About 85% of people with MS are initially diagnosed with RRMS.

In some embodiments, the mutiple sclerosis is relapsing multiple sclerosis (RMS). RMS includes several forms of MS that have relapsing features, including relapsing-remitting MS, progressive-relapsing MS, and secondary-progressive MS.

In some embodiments, the mutiple sclerosis is primary-progressive multiple sclerosis (PPMS). This form has a steady worsening of neurologic functioning, but without any distinct relapses or periods of remission. A person's rate of progression may vary over time—with occasional plateaus or temporary improvements—but the progression is continuous. 10% of people are diagnosed with this type of MS.

In some embodiments, the mutiple sclerosis is secondary-progressive multiple sclerosis (SPMS). Following an initial period of relapsing-remitting MS (RRMS), many people transition to SPMS. The disease begins to worsen more steadily, with or without occasional relapses, remissions, or plateaus.

In some embodiments, disclosed herein are methods of treating a nervous system injury in a subject, for example, injury to the brain, spinal cord and/or nerve tissue, the methods comprising the administration of an autotaxin inhibitor to the subject.

In some embodiments, disclosed herein are methods for the treatment of a cancer affecting the nervous system of a subject, the methods comprising the administration of an autotaxin inhibitor to the subject. In some examples, the cancer is brain cancer.

In some embodiments, disclosed herein are methods of treating injury-induced demyelination in a subject, the methods comprising the administration of an autotaxin inhibitor to the subject.

In some embodiments, disclosed herein are methods of treating an infection of the nervous system in a subject, the methods comprising the administration of an autotaxin inhibitor to the subject. In some examples, the nervous system infection includes meningitis.

In some embodiments, disclosed herein are methods of treating a neurological disease, disorder or condition in a subject, the methods comprising administration of an autotaxin inhibitor to the subject in need thereof. In some embodiments, disclosed herein are methods of treating multiple sclerosis in a subject, the methods comprising administering an autotaxin inhibitor to the subject. In some embodiments, treatment includes the inhibition or reversal of demyelination. Inhibition of demyelination includes a decrease in rate of demyelination as compared to the absence of autotaxin inhibitor treatment, where a decrease in rate is a decrease of at least 5%, 10%, 20%, 30%, 40%, 50%, 80% or 90% demyelination. In some instances, administration of an autotaxin inhibitor prevents, delays and and/or attenuates demyelination.

In some embodiments, disclosed herein are methods of preventing or treating a sign, symptom and/or complication of a neurological disease, disorder or condition, the methods comprising administration of an autotaxin inhibitor. In some embodiments, disclosed herein are methods of preventing or treating a sign, symptom and/or complication of multiple sclerosis in a subject, the methods comprising administering an autotaxin inhibitor to the subject. Signs and symptoms of multiple sclerosis include, without limitation, numbness or weakness in one or more limbs, partial or complete loss of vision, double vision, blurring of vision, tingling sensation, electric-shock sensations, tremors, lack of coordination, unsteady gait, slurred speech, fatigue, dizziness, and changes in bowel and/or bladder function. Examples of multiple sclerosis complications include, without limitation, muscle stiffness, muscle spasms, paralysis, mental changes such as forgetfulness and mood swings, depression and epilepsy.

In some embodiments, disclosed herein are methods of decreasing the frequency, severity and/or duration of a relapse of a neurological disease, disorder or condition, the methods comprising administration of an autotaxin inhibitor. In some embodiments, disclosed herein are methods of decreasing the frequency, severity and/or duration of a relapse of multiple sclerosis, the methods comprising administration of an autotaxin inhibitor. In some instances, administration of an autotaxin inhibitor decreases or stops the progression of one or more symptoms in a patient having multiple sclerosis. In some instances, administration of an autotaxin inhibitor prevents or delays the onset of multiple sclerosis symptoms.

In some instances, a neurological disorder such as multiple sclerosis is treated with a combination of an autotaxin inhibitor and one or more additional treatments. Addition treatments include, without limitation, plasma exchange, physical therapy, muscle relaxants, exercise, rest, and administration of one or more of the following: corticosteroids, beta interferons, glatiramer acetate, dimethyl fumarate, fingolimod, teriflunomide, natalizumab, mitoxantrone; and combinations thereof.

Neurological diseases, conditions and disorders or characteristics of neurological diseases, conditions and disorders suitable for treatment with an autotaxin inhibitor include, without limitation, absence of the septum pellucidum, acid lipase disease, acid maltase deficiency, acquired epileptiform aphasia, acute disseminated encephalomyelitis, ADHD, Adie's pupil, Adie's syndrome, adrenoleukodystrophy, agenesis of the corpus callosum, agnosia, aicardi syndrome, neurological complications from AIDS, Alexander disease, Alpers' disease, alternating hemiplegia, Alzheimer's disease, amyotrophic lateral sclerosis (ALS), anencephaly, aneurysm, angelman syndrome, angiomatosis, anoxia, antiphospholipid syndrome, aphasia, apraxia, arachnoid cysts, arachnoiditis, Arnold-Chiari malformation, arteriovenous malformation, Asperger syndrome, ataxia, stroke, Barth syndrome, batten disease, Becker's myotonia, Behcet's disease, Bell's palsy, benign essential blepharospasm, benign focal amyotrophy, benign intracranial hypertension, Bernhardt-Roth syndrome, Binswanger's disease, blepharospasm, Bloch-Sulzberger syndrome, brachial plexus injuries, Bradbury-Eggleston syndrome, brain aneurysm, brain injury, Brown-Sequard syndrome, CADASIL, canavan disease, causalgia, cavernomas, cavernous angioma, cavernous malformation, central cord syndrome, central pain syndrome, central pontine myelinolysis, cephalic disorders, ceramidase deficiency, cerebellar degeneration, cerebellar hypoplasia, cerebral aneurysms, cerebral arteriosclerosis, cerebral atrophy, cerebral beriberi, cerebral cavernous malformation, cerebral gigantism, cerebral hypoxia, cerebral palsy, cerebro-oculo-facio-skeletal syndrome, chiari malformation, chorea, choreoacanthocytosis, chronic inflammatory demyelinating polyneuropathy (CIDP), chronic orthostatic intolerance, cockayne syndrome type II, Coffin Lowry syndrome, colpocephaly, coma, complex regional pain syndrome, congenital facial diplegia, congenital myasthenia, congenital myopathy, congenital vascular cavernous malformations, corticobasal degeneration, cranial arteritis, craniosynostosis, cree encephalitis, Creutzfeldt-Jakob disease, cumulative trauma disorders, Cushing's syndrome, cytomegalic inclusion body disease, cytomegalovirus infection, Dandy-Walker syndrome, Dawson disease, De Morsier's syndrome, Dejerine-Klumpke palsy, dementia, dentate cerebellar ataxia, dentatorubral atrophy, dermatomyositis, developmental dyspraxia, Devic's syndrome, diabetic neuropathy, diffuse sclerosis, dravet syndrome, dysautonomia, dysgraphia, dysphagia, dyspraxia, dyssynergia cerebellaris, dystonias, bulbospinal muscular atrophy, encephalopathy, empty sella syndrome, encephalitis, encephaloceles, encephalotrigeminal angiomatosis, epilepsy, Erb-Duchenne and Dejerine-Klumpke Palsies, Erb's palsy, extrapontine myelinolysis, fabry disease, Fahr's syndrome, familial dysautonomia, familial hemangioma, familial idiopathic basal ganglia calcification, familial periodic paralyses, familial spastic paralysis, Farber's Disease, febrile seizures, fibromuscular dysplasia, fisher syndrome, Friedreich's ataxia, and frontotemporal dementia.

Inflammation and Inflammatory Disorders

In some embodiments, disclosed herein are methods of treating an inflammatory condition, disease, or disorder with an autotaxin inhibitor. In some embodiments, disclosed herein are methods of reducing inflammation in a tissue of a subject, the method comprising administering to the subject an autotaxin inhibitor. In some instances, the tissue is colon tissue.

As used in the present disclosure, "inflammation" refers to the well-known localized response to various types of injury or infection, which is characterized by redness, heat, swelling, and pain, and often also including dysfunction or reduced mobility.

The methods described herein, in some embodiments, include methods for the treatment, reduction of risk, and delaying onset of other inflammatory conditions or diseases with an autotaxin inhibitor, such as (a) ocular inflammation associated with corneal ulcers, giant papillary conjunctivitis, blepharitis, chelazion, uveitis, dry eye, post-surgical inflammation, and contact lens associated inflammation; (b) allergic diseases such as hay fever, rhinitis, seasonal allergic conjunctivitis, vernal conjunctivitis and other eosinophil-mediated conditions; (c) skin diseases such as psoriasis, contact dermatitis, eczema, infectious skin ulcers, open wounds, and cellulitis; (d) infectious diseases including sepsis, septic shock, encephalitis, infectious arthritis, endotoxic shock, gram negative shock, Jarisch-Herxheimer reaction, shingles, toxic shock, cerebral malaria, bacterial meningitis, acute respiratory distress syndrome (ARDS), lyme disease, and HIV infection; (e) wasting diseases such as cachexia secondary to cancer and HIV; (f) inflammation due to organ, tissue or cell transplantation (e.g., bone marrow, cornea, kidney, lung, liver, heart, skin, pancreatic islets) including transplant rejection, and graft versus host disease; (g) adverse effects from drug therapy, including adverse effects from amphotericin B treatment, adverse effects from immunosuppressive therapy, e.g., interleukin-2 treatment, adverse effects from OKT3 treatment, adverse effects from GM-CSF treatment, adverse effects of cyclosporine treatment, and adverse effects of aminoglycoside treatment, stomatitis, and mucositis due to immunosuppression; (h) cardiovascular conditions including circulatory diseases induced or exasperated by an inflammatory response, such as ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis, and the cardiovascular complications of diabetes; (i) dialysis, including pericarditis, due to peritoneal dialysis; (j) gout; and (k) chemical or thermal-induced inflammation due to burns, acid, alkali and the like.

Autoimmune Diseases

The methods described herein, in some embodiments, include methods for the treatment, reduction of risk, and delaying of onset of an autoimmune disease or disorder with an autotaxin inhibitor. Examples of autoimmune diseases include, but are not limited to, Alopecia Areata, Lupus, Ankylosing Spondylitis, Meniere's Disease, Antiphospholipid Syndrome, Mixed Connective Tissue Disease, Autoimmune Addison's Disease, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Multiple Sclerosis, Rheumatoid Arthritis, Essential Mixed, Cryoglobulinemia Sarcoidosis, Fibromyalgia, Scleroderma, Grave's Disease, Sjögren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Diabetes (Type II), Vasculitis, Lichen Planus, and Vitiligo.

In some embodiments, the methods for the treatment, reduction of risk, and delaying the onset of an autoimmune disease or disorder further comprise the administration of an immunosuppressant. Immunosuppressants include, without limitation, glucocorticoids, cytostatics, antibodies and drugs that act on immunophilins. Examples of glucocorticoids include cortisol, cortisone, prednisone, prednisolone, methylprednisolone, dexamethasone, betamethasone, triamcinolone, beclometasone, fludrocortisone, deoxycorticosterone, and aldosterone. Examples of cytostatics include alkylating agents (e.g., nitrogen mustards such as cyclophosphamide, nitrosoureas, platinum compounds) and antimetabolites (e.g., folic acid analogues such as methotrexate, purine analogues such as azathioprine and mercaptopurine, pyrimidine analogues such as fluorouracil, protein synthesis inhibitors). Examples of drugs for use in the methods described include ciclosporin, tacrolimus, sirolimus, interferons, opioids, TNF binding proteins, mycophenolate, and fingolimod. Examples of antibodies useful for co-administration with an autotaxin inhibitor in a method described herein include Antithymocyte globulin, 1D09C3, Adalimumab/D2E7 (Humira; Trudexa), Afelimomab, Afutuzumab/GA101 (type II), Alemtuzumab/Campath-1H (MabCampath), Apolizumab/Hu1D10, Aselizumab, Atlizumab, Basiliximab (Simulect), Bectumomab/IMMU-LL2, Belimumab (Benlysta, LymphoStat-B), Bertilimumab, BL22/CAT-3888, Brentuximab/cAC10/SGN-35, Briakinumab/ABT-874, Canakinumab/ACZ885 (Ilaris), Certolizumab pegol/CDP870 (Cimzia), Clenoliximab, Dacetuzumab/SGN-40, Daclizumab (Zenapax), Eculizumab/5G1.1 (Soliris), Efalizumab (Raptiva, formerly Xanelim), Epratuzumab/hLL2/IMMU-102 (Lymphocyde©), Fontolizumab, Fresolimumab/GC-1008, Galiximab/IDEC-114, Gavilimomab/ABX-CBL, Gemtuzumab, Golimumab/CNTO148 (Simponi), HL2434P (IMMU-114), Ibritumomab tiuxetan (MXDPTA)/IDEC Y2B8 (Zevalin), Infliximab/chimeric A2 (cA2) (Remicade), Inolimomab/BT563, Inotuzumab, Keliximab/IDEC CE9.1, Lerdelimumab/CAT-152, Lintuzumab/HuM195 (Zamyl), LMB-2, Lorvotuzumab mertansine, Lumiliximab/IDEC-152, Lym-1 (Oncolym), MDX-060, Mepolizumab/SB-240563, Metelimumab/CAT-192, Mogamulizumab/KW-0761/AMG-761, Moxetumomab pasudotox/CAT-8015/HA22, Muromonab-CD3 (Orthoclone OKT3), Natalizumab (Tysabri, Antegren), Nerelimomab/CDP571, Ocrelizumab/PRO70769 (type I), Odulimomab, Ofatumumab/2F2/HuMax-CD20 (Arzerra) (type I), Omalizumab (Xolair), Otelixizumab/TRX4, Pascolizumab/SB 240683, Reslizumab/SCH 55700 (Cinquil), Rituximab/chimeric 2B8 (IDEC-C2B8) (Rituxan, MabThera) (type I), Ruplizumab (Antova), SAR-3419, Secukinumab/AIN-457, SGN30, Siplizumab/MEDI-507, Teplizumab/MGA031/hOKT3γ1 (Ala-Ala), Tocilizumab (Actemra), Tositumomab (type II), Ustekinumab/CNTO 1275 (Stelara), Vedolizumab/MNL-0002, Veltuzumab/IMMU-106/hA20 (type I), Visilizumab (Nuvion), Zanolimumab/HuMax-CD4, Zolimomab aritox/H65, Abatacept/CTLA4-Ig/BMS-188667 (Orencia), Belatacept/LEA29Y, Atacicept/BLyS/APRIL-Ig, Etanercept/TNFR-Ig (Enbrel), Pegsunercept/pegylated TNFR-Ig, Alefacept (Amevive), and Rilonacept (Arcalyst). Immunosuppressive antibodies include antibodies that target complement-dependent proteins and interleukins.

Angiogenesis

In some embodiments, described herein are methods for the treatment or prevention of angiogenesis in a subject comprising the administration of an autotaxin inhibitor to the subject. Angiogenesis includes sprouting angiogenesis and intussusceptive angiogenesis. In some instances, the methods further comprise the administration of an angiogenesis inhibitor, for example, a VEGF inhibitor (bevacizumab), sorafenib sunitinib, pazopanib, everolimus, or a combination thereof.

Cancer

Autotaxin has been demonstrated to increase cell motility, neovascularization, proliferation and aggressiveness of tumors. It is upregulated in numerous tumor lineages, such as breast, renal, liver, glioblastoma, ovarian and prostate cancer.

In some embodiments, disclosed herein are methods of treating cancer with an autotaxin inhibitor.

Autotaxin is a prometastatic enzyme initially isolated from the conditioned medium of human melanoma cells. In addition, autotaxin overexpression is frequently observed in malignant tumor tissues such as breast cancer, renal cancer, Hodgkin lymphoma, hepatocellular carcinoma, pancreatic cancer and glioblastoma. LPA also contributes to tumorigenesis by increasing motility and invasiveness of cells.

The term "cancer" as used herein, refers to an abnormal growth of cells that tend to proliferate in an uncontrolled way and, in some cases, to metastasize (spread). Types of cancer include, but are not limited to, solid tumors (such as those of the bladder, bowel, brain, breast, endometrium, heart, kidney, lung, liver, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, desmoid tumors, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor.

In some embodiments, an autotaxin inhibitor, or a pharmaceutically acceptable salt thereof, is used in the treatment of ovarian cancer, prostate cancer, breast cancer, lung cancer, melanoma, head and neck cancer, bowel cancer (colorectal cancer), thyroid cancer, glioblastoma, follicular lymphoma, renal cancer, Hodgkin lymphoma, hepatocellular carcinoma, pancreatic cancer or melanoma.

In some embodiments, an autotaxin inhibitor disclosed herein, or a pharmaceutically acceptable salt thereof, is used in the treatment of bone metastases.

In some embodiments, an autotaxin inhibitor disclosed herein, or a pharmaceutically acceptable salt thereof, is used in the treatment of oral cancer, prostate cancer, rectal cancer, non-small cell lung cancer, lip and oral cavity cancer, liver cancer, lung cancer, anal cancer, kidney cancer, vulvar cancer, breast cancer, oropharyngeal cancer, nasal cavity and paranasal sinus cancer, nasopharyngeal cancer, urethra cancer, small intestine cancer, bile duct cancer, bladder cancer, ovarian cancer, laryngeal cancer, hypopharyngeal cancer, gallbladder cancer, colon cancer, colorectal cancer, head and neck cancer, parathyroid cancer, penile cancer, vaginal cancer, thyroid cancer, pancreatic cancer, esophageal cancer, Hodgkin's lymphoma, leukemia-related disorders, mycosis fungoides, or myelodysplastic syndrome.

In some embodiments, an autotaxin inhibitor disclosed herein, or a pharmaceutically acceptable salt thereof, is used in the treatment of non-small cell lung cancer, pancreatic cancer, breast cancer, ovarian cancer, colorectal cancer, or head and neck cancer.

In some embodiments, an autotaxin inhibitor, or a pharmaceutically acceptable salt thereof, is used in the treatment of a carcinoma, a tumor, a neoplasm, a lymphoma, a melanoma, a glioma, a sarcoma, or a blastoma.

In some embodiments, the carcinoma is selected from the group consisting of: carcinoma, adenocarcinoma, adenoid cystic carcinoma, adenosquamous carcinoma, adrenocortical carcinoma, well differentiated carcinoma, squamous cell carcinoma, serous carcinoma, small cell carcinoma, invasive squamous cell carcinoma, large cell carcinoma, islet cell carcinoma, oat cell carcinoma, squamous carcinoma, undifferentiatied carcinoma, verrucous carcinoma, renal cell carcinoma, papillary serous adenocarcinoma, merkel cell carcinoma, hepatocellular carcinoma, soft tissue carcinomas, bronchial gland carcinomas, capillary carcinoma, bartholin gland carcinoma, basal cell carcinoma, carcinosarcoma, papilloma/carcinoma, clear cell carcinoma, endometrioid adenocarcinoma, mesothelial, metastatic carcinoma, mucoepidermoid carcinoma, cholangiocarcinoma, actinic keratoses, cystadenoma, and hepatic adenomatosis.

In some embodiments, the tumor is selected from the group consisting of: astrocytic tumors, malignant mesothelial tumors, ovarian germ cell tumor, supratentorial primitive neuroectodermal tumors, Wilm's tumor, pituitary tumors, extragonadal germ cell tumor, gastrinoma, germ cell tumors, gestational trophoblastic tumor, brain tumors, pineal and supratentorial primitive neuroectodermal tumors, pituitary tumor, somatostatin-secreting tumor, endodermal sinus tumor, carcinoids, central cerebral astrocytoma, glucagonoma, hepatic adenoma, insulinoma, medulloepithelioma, plasmacytoma, vipoma, and pheochromocytoma.

In some embodiments, the neoplasm is selected from the group consisting of: intaepithelial neoplasia, multiple myeloma/plasma cell neoplasm, plasma cell neoplasm, interepithelial squamous cell neoplasia, endometrial hyperplasia, focal nodular hyperplasia, hemangioendothelioma, lymphangioleio myomatosis and malignant thymoma.

In some embodiments, the lymphoma is selected from the group consisting of: nervous system lymphoma, AIDS-related lymphoma, cutaneous T-cell lymphoma, non-Hodgkin's lymphoma, mantle cell lymphoma, follicular lymphoma and Waldenstrom's macroglobulinemia.

In some embodiments, the melanoma is selected from the group consisting of: acral lentiginous melanoma, superficial spreading melanoma, uveal melanoma, lentigo maligna melanomas, melanoma, intraocular melanoma, adenocarcinoma nodular melanoma, and hemangioma.

In some embodiments, the sarcoma is selected from the group consisting of: adenomas, adenosarcoma, chondosarcoma, endometrial stromal sarcoma, Ewing's sarcoma, Kaposi's sarcoma, leiomyosarcoma, rhabdomyosarcoma, sarcoma, uterine sarcoma, osteosarcoma, and pseudosarcoma.

In some embodiments, the glioma is selected from the group consisting of: glioma, brain stem glioma, and hypothalamic and visual pathway glioma.

In some embodiments, the blastoma is selected from the group consisting of: pulmonary blastoma, pleuropulmonary blastoma, retinoblastoma, neuroblastoma, medulloblastoma, glioblastoma, and hemangiblastomas.

Airway Diseases

Inflammatory conditions, diseases, and disorders, which can be treated with an autotaxin inhibitor, include airway diseases comprising pulmonary inflammation, such as chronic obstructive pulmonary disease (COPD), cystic fibrosis, and asthma. COPD is comprised primarily of two related diseases: chronic bronchitis and emphysema. In both diseases, there is chronic obstruction of the flow of air through the airways and out of the lungs, and the obstruction generally is permanent and progressive over time.

Asthma is a chronic disease of the airways of the lungs, characterized by inflammation and paradoxical narrowing of the bronchi. Asthma includes asthmatic conditions mediated via T-cell action, including extrinsic asthma (allergic asthma), intrinsic asthma (non-allergic asthma), mixed asthma (extrinsic and intrinsic asthma), occupational asthma induced by agents such as toluene diisocyanate, polyvinyl chloride, phthalic anhydride, trimellitic anhydride, plicatic acid (Western Red Cedar trees) or metal salts such as platinum or nickel), drug-induced asthma (including aspirin-induced asthma or asthma induced by non-steroidal anti-inflammatory drugs (NSAIDs)), exercise-induced asthma, and cough variant asthma. In some embodiments, the asthma is an allergic or non-allergic asthmatic condition mediated by T-cell function.

In some embodiments, disclosed herein are methods of treating asthma with an autotaxin inhibitor. In an asthmatic individual, the release of normal repair mediators, including LPA, is exaggerated or the actions of the repair mediators are inappropriately prolonged leading to inappropriate airway remodeling. Major structural features of the remodeled airway observed in asthma include a thickened lamina reticularis (the basement membrane-like structure just beneath the airway epithelial cells), increased numbers and activation of myofibroblasts, thickening of the smooth muscle layer, increased numbers of mucus glands and mucus secretions, and alterations in the connective tissue and capillary bed throughout the airway wall. In some embodiments, autotaxin and/or LPA contribute to these structural changes in the airway. In some embodiments, autotaxin and/or LPA are involved in acute airway hyperresponsiveness in asthma. The lumen of the remodeled asthmatic airway is narrower due to the thickening of the airway wall, thus decreasing airflow. In some embodiments, LPA contributes to the long-term structural remodeling and the acute hyperresponsiveness of the asthmatic airway. In some embodiments, LPA contributes to the hyper-responsiveness that is a primary feature of acute exacerbations of asthma.

In some embodiments, disclosed herein are methods of treating or preventing COPD with an autotaxin inhibitor. The term "chronic obstructive pulmonary disease (COPD)" refers to a group of lung diseases, including chronic bronchitis, emphysema and obliterative bronchiolitis. The most common of these diseases are chronic bronchitis and emphysema. Although a person with COPD may have either chronic bronchitis or emphysema, he or she will often have a mixture of the symptoms of these two conditions. Although emphysema usually results from damage to the lungs caused by environmental insult, usually as a result of long-term smoking, emphysema may also be caused by congenital absence of α1-antitrypsin in the lungs; this type of emphysema is usually inherited.

In some embodiments, disclosed herein are methods of treating chronic bronchitis with an autotaxin inhibitor. Chronic bronchitis (CB) is inflammation of one or more bronchi, usually secondary to infection, and is characterized by excessive production of mucus in the bronchi, accompanied by a recurrent cough which persists for at least three months of the year during at least two successive years. CB is the major non-asthmatic disease of the lung. Many different factors initiate CB, including cigarette smoking, environmental pollution, chronic infections and various genetic abnormalities. Of these factors, cigarette smoking is the most prevalent. Pathological changes in the lung include: (1) hypertrophy and hyperplasia of mucus-secreting glands in the bronchi, (2) increase in goblet cells, (3) disappearance or damage of cilia, and (4) chronic inflammatory changes and narrowing of small airways.

In some embodiments, disclosed herein are methods of treating emphysema with an autotaxin inhibitor. Emphysema is a lung condition which results from damage to the alveolar sacs in the lungs, usually caused by long-term smoking. This damage leads to a pathological accumulation of air in the tissues.

Administration of LPA in vivo induces airway hyperresponsiveness, itch-scratch responses, infiltration and activation of eosinophils and neutrophils, vascular remodeling, and nociceptive flexor responses. LPA also induces histamine release from mouse and rat mast cells. In an acute allergic reaction, histamine induces various responses, such as contraction of smooth muscle, plasma exudation, and mucus production. Plasma exudation is important in the airway, because the leakage and subsequent airway-wall edema contribute to the development of airway hyperresponsiveness. In some embodiments, disclosed herein are methods of reducing plasma exudation due to an acute allergic reaction with an autotaxin inhibitor.

Obesity

In some embodiments, disclosed herein are methods of treating obesity and/or diabetes with an autotaxin inhibitor.

Autotaxin is responsible for the lysoPLD activity released by adipocytes and exerts a paracrine control on preadipocyte growth via an LPA-dependent mechanism. In addition, autotaxin is up-regulated during adipocyte differentiation and in genetic obesity. In certain instances, autotaxin mRNA is up-regulated in adipocytes from db/db mice suggesting that the up-regulation of autotaxin is related to the severe type 2 diabetes phenotype and adipocyte insulin resistance. In some instances, up-regulation of autotaxin in adipocytes is associated with type 2 diabetes.

"Obesity," as used herein, refers to a medical condition in which excess body fat has accumulated to the extent that it may have an adverse effect on health, leading to increased health problems. In some embodiments, "obesity" refers to a weight increase, which is at least 5% of the total body weight. In some embodiments, disclosed herein are methods of treating postmenopausal obesity and/or visceral obesity with an autotaxin inhibitor.

Metabolic Disorders

In some embodiments, disclosed herein are methods of treating metabolic disorders, and conditions associated with metabolic disorders, comprising administering an autotaxin inhibitor. As used herein, a "metabolic disorder" refers to any pathological condition resulting from an alteration in a subject's metabolism. Such disorders include those resulting from an alteration in glucose homeostasis and/or insulin dysfunction. Metabolic disorders, include but are not limited to, metabolic syndrome, elevated blood glucose levels, insulin resistance, glucose intolerance, type 2 diabetes, type 1 diabetes, pre-diabetes, non-alcoholic fatty liver disease, nonalcoholic steatohepatitis, and obesity.

Metabolic disorders are inter-related and can result in disorders across various systems. Addressing the core metabolic disorder can reduce the severity of related conditions in a patient, including, for example, cardiovascular disorders (including, e.g., ischemic heart disease, angina and myocardial infarction, congestive heart failure, high blood pressure, abnormal cholesterol levels, deep vein thrombosis, and pulmonary embolism), neurological disorders (including, e.g., stroke, meralgia paresthetica, migraines, idiopathic, and intracranial hypertension, depression and social stigmatism), rheumatological and orthopedic disorders (including, e.g., gout, poor mobility, osteoarthritis, and lower back pain), dermatological disorders (including, e.g., stretch marks, acanthosis nigricans, lymphedema, cellulitis), gastrointestinal disorders (including, e.g., gastroesophageal reflux disease (GERD) and cholelithiasis (gallstones)), respiratory disorders (including, e.g., obstructive sleep apnea, obesity hypoventilation syndrome, asthma, and increased complications during general anaesthesia), urology and nephrology disorders (including, e.g., erectile dysfunction, urinary incontinence, chronic renal failure, and hypogonadism).

In some embodiments, described herein are methods for treating metabolic disorders. In some embodiments, administering an autotaxin inhibitor to an individual with a metabolic disorder has a variety of desirable outcomes which include, but are not limited to, reducing blood glucose levels, decreasing plasma lysophosphatidic acid levels, improving insulin sensitivity, increasing insulin secretion, improving glucose tolerance, and decreasing adipose tissue expansion. Any of these outcomes can treat, delay or prevent the onset of a metabolic disorder, wherein such metabolic disorders include, but are not limited to, metabolic syndrome, elevated blood glucose levels, insulin resistance, glucose intolerance, type 2 diabetes, type 1 diabetes, pre-diabetes, non-alcoholic fatty liver disease, nonalcoholic steatohepatitis, and obesity.

In some embodiments, described herein are methods of administering an autotaxin inhibitor for reducing fasting blood glucose levels in a mouse fed a high fat diet. A mouse fed a high fat diet, as illustrated herein, has higher fasting blood glucose levels than a mouse fed a normal diet. The administration of an autotaxin inhibitor to a mouse fed a high fat diet reduced fasting blood glucose levels thereby allowing fasting blood glucose levels to approach those levels observed in a mouse fed a normal diet.

In some embodiments, methods disclosed herein comprise administering an autotaxin inhibitor to a subject with elevated blood glucose levels. In some embodiments, the autotaxin inhibitor is used to treat an underlying metabolic disorder. In some embodiments, the metabolic disorder is treated by reducing blood glucose levels. In some embodiments, the subject is overweight or obese. In some embodiments, the subject has type 2 diabetes. In some embodiments, the subject has non-alcoholic fatty liver disease and/or nonalcoholic steatohepatitis. In some embodiments, the subject does not have a metabolic disorder. In some embodiments, the autotaxin inhibitor delays or prevents the onset of the metabolic disorder by reducing elevated blood glucose levels.

In some embodiments, methods disclosed herein comprise reducing plasma lysophosphatidic acid levels in an individual by administering an autotaxin inhibitor. In some embodiments, the plasma lysophosphatidic acid levels in the individual are elevated relative to a control. In some embodiments, the control is a person without a metabolic disorder. In some embodiments, the elevated plasma lysophosphatidic acid levels in the individual contribute to or increase the risk for developing a metabolic disorder.

In some embodiments, disclosed herein are methods comprising administering an autotaxin inhibitor to a subject with elevated plasma lysophosphatidic acid levels relative to a control. In some embodiments, disclosed herein are methods for improving insulin sensitivity comprising administering an autotaxin inhibitor to an individual sensitive to insulin. In some embodiments, disclosed herein are methods comprising the administration of an autotaxin inhibitor to a subject with insulin resistance. In some embodiments, disclosed herein are methods comprising the administration of an autotaxin inhibitor to improve insulin secretion in an individual. In some embodiments, disclosed herein are methods comprising the administration of an autotaxin inhibitor to improve glucose tolerance in an individual with impaired glucose tolerance. In some embodiments, disclosed herein are methods for decreasing adipose tissue expansion in a subject comprising administering to the subject an autotaxin inhibitor. In some embodiments, disclosed herein are methods for the treatment of a metabolic disorder in a subject that is overweight or obese comprising administering to the subject an autotaxin inhibitor.

Drug Induced Hyperglycemia

In some embodiments, disclosed herein are methods of treating drug induced hyperglycemia in a subject comprising administering to the subject an autotaxin inhibitor. In some embodiments, administration of an autotaxin inhibitor to a subject treats, prevents, or ameliorates the symptoms of drug induced hyperglycemia. In some embodiments, administration of an autotaxin inhibitor to a subject treats, prevents, or ameliorates the symptoms of drug induced hyperglycemia by reducing blood glucose levels. Pharmacological agents can affect glucose homeostasis that can result in hyperglycemia. In some embodiments, the hyperglycemia occurs in the absence of a diagnosis of diabetes. If left untreated, the elevated blood glucose levels can lead to a medical emergency. Symptoms include, but are not limited to fatigue, weakness, fruity odor of the breath, confusion, lack of concentration, shortness of breath, nausea, vomiting, dry skin, and flushing of the skin. Common drug categories that are associated with contributing to hyperglycemia include, but are not limited to: antibiotics, such as fluoroquinolones including gatifloxacin; beta-blockers, such as propranolol, metoprolol or atenolol; thiazide, such as hydrochlorothiazide, and thiazide-like diuretics, and thiazide-like drugs (metolazone); second-generation antipsychotics (SGAs) or "atypical antipsychotics" such as olanzapine or clozapine; corticosteroids; calcinuerin inhibitors such as cyclosporine, sirolimus or tarcrolimus; and protease inhibitors such as ritonavir.

Stress Induced Hyperglycemia

In some embodiments, disclosed herein are methods of treating stress induced hyperglycemia in a subject comprising administering to the subject an autotaxin inhibitor. In some embodiments, administration of an autotaxin inhibitor to a subject treats or prevents or delays the onset of stress induced hyperglycemia. In some embodiments, administration of an autotaxin inhibitor to a subject treats or prevents or delays the onset of stress induced hyperglycemia by reducing blood glucose levels. Stressed induced hyperglycemia (SIH) is a transient increase in plasma glucose levels higher than 200 mg/dL which occurs during an acute illness or injury. In some embodiments, the hyperglycemia occurs in the absence of a diagnosis of diabetes. The SIH results from an excess of glucose production relative glucose clearance. SIH has been associated with conditions including, but not limited to, myocardial infarction, stroke, and trauma. SIH has been associated with increase mortality and a higher incidence of congestive heart failure and cardiogenic shock in patients after myocardial infarction. Stroke victims have higher mortality associated with SIH and worse odds of desirable neurological outcomes as glucose levels increase with SIH. Hyperglycemia was also shown to be a predictor of infectious complications in the form of pneumonia, urinary tract infections, wound infections and bacteria. Overall, published studies have consistently shown higher morbidity and higher mortality rates in those patients that present with SIH.

Intraocular Pressure

In some embodiments, disclosed herein are methods of treating elevated intraocular pressure associated with glaucoma in a subject, the methods comprising administration of an autotaxin inhibitor to the subject.

Glaucoma is one of the leading causes of blindness and is characterized by elevated intraocular pressure (IOP). IOP is a primary risk factor for developing glaucoma and the risk of developing glaucoma decreases when IOP is reduced. Ocular hypotensive therapy is the mainstay of glaucoma treatment. Elevated IOP results from diminished aqueous humor (AH) drainage through the trabecular pathway and autotaxin activity is an abundant protein in human AH. Autotaxin is secreted by human trabecular meshwork cells and autotaxin activity is significantly elevated from glaucoma patients. Inhibition of autotaxin activity in AH by topical and intracameral delivery of a small molecule inhibitor leads to decreased IOP in rabbits.

Neuropathic Pain

In some embodiments, disclosed herein are methods of treating neuropathic pain with an autotaxin inhibitor.

LPA induces neuropathic pain as well as demyelination and pain-related protein expression changes via LPA1. In some instances, autotaxin heterozygous knockout mice show about 50% recovery of nerve injury-induced neuropathic pain compared to wild type mice. Lysophosphatidylcholine (LPC), is known to induce neuropathic pain. In certain instances, LPC-induced neuropathic pain is partially reduced in autotaxin heterozygous knockout mice.

Neuropathic pain results from injury to a nerve. In contrast to immediate pain caused by tissue injury, in some embodiments, neuropathic pain develops days or months after a traumatic injury. In addition, neuropathic pain frequently is long-lasting or chronic and can occur spontaneously or as a result of stimulation that normally is not painful.

Autotaxin Inhibitor Compounds

In some embodiments, the autotaxin inhibitor contemplated for use in any of the embodiments described herein is a small molecule inhibitor.

In some embodiments, the autotaxin inhibitor is a small molecule inhibitor that is characterized as having one or more of the following properties:

a molecular weight of at most 700 capability of at least 50% inhibition (at 1 micromolar) of autotaxin conversion of lysophosphatidyl choline to lysophosphatidic acid in a suitable in vitro assay that measures such activity selective inhibition of autotaxin activity suitable for administration to human at therapeutically relevant doses with at least 50% inhibition of autotaxin at trough In some embodiments, the autotaxin inhibitor has the structure of Compound A:

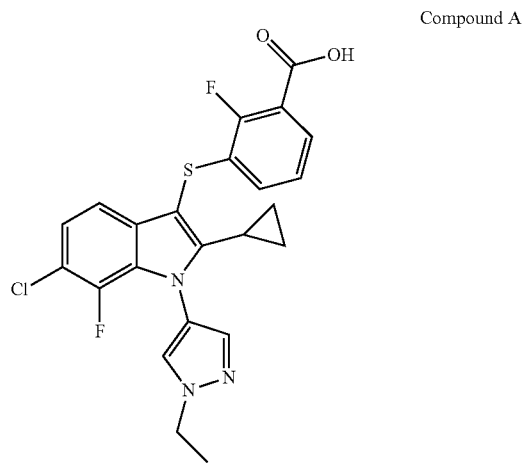 [SMILES: CCn1cc(-n2c(C3CC3)c(Sc3cccc(C(=O)O)c3F)c3ccc(Cl)c(F)c32)cn1]

Compound A

In some embodiments, Compound A is used as the free acid. In some embodiments, Compound A is used as a pharmaceutically acceptable salt. In some embodiments, Compound A is used as the sodium salt.

In some embodiments, the autotaxin inhibitor has the structure of Compound B:

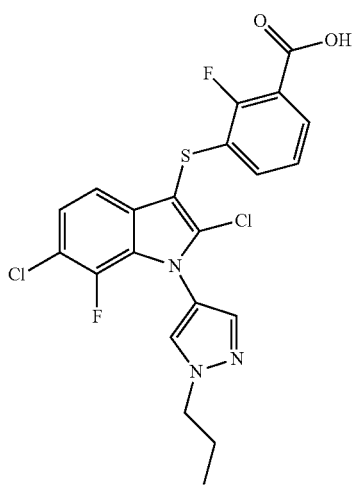

Compound B

In some embodiments, Compound B is used as the free acid. In some embodiments, Compound B is used as a pharmaceutically acceptable salt. In some embodiments, Compound B is used as the sodium salt.

In some embodiments, the autotaxin inhibitor has the structure of Compound C:

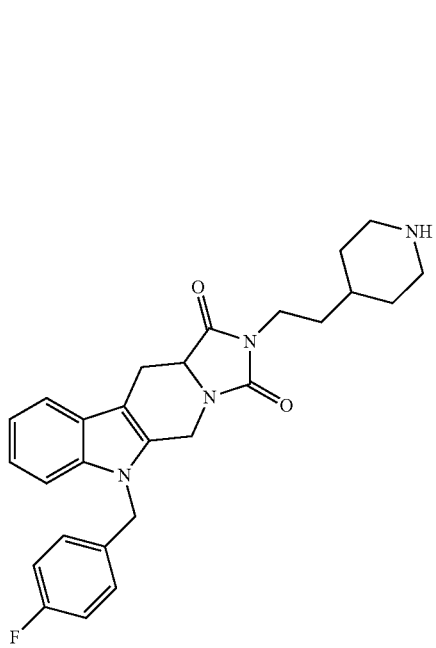

Compound C

In some embodiments, Compound C is used as the free amine. In some embodiments, Compound C is used as a pharmaceutically acceptable salt. In some embodiments, Compound C is used as the hydrochloride salt.

In some embodiments, the autotaxin inhibitor has the structure of Compound D:

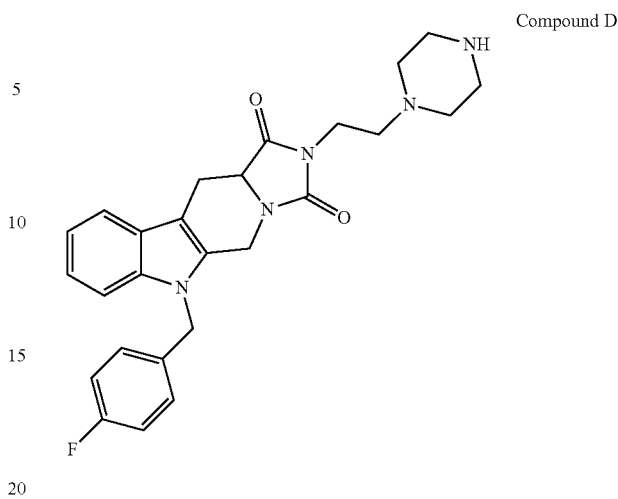

Compound D

In some embodiments, Compound D is used as the free amine. In some embodiments, Compound D is used as a pharmaceutically acceptable salt. In some embodiments, Compound D is used as the hydrochloride salt.

Additional autotaxin inhibitors include compounds with the following structure:

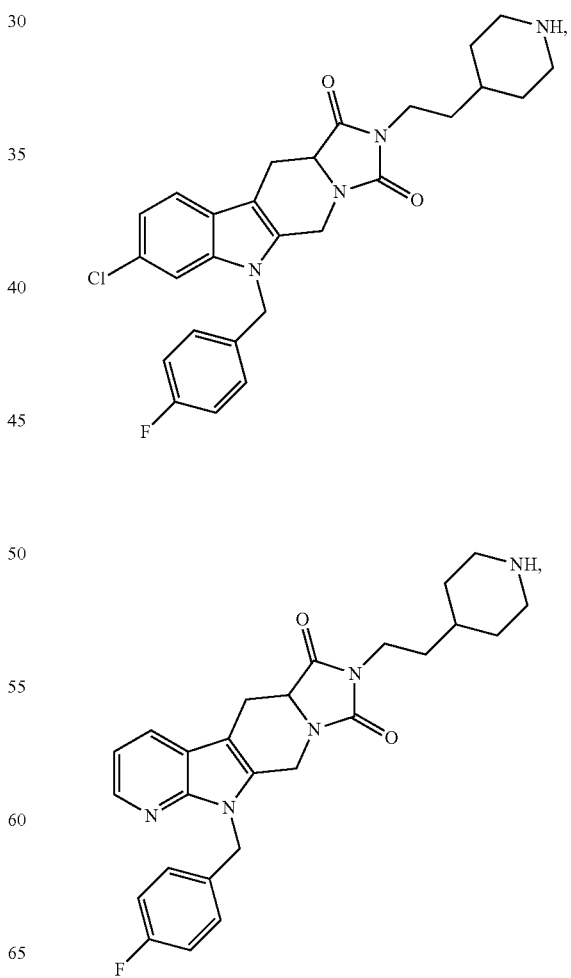

35
-continued

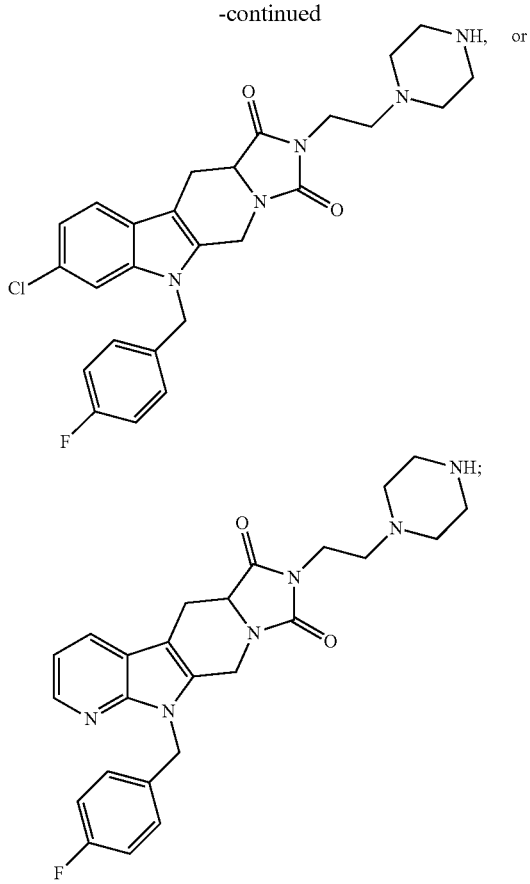

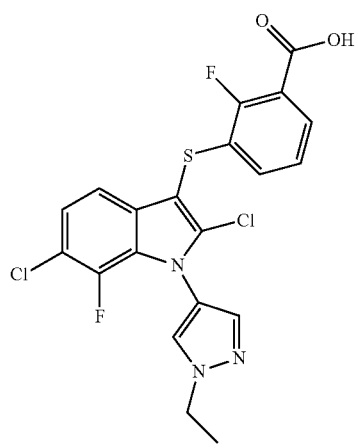

or a pharmaceutically salt thereof.

In some embodiments, the 4-fluorobenzyl group of any the preceding compounds is replaced with 4-chlorobenzyl; 3-chlorobenzyl; 3-fluorobenzyl; 3,5-difluorobenzyl, 2,4-difluorobenzyl; 3,5-dichlorobenzyl; 2-chloropyridin-5-ylmethyl; 2-methoxypyridin-5-ylmethyl; 2-trifluoromethylthiazol-5-ylmethyl; phenylprop-3-yl; thien-2-ylmethyl; or 5-chlorothien-2-ylmethyl.

In some embodiments, the autotaxin inhibitor has the structure of Compound E:

Compound E

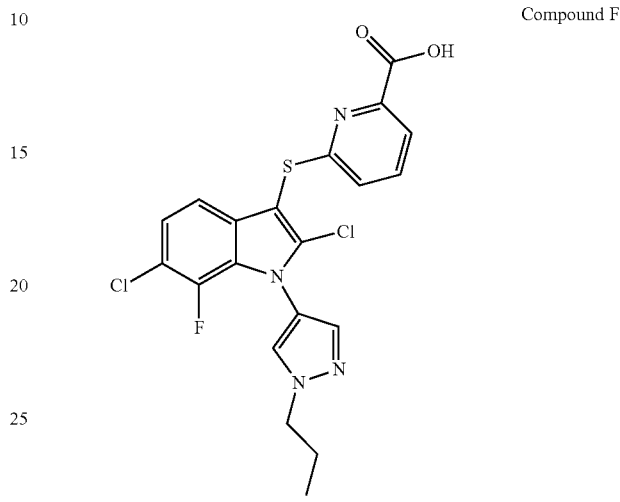

In some embodiments, Compound E is used as the free acid. In some embodiments, Compound E is used as a pharmaceutically acceptable salt. In some embodiments, Compound E is used as the sodium salt.

In some embodiments, the autotaxin inhibitor has the structure of Compound F:

Compound F

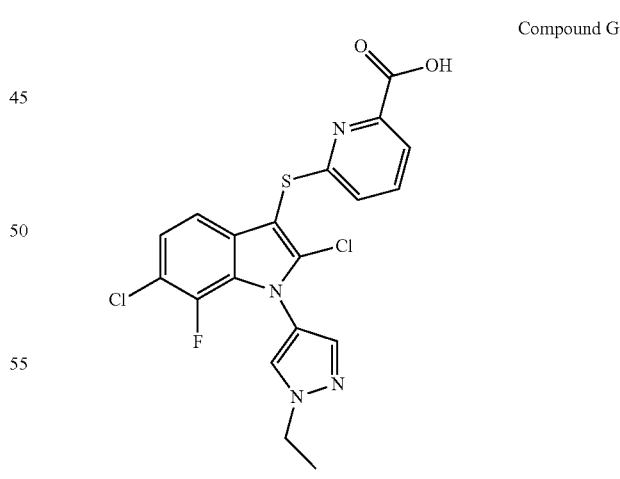

In some embodiments, Compound F is used as the free acid. In some embodiments, Compound F is used as a pharmaceutically acceptable salt. In some embodiments, Compound F is used as the sodium salt.

In some embodiments, the autotaxin inhibitor has the structure of Compound G:

Compound G

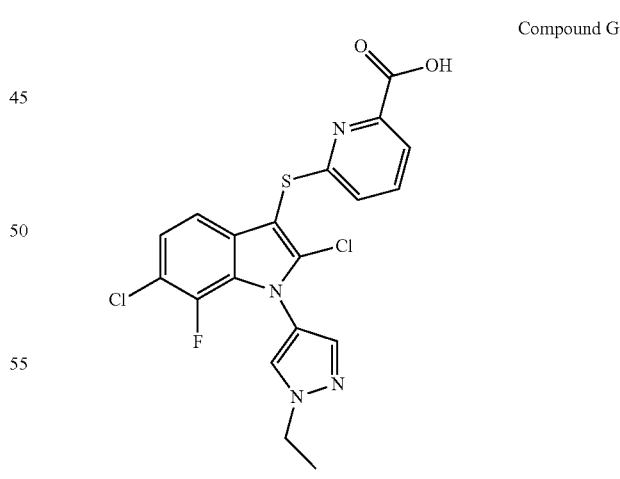

In some embodiments, Compound G is used as the free acid. In some embodiments, Compound G is used as a pharmaceutically acceptable salt. In some embodiments, Compound G is used as the sodium salt.

In some embodiments, the autotaxin inhibitor has the structure of Compound H:

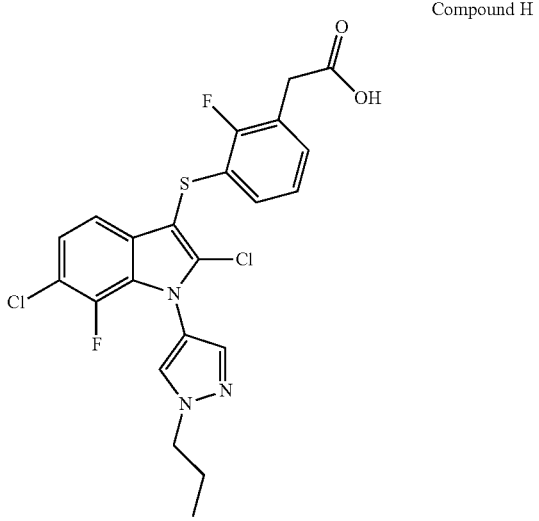 [SMILES: CCCn1cc(-n2c(Cl)c(Sc3cccc(CC(=O)O)c3F)c3ccc(Cl)c(F)c32)cn1]

Compound H

In some embodiments, Compound H is used as the free acid. In some embodiments, Compound H is used as a pharmaceutically acceptable salt. In some embodiments, Compound H is used as the sodium salt.

In some embodiments, the autotaxin inhibitor has the structure of Compound I:

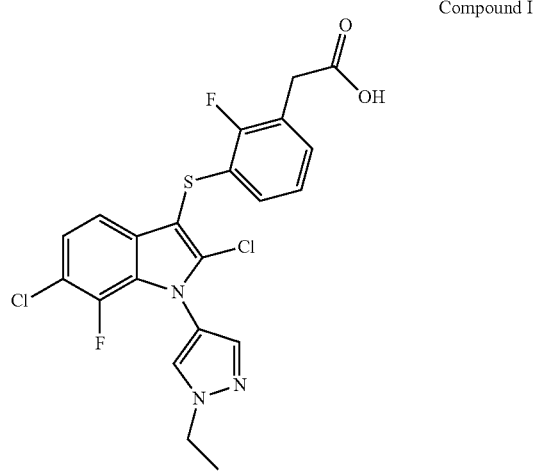 [SMILES: CCn1cc(-n2c(Cl)c(Sc3cccc(CC(=O)O)c3F)c3ccc(Cl)c(F)c32)cn1]

Compound I

In some embodiments, Compound I is used as the free acid. In some embodiments, Compound I is used as a pharmaceutically acceptable salt. In some embodiments, Compound I is used as the sodium salt.

In some embodiments, the autotaxin inhibitor for use in any of the embodiments described herein is a compound described in international patent application no. PCT/US2014/066706 filed Nov. 20, 2014, published as WO/2015/077503, which is herein incorporated by reference for such compounds.

In some embodiments, the autotaxin inhibitor for use in any of the embodiments described herein is a compound described in international patent application no. PCT/US2014/066705 filed Nov. 20, 2014, published as WO/2015/077502, which is herein incorporated by reference for such compounds.

In one aspect, autotaxin inhibitors are in the form of pharmaceutically acceptable salts. As well, active metabolites of these compounds having the same type of activity are included in the scope of the present disclosure. In addition, the autotaxin inhibitors can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting an autotaxin inhibitor with an acid. In some embodiments, the autotaxin inhibitor (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, an autotaxin inhibitor is prepared as a chloride salt, sulfate salt, bromide salt, mesylate salt, maleate salt, citrate salt or phosphate salt. In some embodiments, an autotaxin inhibitor is prepared as a hydrochloride salt.

In some embodiments, pharmaceutically acceptable salts are obtained by reacting an autotaxin inhibitor with a base. In some embodiments, the autotaxin inhibitor is acidic and is reacted with a base. In such situations, an acidic proton of the autotaxin inhibitor is replaced by a metal ion, e.g., lithium, sodium, potassium, magnesium, calcium, or an aluminum ion. In some cases, autotaxin inhibitors coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, autotaxin inhibitors form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt. In some embodiments, the compounds provided herein are prepared as a sodium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of autotaxin inhibitors are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of autotaxin inhibitors, as well as active metabolites of these compounds having the same type of activity.

In some embodiments, sites on the organic radicals (e.g. alkyl groups, aromatic rings) of autotaxin inhibitors are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the autotaxin inhibitors are labeled isotopically (e.g. with a radioisotope) or by another other means, including, but not limited to, the use of chromophores or fluorescent moieties, bioluminescent labels, or chemiluminescent labels.

Autotaxin inhibitors include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled autotaxin inhibitors, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the autotaxin inhibitors possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, autotaxin inhibitors are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the autotaxin inhibitors. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, autotaxin inhibitors are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is an autotaxin inhibitor, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the autotaxin inhibitors include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, autotaxin inhibitors are prepared as alkyl ester prodrugs.

Prodrug forms of the herein described compounds, wherein the prodrug is metabolized in vivo to produce an autotaxin inhibitor as set forth herein are included within the scope of the claims. In some cases, some of the herein-described compounds is a prodrug for another derivative or active compound.

In additional or further embodiments, the autotaxin inhibitors are metabolized upon administration to an organism in need to produce a metabolite that is then used to produce a desired effect, including a desired therapeutic effect.

A "metabolite" of an autotaxin inhibitor is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. an autotaxin inhibitor, or a pharmaceutically acceptable salt thereof, and a co-agent, are both administered to a patient simultaneously in the form of a single entity or dosage. The term "non-fixed combination" means that the active ingredients, e.g. an autotaxin inhibitor, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Autotaxin Inhibition

Provided herein, in various aspects, are methods for the prevention or treatment of a disease, disorder or condition in a subject that would benefit from the inhibition or reduction of autotaxin activity comprising administering to the subject an autotaxin inhibitor. In some embodiments, provided herein are methods for reducing plasma autotaxin activity in a subject in need thereof, comprising administering a therapeutically effective amount of an autotaxin inhibitor to the subject in need thereof. In some embodiments, the subject in need thereof is suffereing from a disease, disorder or condition associated with autotaxin activity. Non-limiting examples of diseases, disorders and conditions are described herein.

In some embodiments, described herein are methods for the treatment of one or more conditions, diseases, and/or disorders in a human comprising administering an autotaxin inhibitor, wherein in the autottaxin inhibitor is suitable for administration to a human at therapeutically relevant doses with at least 50% inhibition of autotaxin at trough.

In some embodiments, described herein are methods for the treatment of one or more conditions, diseases, and/or disorders in a subject, the method comprising the administration of a non-competitive autotaxin inhibitor. Non-limiting examples of non-competitive autotaxin inhibitors include Compound A and Compound B.

In some embodiments, described herein are methods for the treatment of one or more conditions, diseases and/or disorders in a subject comprising the administration of an autotaxin inhibitor to the subject, wherein the autotaxin inhibitor has an in vitro autotaxin inhibition $IC_{50}$ of less than about 100 nM, 50 nM, 40 nM, 30 nM, 20 nM or 10 nM. In some examples, an in vitro autotaxin inhibition assay includes an assay described as described in the Examples.

In some embodiments, described herein are methods for the treatment of one or more conditions, diseases, and/or disorders in a subject, the method comprising the administration of an autotaxin inhibitor, wherein the autotaxin inhibitor preferentially inhibits autotaxin acitivity as compared to ENPP1, ENPP3, ENPP6, and/or ENPP7. In some embodiments, an autotaxin inhibitor useful in the methods of treatment described herein has an $IC_{50}$ for the inhibition of ENPP1, ENPP3, ENPP6, or ENPP7 greater than about 10, 20, or 100 μM in an in vitro assay that measures such activity. In on such in vitro assay, Compound A and Compound B exhibited an $IC_{50}$ greater than 10 μM for ENPP 1, 3, 6, and 7.

In some embodiments, described herein are methods for the treatment of one or more conditions, diseases, and/or disorders in a subject, the method comprising the administration of an autotaxin inhibitor, wherein the autotaxin inhibitor is at least 80%, 90%, 95%, 96%, 97%, 98%, or 99% bound to plasma.

In some embodiments, described herein are methods for the prevention or treatment of one or more conditions, diseases, and/or disorders in a subject, the method comprising the administration of an autotaxin inhibitor, wherein the autotaxin inhibitor cause acute or chronic liver toxicity. In some embodiments, liver toxicity can be assessed in suitable in vivo assays. In some embodiments, liver toxicity is assessed by monitoring any increases in the levels of liver markers ALT, AST, AlkP and bilirubin. For example, in a suitable dog liver toxicity study, Compound A exhibited undesired elevated liver markers whereas Compound B did not exhibit the same effects. In some embodiments, no increases in liver markers ALT, AST, AlkP and bilirubin were observed for Compound B when dosed at 100 mpk for 5 days.

Pharmaceutical Compositions

In some embodiments, the autotaxin inhibitors are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the autotaxin inhibitors are administered either alone or in combination with pharmaceutically acceptable carriers, excipients or diluents, in a pharmaceutical composition. Administration of the autotaxin inhibitors and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, autotaxin inhibitors can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of an autotaxin inhibitor of the present invention externally to the epidermis or the buccal cavity and the instillation of such an autotaxin inhibitor into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the autotaxin inhibitors and compositions described herein may include other agents conventional in the art having regard to the type of formulation in question, for example those suitable for oral administration may include flavoring agents.

Methods of Dosing and Treatment Regimens

In one embodiment, the autotaxin inhibitors, or a pharmaceutically acceptable salt thereof, are used in the preparation of medicaments for the treatment of diseases or conditions in a mammal that would benefit from inhibition or reduction of autotaxin activity. Methods for treating any of the diseases or conditions described herein in a mammal in need of such treatment, involves administration of pharmaceutical compositions that include at least one autotaxin inhibitor or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the autotaxin inhibitors are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising an autotaxin inhibitor, or a pharmaceutically acceptable salt thereof, in order to prevent a return of the symptoms of the disease or condition.

In certain embodiments wherein the patient's condition does not improve, upon the doctor's discretion the administration of autotaxin inhibitors are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular autotaxin inhibitor, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the autotaxin inhibitor, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the autotaxin inhibitor used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the autotaxin inhibitors lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the autotaxin inhibitor, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the autotaxin inhibitor, including further embodiments in which (i) the autotaxin inhibitor is administered once a day; or (ii) the autotaxin inhibitor is administered to the mammal multiple times over the span of one day.

In any of the aforementioned aspects are further embodiments comprising multiple administrations of the effective amount of the autotaxin inhibitor, including further embodiments in which (i) the autotaxin inhibitor is administered continuously or intermittently: as in a single dose; (ii) the time between multiple administrations is every 6 hours; (iii) the autotaxin inhibitor is administered to the mammal every 8 hours; (iv) the autotaxin inhibitor is administered to the mammal every 12 hours; (v) the autotaxin inhibitor is administered to the mammal every 24 hours. In further or alternative embodiments, the method comprises a drug holiday, wherein the administration of the autotaxin inhibitor is temporarily suspended or the dose of the autotaxin inhibitor being administered is temporarily reduced; at the end of the drug holiday, dosing of the autotaxin inhibitor is resumed. In one embodiment, the length of the drug holiday varies from 2 days to 1 year.

In some embodiments, administration of a therapeutically effective dose of an autotaxin inhibitor does not cause hepatobiliary damage. In some embodiments, administration of an autotaxin inhibitor does not cause an increase or does not cause a significant increase in serum levels of one or more liver proteins. Liver proteins include, without limitation, aspartate transaminase (AST), bilirubin, and alkaline phosphatase (ALP). As an example, a significant increase is an increase of at least about 50%, 100%, 200% or higher of serum protein levels after administration of a prophylactic or therapeutic dose of an autotaxin inhibitor as compared to serum protein levels prior to autotaxin inhibitor administration. Measurement of liver enzymes after administration includes the measurement of liver enzymes after completion of a therapeutic regimen. Measurement of liver enzymes after administration includes the measurement of liver enzymes during the course of a therapeutic regimen.

In some embodiments, administration of a therapeutically effect dose of an autotaxin inhibitor does not cause an elevation in serum aspartate transaminase (AST) levels as compared to serum AST levels prior to the administration. In some embodiments, administration of a therapeutically effective dose of an autotaxin inhibitor causes less than a 10-fold, 5-fold, 3-fold, or 2-fold increase in serum AST levels as compared to serum AST levels prior to the administration. In some embodiments, following administration of a therapeutically effective dose of an autotaxin inhibitor to a subject, serum AST levels of the subject are between about 8 and about 200 U/L, between about 8 and 100 U/L, between about 8 and 80 U/L or between about 8 and 60 U/L.

In some embodiments, administration of a therapeutically effective dose of an autotaxin inhibitor to a subject does not cause an elevation in bilirubin levels in the subject as compared to bilirubin levels prior to the administration. In some embodiments, the bilirubin levels are not significantly increased within 1 or more days, weeks, months or years after initial administration of an autotaxin inhibitor. A significant increase includes, at least a 2-fold, 3-fold, 4-fold, or 5-fold increase in bilirubin level after administration of an autotaxin inhibitor.

In some embodiments, administration of a therapeutically effective dose of an autotaxin inhibitor to a subject does not cause an elevation in alkaline phosphatase (ALP) levels in the subject as compared to ALP levels prior to the administration. In some embodiments, the ALP level is not significantly increased within 1 or more days, weeks, months or years after initial administration of an autotaxin inhibitor. A significant increase includes, at least a 2-fold, 3-fold, 4-fold, or 5-fold increase in ALP level after administration of an autotaxin inhibitor.

In some embodiments, administration of a therapeutically effective dose of an autotaxin inhibitor to a subject does not cause an increase in bile staining in a liver sample from the subject as compared to bile staining prior to the administration. In some embodiments, bile staining is not significantly increased within 1 or more days, weeks, months or years after initial administration of an ATX inhibitor.

In some embodiments, following the administration of a therapeutically effective dose of an autotaxin inhibitor to a subject, the no observed adverse effect level (NOAEL) is at least 1, 10, 20, 50, 100, 500 or 1000 milligrams of autotaxin inhibitor per kilogram of body weight (mpk). In some examples, the 7-day NOAEL for a rat administered an autotaxin inhibitor is at least about 200, 300, 400, 500, 600, 700, 800, 900, 1000, 1500 or 2000 mpk. In some examples, the 7-day NOAEL for a dog administered an autotaxin inhibitor is at least about 10, 20, 30, 40, 50, 60, 70, 80, 90, 100, 200, 500 mpk. In some examples, the 5-day NOAEL for a dog administered an autotaxin inhibitor is at least about 10, 20, 30, 40, 50, 60, 70, 80, 90, 100, 200, 500 mpk.

Combination Treatments

In certain instances, it is appropriate to administer at least one autotaxin inhibitor, or a pharmaceutically acceptable salt thereof, in combination with one or more other therapeutic agents. In embodiments, the pharmaceutical composition further comprises one or more anti-cancer agents.

In one embodiment, the therapeutic effectiveness of one of the autotaxin inhibitors is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the autotaxin inhibitors with another agent (which also includes a therapeutic regimen) that also has therapeutic benefit.

In one specific embodiment, an autotaxin inhibitor, or a pharmaceutically acceptable salt thereof, is co-administered with a second therapeutic agent, wherein the autotaxin inhibitor, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

In certain embodiments, different therapeutically-effective dosages of autotaxin inhibitors will be utilized in formulating pharmaceutical composition and/or in treatment regimens when the autotaxin inhibitors are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of an autotaxin inhibitor, or a pharmaceutically acceptable salt thereof, is initiated prior to, during, or after treatment with a second agent described herein, and continues until any time during treatment with the second agent or after termination of treatment with the second agent. It also includes treatments in which an autotaxin inhibitor, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the autotaxin inhibitor is administered either simultaneously with the one or more other therapeutic agents, or sequentially.

In combination therapies, the multiple therapeutic agents (one of which is one of the autotaxin inhibitors) are administered in any order or even simultaneously. If administration is simultaneous, the multiple therapeutic agents are, by way of example only, provided in a single, unified form, or in multiple forms (e.g., as a single pill or as two separate pills).

The autotaxin inhibitors, or a pharmaceutically acceptable salt thereof, as well as combination therapies, are administered before, during or after the occurrence of a disease or condition, and the timing of administering the composition containing an autotaxin inhibitor varies. Thus, in one embodiment, the autotaxin inhibitors are used as a prophylactic and are administered continuously to subjects with a propensity to develop conditions or diseases in order to prevent the occurrence of the disease or condition. In another embodiment, the autotaxin inhibitors and compositions are administered to a subject during or as soon as possible after the onset of the symptoms. In specific embodiments, an autotaxin inhibitor is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, an autotaxin inhibitor or a formulation containing the autotaxin inhibitor is administered for at least 2 weeks, about 1 month to about 5 years.

Exemplary Agents for use in Combination Therapy

In some embodiments, an autotaxin inhibitor, or a pharmaceutically acceptable salt thereof, is administered in combination with chemotherapy, hormone blocking therapy, radiation therapy, monoclonal antibodies, or combinations thereof.

In certain embodiments, the at least one additional therapy is administered at the same time as the autotaxin inhibitor. In certain embodiments, the at least one additional therapy is administered less frequently than the autotaxin inhibitor. In certain embodiments, the at least one additional therapy is administered more frequently than the autotaxin inhibitor. In certain embodiments, the at least one additional therapy is administered prior to administration of the autotaxin inhibitor. In certain embodiments, the at least one additional therapy is administered after administration of the autotaxin inhibitor.

Hormone blocking therapy includes the use of agents that block the production of estrogens or block the estrogen receptors. In some embodiments, hormone blocking therapy includes the use of estrogen receptor modulators and/or aromatase inhibitors. Estrogen receptor modulators include triphenylethylene derivatives (e.g. tamoxifen, toremifene, droloxifene, 3-hydroxytamoxifen, idoxifene, TAT-59 (a phosphorylated derivative of 4-hydroxytamoxifen) and GW5638 (a carboxylic acid derivative of tamoxifen)); non-steroidal estrogen receptor modulators (e.g. raloxifene, LY353381 (SERM3) and LY357489); steroidal estrogen receptor modulators (e.g. ICI-182,780). Aromatase inhibitors include steroidal aromatase inhibitors and non-steroidal aromatase inhibitors. Steroidal aromatase inhibitors include, but are not limited to, such exemestane. Non-steroidal aromatase inhibitors include, but are not limited to, as anastrozole, and letrozole.

Chemotherapy includes the use of anti-cancer agents.

In some embodiments, anti-cancer agents for use in combination with an autotaxin inhibitor, or a pharmaceutically acceptable salt thereof, include one or more of the following: abiraterone; abarelix; abraxane, adriamycin; actinomycin; acivicin; aclarubicin; acodazole hydrochloride; acronine; adozelesin; aldesleukin; alemtuzumab; allopurinol; alitretinoin; altretamine; ametantrone acetate; aminoglutethimide; aminolevulinic acid; amifostine; amsacrine; anastrozole; anthramycin; aprepitant; arsenic trioxide; asparaginase; asperlin; azacitidine; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; brequinar sodium; bropirimine; busulfan; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; flurocitabine; fosquidone; fostriecin sodium; fulvestrant; gefitinib; gemcitabine; gemcitabine hydrochloride; gemcitabine—cisplatin; gemtuzumab ozogamicin; goserelin acetate; histrelin acetate; hydroxyurea; idarubicin hydrochloride; ifosfamide; iimofosine; ibritumomab tiuxetan; idarubicin; ifosfamide; imatinib mesylate; imiquimod; interleukin II (including recombinant interleukin II, or r1L2), interferon alfa-2a; interferon alfa-2b; interferon alfa-n1; interferon alfa-n3; interferon beta-1 a; interferon gamma-1 b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; mycophenolic acid; nandrolone phenpropionate; nelarabine; nilotinib; nocodazoie; nofetumomab; nogalamycin; ofatumumab; oprelvekin; ormaplatin; oxaliplatin; oxisuran; paclitaxel; palifermin; palonosetron hydrochloride;

pamidronate; pegfilgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; pomalidomide, porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; sargramostim; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab and $I^{131}$ Iodine tositumomab; trastuzumab; trestolone acetate; tretinoin; triciribine phosphate; trimetrexate; trimetrexate glucuronate; triptorelin; tubulozole hydrochloride; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; and zorubicin hydrochloride.

Monoclonal antibodies include, but are not limited to, trastuzumab (Herceptin) and rituximab (Rituxan).

In some embodiments, the at least one additional chemotherapeutic agent is selected from, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In one aspect, the autotaxin inhibitor, or a pharmaceutically acceptable salt thereof, is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, carfilzomib, trastuzumab, BAY 11-7082, PKC412, or PD184352, paclitaxel, and analogs of paclitaxel. Compounds that have the basic taxane skeleton as a common structure feature, have also been shown to have the ability to arrest cells in the G2-M phases due to stabilized microtubules and are optionally useful for treating cancer in combination with the autotaxin inhibitors.

Further examples of anti-cancer agents for use in combination with an autotaxin inhibitor, or a pharmaceutically acceptable salt thereof, include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; activin inhibitors, PKM2 inhibitors, c-fms inhibitors and histone deacetylase inhibitors. Further examples of anti-cancer agents for use in combination with an autotaxin inhibitor, or a pharmaceutically acceptable salt thereof, include aromatase inhibitors. Aromatase inhibitors include steroidal aromatase inhibitors and non-steroidal aromatase inhibitors. Steroidal aromatase inhibitors include, but are not limited to, exemestane. Non-steroidal aromatase inhibitors include, but are not limited to, anastrozole, and letrozole.

Yet other anticancer agents for use in combination with an autotaxin inhibitor, or a pharmaceutically acceptable salt thereof, include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with an autotaxin inhibitor, or a pharmaceutically acceptable salt thereof, include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with an autotaxin inhibitor, or a pharmaceutically acceptable salt thereof, include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.).

In some embodiments, an autotaxin inhibitor, or a pharmaceutically acceptable salt thereof, is used to treat cancer in combination with: an antiestrogen (e.g., tamoxifen), an antiandrogen (e.g., bicalutamide, flutamide), a gonadotropin releasing hormone analog (e.g., leuprolide).

Other agents that are optionally used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules include without limitation the following marketed drugs and drugs in development: Erbulozole, Dolastatin 10, Mivobulin isethionate, Vincristine, NSC-639829, Discodermolide, ABT-751, Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride, Epothilones (such as Epothilone A, Epothilone B, Epothilone C, Epothilone D, Epothilone E, Epothilone F, Epothilone B N-oxide, Epothilone A N-oxide, 16-aza-epothilone B, 21-aminoepothilone B, 21-hydroxyepothilone D, 26-fluoroepothilone, Auristatin PE, Soblidotin, Vincristine sulfate, Cryptophycin 52, Vitilevuamide, Tubulysin A, Canadensol, Centaureidin, Oncocidin A1 Fijianolide B, Laulimalide, Narcosine, Nascapine, Hemiasterlin, Vanadocene acetylacetonate, Indanocine Eleutherobins (such as Desmethyleleutherobin, Desaetyleleutherobin, lsoeleutherobin A, and Z-Eleutherobin), Caribaeoside, Caribaeolin, Halichondrin B, Diazonamide A, Taccalonolide A, Diozostatin, (−)-Phenylahistin, Myoseverin B, Resverastatin phosphate sodium.

In one aspect, an autotaxin inhibitor, or a pharmaceutically acceptable salt thereof, is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, an autotaxin inhibitor, or a pharmaceutically acceptable salt thereof, is used in combination with anti-emetic agents to treat nausea or emesis, which result from the use of an autotaxin inhibitor, or a pharmaceutically acceptable salt thereof, anti-cancer agent(s) and/or radiation therapy.

Anti-emetic agents include, but are not limited to: neurokinin-1 receptor antagonists, 5HT3 receptor antagonists (such as ondansetron, granisetron, tropisetron, palonosetron, and zatisetron), $GABA_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In some embodiments, an autotaxin inhibitor, or a pharmaceutically acceptable salt thereof, is used in combination with an agent useful in the treatment of anemia. Such an anemia treatment agent is, for example, a continuous eythropoiesis receptor activator (such as epoetin-α).

In some embodiments, an autotaxin inhibitor, or a pharmaceutically acceptable salt thereof, is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In one aspect, an autotaxin inhibitor, or a pharmaceutically acceptable salt thereof, is administered in combination with one or more immunosuppressants. Immunosuppressive therapy is clinically used to treat or prevent the rejection of transplanted organs and tissues (e.g. bone marrow, heart, kidney, liver); treatment of autoimmune diseases or diseases that are most likely of autoimmune origin (e.g. rheumatoid arthritis, myasthenia gravis, systemic lupus erythematosus, Crohn's disease, and ulcerative colitis); and treatment of some other non-autoimmune inflammatory diseases (e.g. long term allergic asthma control), and in the treatment of fibrotic conditions. Immunosuppressants include, without limitation, glucocorticoids, cytostatics, antibodies and drugs that act on immunophilins. Examples of glucocorticoids include cortisol, cortisone, prednisone, prednisolone, methylprednisolone, dexamethasone, betamethasone, triamcinolone, beclometasone, fludrocortisone, deoxycorticosterone, and aldosterone. Examples of cytostatics include alkylating agents (e.g., nitrogen mustards such as cyclophosphamide, nitrosoureas, platinum compounds) and antimetabolites (e.g., folic acid analogues such as methotrexate, purine analogues such as azathioprine and mercaptopurine, pyrimidine analogues such as fluorouracil, protein synthesis inhibitors). Examples of drugs for use in the methods described include ciclosporin, tacrolimus, sirolimus, interferons, opioids, TNF binding proteins, mycophenolate, and fingolimod. Examples of antibodies useful for co-administration with an autotaxin inhibitor in a method described herein include Antithymocyte globulin, 1D09C3, Adalimumab/D2E7 (Humira; Trudexa), Afelimomab, Afutuzumab/GA101 (type II), Alemtuzumab/Campath-1H (MabCampath), Apolizumab/Hu1D10, Aselizumab, Atlizumab, Basiliximab (Simulect), Bectumomab/IMMU-LL2, Belimumab (Benlysta, LymphoStat-B), Bertilimumab, BL22/CAT-3888, Brentuximab/cAC10/SGN-35, Briakinumab/ABT-874, Canakinumab/ACZ885 (Ilaris), Certolizumab pegol/CDP870 (Cimzia), Clenoliximab, Dacetuzumab/SGN-40, Daclizumab (Zenapax), Eculizumab/5G1.1 (Soliris), Efalizumab (Raptiva, formerly Xanelim), Epratuzumab/hLL2/IMMU-102 (Lymphocyde©), Fontolizumab, Fresolimumab/GC-1008, Galiximab/IDEC-114, Gavilimomab/ABX-CBL, Gemtuzumab, Golimumab/CNTO148 (Simponi), HL2434P (IMMU-114), Ibritumomab tiuxetan (MXDPTA)/IDEC Y2B8 (Zevalin), Infliximab/chimeric A2 (cA2) (Remicade), Inolimomab/BT563, Inotuzumab, Keliximab/IDEC CE9.1, Lerdelimumab/CAT-152, Lintuzumab/HuM195 (Zamyl), LMB-2, Lorvotuzumab mertansine, Lumiliximab/IDEC-152, Lym-1 (Oncolym), MDX-060, Mepolizumab/SB-240563, Metelimumab/CAT-192, Mogamulizumab/KW-0761/AMG-761, Moxetumomab pasudotox/CAT-8015/HA22, Muromonab-CD3 (Orthoclone OKT3), Natalizumab (Tysabri, Antegren), Nerelimomab/CDP571, Ocrelizumab/PRO70769 (type I), Odulimomab, Ofatumumab/2F2/HuMax-CD20 (Arzerra) (type I), Omalizumab (Xolair), Otelixizumab/TRX4, Pascolizumab/SB 240683, Reslizumab/SCH 55700 (Cinquil), Rituximab/chimeric 2B8 (IDEC-C2B8) (Rituxan, MabThera) (type I), Ruplizumab (Antova), SAR-3419, Secukinumab/AIN-457, SGN30, Siplizumab/MEDI-507, Teplizumab/MGA031/hOKT3γ1 (Ala-Ala), Tocilizumab (Actemra), Tositumomab (type II), Ustekinumab/CNTO 1275 (Stelara), Vedolizumab/MNL-0002, Veltuzumab/IMMU-106/hA20 (type I), Visilizumab (Nuvion), Zanolimumab/HuMax-CD4, Zolimomab aritox/H65, Abatacept/CTLA4-Ig/BMS-188667 (Orencia), Belatacept/LEA29Y, Atacicept/BLyS/APRIL-Ig, Etanercept/TNFR-Ig (Enbrel), Pegsunercept/pegylated TNFR-Ig, Alefacept (Amevive), and Rilonacept (Arcalyst). Immunosuppressive antibodies include antibodies that target complement-dependent proteins and interleukins.

In some embodiments, an autotaxin inhibitor, or a pharmaceutically acceptable salt thereof, is administered with a corticosteroid. In some embodiments, an autotaxin inhibitor, or a pharmaceutically acceptable salt thereof, is administered with an a therapeutic agent selected from among: Calcineurin inhibitors (such as, but not limited to, cyclosporin, tacrolimus); mTOR inhibitors (such as, but not limited to, sirolimus, everolimus); anti-proliferatives (such as, but not limited to, azathioprine, mycophenolic acid); corticosteroids (such as, but not limited to, prednisone, cortisone acetate, prednisolone, methylprednisolone, dexamethasone, betamethasone, triamcinolone, beclometasone, fludrocortisone acetate, deoxycorticosterone acetate, aldosterone, hydrocortisone); antibodies (such as, but not limited to, monoclonal anti-IL-2Rα receptor antibodies (basiliximab, daclizumab), polyclonal anti-T-cell antibodies (antithymocyte globulin (ATG), anti-lymphocyte globulin (ALG)), B-cell antagonists, rituximab, natalizumab.

Other therapeutic agents useful for combination with an autotaxin inhibitor as described herein include, but are not limited to: cyclophosphamide, penicillamine, cyclosporine, nitrosoureas, cisplatin, carboplatin, oxaliplatin, methotrexate, azathioprine, mercaptopurine, pyrimidine analogues, protein synthesis inhibitors, dactinomycin, anthracyclines, mitomycin C, bleomycin, mithramycin, Atgam$^{(R)}$, Thymoglobuline®, OKT3®, basiliximab, daclizumab, cyclosporin, tacrolimus, sirolimus, Interferons (IFN-β, IFN-γ), opioids, TNF binding proteins (infliximab, etanercept, adalimumab, golimumab), leflunomide, gold thioglucose, gold thiomalate, aurofin, sulfasalazine, hydroxychloroquinine, minocycline, rapamicin, mycophenolic acid, mycophenolate mofetil, FTY720, as well as those listed in U.S. Pat. No. 7,060,697.

In one embodiment, an autotaxin inhibitor, or a pharmaceutically acceptable salt thereof, is administered in combination with Cyclosporin A (CsA) or tacrolimus (FK506). In one embodiment, an autotaxin inhibitor, or a pharmaceutically acceptable salt thereof, is administered to a mammal in combination with an anti-inflammatory agent including, but not limited to, non-steroidal anti-inflammatory drugs (NSAIDs), phosphodiesterase-4 inhibitors. JNK kinase inhibitors and corticosteroids (glucocorticoids).

In some embodiments, an autotaxin inhibitor, or a pharmaceutically acceptable salt thereof, is administered with corticosteroids. Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In one embodiment, an autotaxin inhibitor, or a pharmaceutically acceptable salt thereof, is administered to a mammal in combination with a non-steroidal anti-inflammatory drug (NSAID). NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

In some embodiments, an autotaxin inhibitor, or a pharmaceutically acceptable salt thereof, is co-administered with an analgesic.

In some embodiments, an autotaxin inhibitor, or a pharmaceutically acceptable salt thereof, is used in combination with radiation therapy (or radiotherapy). Radiation therapy is the treatment of cancer and other diseases with ionizing radiation. Radiation therapy is optionally used to treat localized solid tumors, such as cancers of the skin, tongue, larynx, brain, breast, prostate, colon, liver, uterus and/or cervix. It is also optionally used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to α, β, and γ radiation and ultraviolet light.

In some embodiments, an autotaxin inhibitor is administered with a glucose-lowering agent. In some embodiments, the glucose-lowering agent is selected from among a peroxisome proliferator activated receptor (PPAR) agonist (gamma, dual, or pan), a dipeptidyl peptidase (IV) inhibitor, a glucagon-like peptide-1 (GLP-I) analog, insulin or an insulin analog, an insulin secretagogue, a sodium glucose co-transporter 2 (SGLT2) inhibitor, a glucophage, a human amylin analog, a biguanide, an alpha-glucosidase inhibitor, a meglitinide, a thiazolidinedione, and sulfonylurea. In some embodiments, an autotaxin inhibitor is administered with metformin, sitagliptin, saxaglitpin, repaglinide, nateglinide, exenatide, liraglutide, insulin lispro, insulin aspart, insulin glargine, insulin detemir, insulin isophane, and glucagon-like peptide 1, or any combination thereof. In some embodiments, an autotaxin inhibitor is administered with a lipid-lowering agent.

In some embodiments, an autotaxin inhibitor is administered in combination with at least one additional therapy used to treat cardiovascular disease. In some embodiments, the therapy used to treat cardiovascular disease is an angiotensin-converting enzyme (ACE) inhibitor, angiotensin II receptor blocker (ARB), beta-blocker, diuretic, calcium channel blocker, inhibitor of renin-angiotensin system (RAS), blood-thinning medication, a statin, and a fibrate, and any combination thereof.

Kits and Articles of Manufacture

Described herein are kits for treating a condition, disease or disorder associated with autotaxin activity comprising administering to said individual an autotaxin inhibitor.

For use in the therapeutic applications described herein, kits and articles of manufacture are also described herein. In some embodiments, such kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder that benefit by inhibition of autotaxin, or in which autotaxin is a mediator or contributor to the symptoms or cause.

The container(s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

In some embodiments, a label is on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, a pharmaceutical composition comprising the autotaxin inhibitor is presented in a pack or dispenser device which can contain one or more unit dosage forms. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The following examples are provided for illustrative purposes only and not to limit the scope of the claims provided herein.

Example 1: Synthesis of 3-((6-Chloro-2-cyclopropyl-1-(1-ethyl-1H-pyrazol-4-yl)-7-fluoro-1H-indol-3-yl)thio)-2-fluorobenzoic Acid (Compound A)

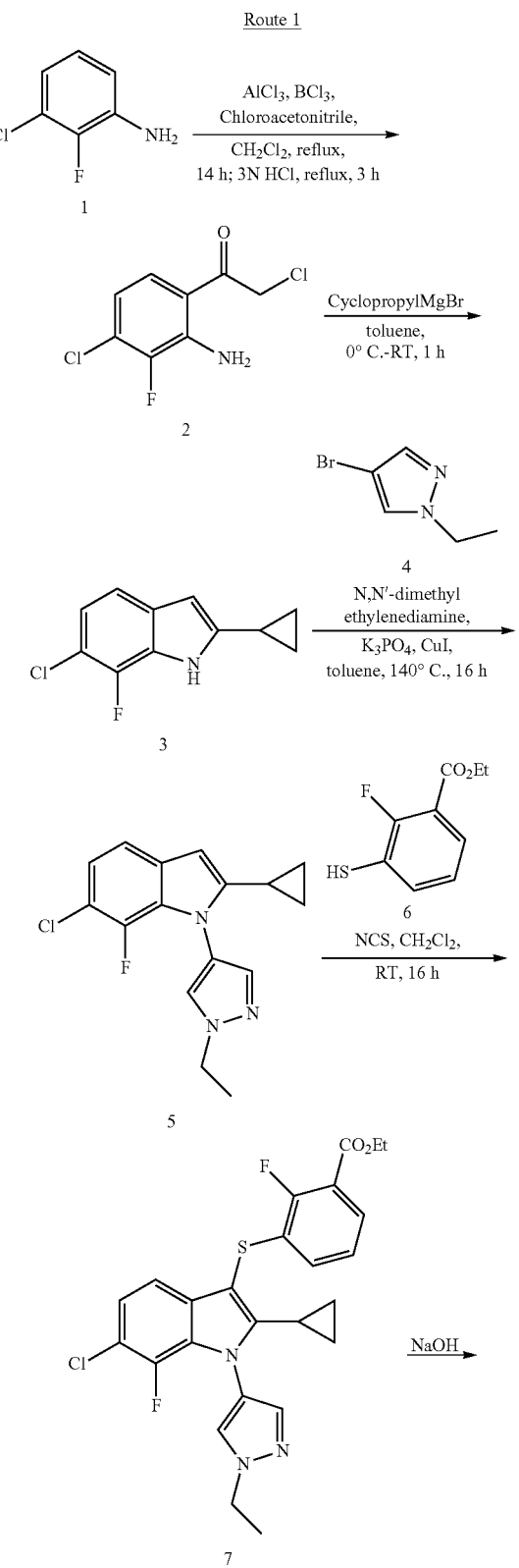

-continued

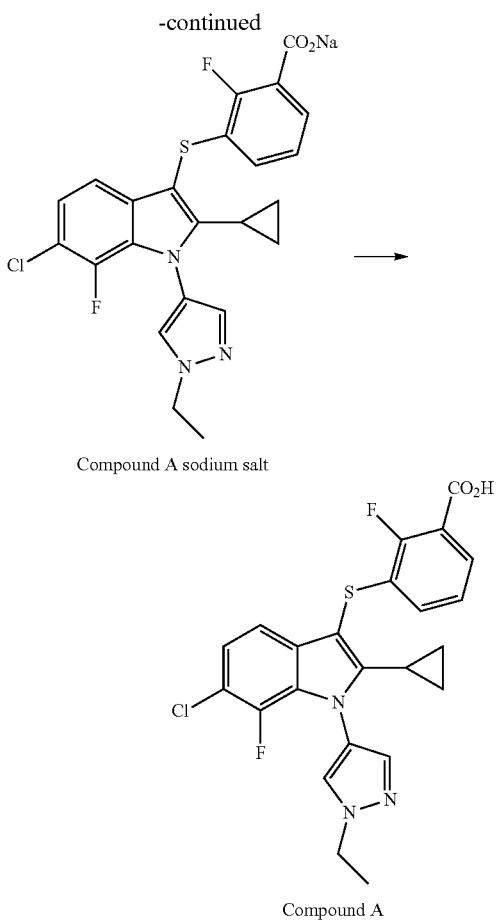

Compound A sodium salt

Compound A

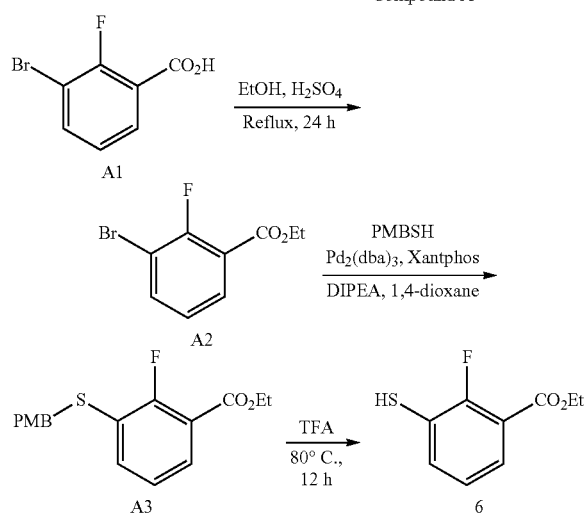

Step 1: Synthesis of 1-(2-amino-4-chloro-3-fluorophenyl)-2-chloroethan-1-one (2)

To a stirred solution of AlCl$_3$ (10.0 g, 75.01 mmol) and BCl$_3$ (1M in n-hexane) (74 mL, 75.01 mmol) in CH$_2$Cl$_2$ (80 mL) was added 3-chloro-2-fluoroaniline 1 (9.0 g, 6.18 mmol) followed by a solution of chloroacetonitrile (11.6 g, 153.64 mmol) in CH$_2$Cl$_2$ (20 mL) at 0° C. under inert atmosphere. The reaction mixture was allowed to stir at RT for 30 minutes; heated to reflux temperature and maintained for additional 14 h. The reaction mixture was then cooled to 0° C., added aqueous 3N HCl solution (100 mL) and raised the temperature to reflux and stirred for 3 h. After completion of the reaction by TLC, the reaction mixture was cooled RT, diluted with water (50 mL) and extracted with CH$_2$Cl$_2$ (2×150 mL). The combined organic extracts were dried over Na$_2$SO$_4$, filtered and concentrated under reduced pressure to obtain the crude. The crude was purified by triturating with n-pentane to afford compound 2 (4.5 g, 33%) as an off-white solid. $^1$H NMR (500 MHz, DMSO-d$_6$): δ 7.61 (d, J=9.0 Hz, 1H), 7.35 (br s, 2H), 6.72 (d, J=9.0 Hz, 1H), 5.06 (s, 2H).

Step 2: Synthesis of 6-chloro-2-cyclopropyl-7-fluoro-1H-indole (3)

To a stirred solution of compound 2 (4.5 g, 20.3 mmol) in toluene (50 mL) was added cyclopropyl magnesium bromide (0.5 M in THF; 102.0 mL, 50.9 mmol) at 0° C. under inert atmosphere. The reaction mixture was stirred at 0° C. for 15 min and then warmed to RT and stirring was continued for additional 1 h. After completion of the reaction by TLC, the reaction mixture was quenched with saturated ammonium chloride solution (10 mL) and extracted with EtOAc (3×75 mL). The combined organic extracts were dried over Na$_2$SO$_4$, filtered and concentrated under reduced pressure to obtain the crude. The crude was purified (silica gel chromatography; 1% EtOAc/Hexanes) to afford compound 3 (2.7 g, 63%) as an off-white solid. $^1$H NMR (500 MHz, DMSO-d$_6$): δ 11.55 (s, 1H), 7.18 (d, J=8.5 Hz, 1H), 6.97 (dd, J=8.5, 6.5 Hz, 1H), 6.16 (s, 1H), 2.03-1.99 (m, 1H), 0.99-0.96 (m, 2H), 0.83-0.80 (m, 2H); LC-MS (ESI): 91.6%; m/z 208.1 (M−H$^+$); (column: X Select CSH C-18, 50×3.0 mm, 3.5 μm); RT 4.32 min; 5 mM NH$_4$OAc: ACN; 0.8 mL/min).

Step 3: Synthesis of 4-bromo-1-ethyl-1H-pyrazole (4)

To a stirred solution of NaH (34.0 g, 0.85 mol; 60% in mineral oil) in THF (400 mL) was added a solution of 4-bromo-1H-pyrazole (50 g, 0.34 mol) in THF (100 mL) at 0° C. under inert atmosphere. The reaction mixture was warmed to RT and maintained at same temperature for 1 h. The reaction mixture was cooled again to 0° C. and added EtI (63.67 g, 0.408 mol) slowly for 5 min. The resultant solution was allowed to warm to RT and then stirred for 16 h. After completion of the reaction (monitored by TLC), the reaction mixture was quenched with ice-cold water (100 mL) and extracted with EtOAc (3×250 mL). The combined organic extracts were dried over Na$_2$SO$_4$, filtered and concentrated under reduced pressure to obtain the crude. The crude was purified (silica gel chromatography; 4-6% EtOAc/Hexanes) to afford compound 4 (43 g, 72%) as a pale yellow liquid. $^1$H NMR (500 MHz, CDCl$_3$): δ 7.45 (s, 1H), 7.41 (s, 1H), 4.15 (q, J=7.5 Hz, 2H), 1.47 (t, J=7.5 Hz, 3H); MS (ESI): m/z 175.0 (M+H$^+$).

Step 4: Synthesis of 6-chloro-2-cyclopropyl-1-(1-ethyl-1H-pyrazol-4-yl)-7-fluoro-1H-indole To a solution of compound 3 (4.3 g, 20.5 mmol) in toluene (50 mL) were added 4-bromo-1-ethyl-1H-pyrazole 4 (4.0 g, 22.8 mmol), potassium phosphate (11.0 g, 51.2 mmol), N,N'-dimethylethylenediamine (722 mg, 8.2 mmol) and Cu(I)I (390 mg, 2.0 mmol) at RT under inert atmosphere. The reaction solution was purged with argon for 15 min and then sealed the tube. The reaction mixture was heated to 140° C. and stirred for 16 h. After completion of the reaction by TLC, the reaction mixture was cooed to RT, diluted with EtOAc (50 mL) and filtered. The filtrate was washed with water (40 mL), brine (40 mL), dried over $Na_2SO_4$, filtered and concentrated under reduced pressure to obtain the crude. The crude was purified (silica gel chromatography; 9% EtOAc/Hexanes) to afford compound 5 (3.9 g, 63%) as a pale brown solid. $^1$H NMR (400 MHz, $CDCl_3$): δ 7.64 (s, 1H), 7.60 (s, 1H), 7.16 (d, J=8.4 Hz, 1H), 7.01 (dd, J=8.4, 6.4 Hz, 1H), 6.12 (s, 1H), 4.25 (q, J=7.2 Hz, 2H), 1.69-1.62 (m, 1H), 1.56 (t, J=7.2 Hz, 3H), 0.92-0.87 (m, 2H), 0.76-0.72 (m, 2H); LC-MS (ESI): 98.6%; m/z 304.3 (M+H$^+$); (column: X Select C-18, 50×3.0 mm, 3.5 μm); RT 4.23 min; 5 mM $NH_4OAc$: ACN; 0.8 mL/min).

Step 5: Synthesis of ethyl
3-bromo-2-fluorobenzoate (A2)

To a stirred solution of 3-bromo-2-fluorobenzoic acid A1 (25.0 g, 114.15 mmol) in ethanol (400 mL) was added conc. $H_2SO_4$ (3 mL) at RT and stirred at reflux temperature for 24 h. The reaction was monitored by LC-MS; after completion of the reaction, the reaction mixture was concentrated to obtain the residue. The residue was diluted with EtOAc (500 mL), washed with water (300 mL), brine (300 mL), dried over $Na_2SO_4$, filtered and concentrated under reduced pressure to afford compound A2 (26.0 g, 92%) as a light yellow liquid. $^1$H NMR (400 MHz, $CDCl_3$): δ 7.88-7.84 (m, 1H), 7.72-7.69 (m, 1H), 7.08-7.04 (m, 1H), 4.39 (q, J=7.2 Hz, 2H), 1.39 (t, J=7.2 Hz, 3H).

Step 6: Synthesis of ethyl
2-fluoro-3-((4-methoxybenzyl)thio)benzoate (A3)

1,4-dioxane (250 mL) was degassed by purging with $N_2$ gas for 30 min and to this, were added a solution of compound A2 (13.2 g, 53.4 mmol) in 1,4-dioxane (50 mL; degassed), (4-methoxyphenyl)methanethiol (PMBSH) (8.2 g, 53.4 mmol), xantphos (1.54 g, 2.66 mmol), diisopropyl ethyl amine (19.6 mL, 106.8 mmol) and $Pd_2(dba)_3$ (1.22 g, 1.33 mmol) at RT. The reaction mixture was heated to 90° C. and stirred for 2 h. The reaction was monitored by TLC; after completion of the reaction, the reaction mixture was diluted with hexane (450 mL) and stirred at RT for 15 min. The resultant solution was filtered through celite and washed with hexane (100 mL). The filtrate was washed water (250 mL) dried over $Na_2SO_4$, filtered and concentrated under reduced pressure to obtain the crude. The crude was purified through silica gel column chromatography using 3-4% EtOAc/Hexanes to afford compound A3 (15 g, 88%) as pale yellow solid. $^1$H NMR (500 MHz, $CDCl_3$): δ 7.78-7.74 (m, 1H), 7.43-7.39 (m, 1H), 7.19 (d, J=8.0 Hz, 2H), 7.07-7.04 (m, 1H), 6.80 (d, J=8.0 Hz, 2H), 4.41 (q, J=7.2 Hz, 2H), 4.08 (s, 2H), 3.78 (s, 3H), 1.41 (t, J=7.2 Hz, 3H). LC-MS (ESI): 89.7%; m/z 318.9 (M–H$^+$); (column: X Select CSH C-18, 50×3.0 mm, 3.5 μm); RT 4.22 min; 5 mM $NH_4OAc$: ACN; 0.8 mL/min).

Step 7: Synthesis of ethyl
2-fluoro-3-mercaptobenzoate (6)

A stirred solution of compound A3 (30.0 g, 93.75 mmol) in TFA (54.5 mL) was heated to 80° C. and stirred for 12 h under inert atmosphere. The reaction was monitored by TLC; after completion of the reaction, the volatiles were removed under reduced pressure. The residue was dissolved in ice-cold water (100 mL), basified with solid sodium bicarbonate and extracted with EtOAc (2×200 mL). The combined organic extracts were dried over $Na_2SO_4$, filtered and concentrated under reduced pressure to obtain the crude. The crude was purified through silica gel column chromatography using 3% EtOAc/Hexanes to afford compound 6 (11.7 g, 62%) as a pale brown syrup. $^1$H NMR (500 MHz, $CDCl_3$): δ 7.70-7.66 (m, 1H), 7.48-7.44 (m, 1H), 7.08-7.04 (m, 1H), 4.20 (q, J=7.5 Hz, 2H), 3.67 (s, 1H), 1.40 (t, J=7.5 Hz, 3H); LC-MS (ESI): 91.8%; m/z 199.0 (M–H$^+$); (column: X Select CSH C-18, 50×3.0 mm, 3.5 μm); RT 2.60 min; 5 mM $NH_4OAc$: ACN; 0.8 mL/min).

Step 8: Synthesis of ethyl 3-((6-chloro-2-cyclopropyl-1-(1-ethyl-1H-pyrazol-4-yl)-7-fluoro-1H-indol-3-yl)thio)-2-fluorobenzoate (7)

To a stirred solution of ethyl 2-fluoro-3-mercaptobenzoate 6 (2.8 g, 14.0 mmol) in $CH_2Cl_2$ (30 mL) under inert atmosphere was added NCS (1.9 g, 14.0 mmol) at RT and allowed to stir for 2 h. To this, compound 5 (3.9 g, 12.8 mmol) in $CH_2Cl_2$ (10 mL) was added at RT and stirred for 16 h. After completion of the reaction by TLC, the reaction mixture was diluted with water (100 mL) and extracted with $CH_2Cl_2$ (2×80 mL). The combined organic extracts were washed with water (2×200 mL), dried over $Na_2SO_4$, filtered and concentrated under reduced pressure to obtain the crude. The crude was purified by triturating with n-pentane (2×50 mL) to afford 7 (5.2 g, 81%) as a pale yellow solid. $^1$H NMR (400 MHz, $CDCl_3$): δ 7.66-7.60 (m, 3H), 7.18 (d, J=8.4 Hz, 1H), 7.08 (dd, J=8.4, 6.5 Hz, 1H), 6.93 (t, J=8.4 Hz, 1H), 6.79-6.75 (m, 1H), 4.40 (q, J=7.2 Hz, 2H), 4.26 (q, J=7.6 Hz, 2H), 1.74-1.68 (m, 1H), 1.56 (t, J=7.2 Hz, 3H), 1.41 (t, J=7.6 Hz, 3H), 1.08-1.04 (m, 2H), 0.89-0.84 (m, 2H); MS (ESI): m/z 502.5 (M+H$^+$); HPLC: 97.5%; (column: Acquity BEH C-18 (50×2.1 mm, 1.7μ); RT 3.44 min; ACN: 0.025% TFA (aq); 0.5 mL/min.

Step 9: Synthesis of 3-((6-chloro-2-cyclopropyl-1-(1-ethyl-1H-pyrazol-4-yl)-7-fluoro-1H-indol-3-yl)thio)-2-fluorobenzoic Acid Sodium Salt (8)

1.0 M NaOH (10.25 mL, 10.2 mmol) was added to a solution of compound 7 (5.14 g, 10.2 mmol) in THF/MeOH (3:1)(56 mL). The mixture was heated at 65° C. for 1.5 h. Additional 1.0 M NaOH (0.23 mL, 0.2 mmol) was added to the reaction and heated at 65° C. for 0.5 h. The mixture was concentrated under reduced pressure to afford the crude acid sodium salt (5.12 g, 100%) as a pale pink solid. The crude solid (600 mg) in THF/EtOH (4:1) (6 mL) and a few drops of water. The mixture filtered and concentrated under reduced pressure and precipitants formed. The solids filtered off and washed with THF/EtOH (9:1) to afford 3-((6-chloro-2-cyclopropyl-1-(1-ethyl-1H-pyrazol-4-yl)-7-fluoro-1H-indol-3-yl)thio)-2-fluorobenzoic acid sodium salt (Compound A sodium salt; 449 mg) as an off white solid. $^1$H NMR (300 MHz, DMSO-$d_6$): δ 8.26 (s, 1H), 7.79 (m, 1H), 7.18-7.13 (m, 3H), 6.81 (t, 1H), 6.43-6.38 (m, 1H), 4.21 (q, 2H), 1.84-1.72 (m, 1H), 1.42 (t, 3H), 0.96-0.93 (m, 2H), 0.84-0.80 (m, 2H); LC-MS: 474 (M$^+$)

3-((6-Chloro-2-cyclopropyl-1-(1-ethyl-1H-pyrazol-4-yl)-7-fluoro-1H-indol-3-yl)thio)-2-fluorobenzoic Acid (Compound A)

To compound A sodium salt (50 mg, 0.10 mmol) suspended in $CH_2Cl_2$ (1 mL) and water (1 mL) was added sat. citric acid until pH 3. The suspension stirred until clear solution. The organic layer was separated, washed with brine, dried over Na$_2$SO$_4$, filtered, and concentrated under reduced pressure to obtain the crude material to afford compound B as a white solid (33 mg, 70%) $^1$H NMR (300 MHz, DMSO-d$_6$): δ 13.39 (s, 1H), 8.24 (s, 1H), 7.79 (s, 1H), 7.57 (t, 1H), 7.22-7.06 (m, 3H), 6.80 (t, 1H), 4.21 (q, 2H), 1.84-1.72 (m, 1H), 1.42 (t, 3H), 0.96-0.88 (m, 2H), 0.86-0.80 (m, 2H); LC-MS: 474 (M$^+$)

Alternative Route to Intermediate 7

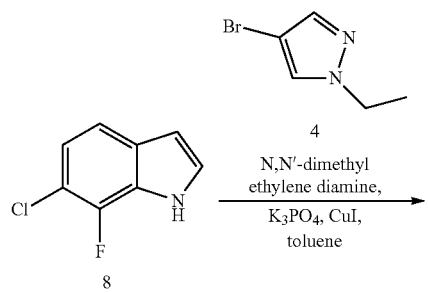

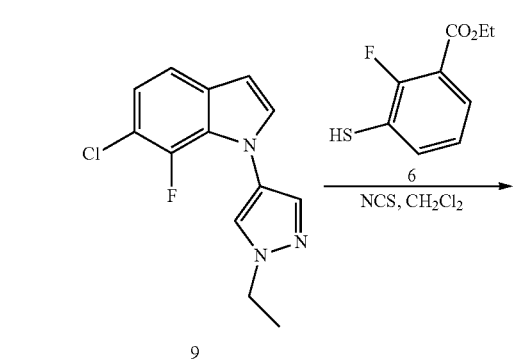

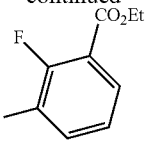

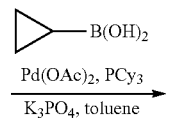

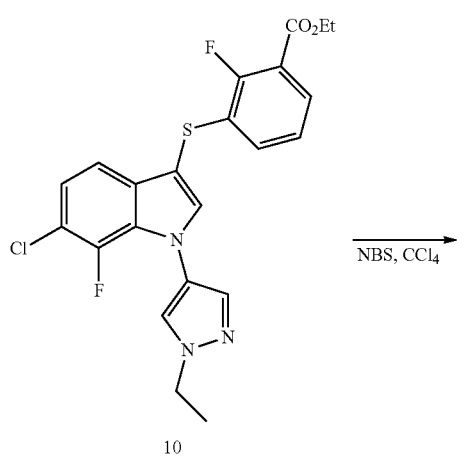

Step 1: Synthesis of 6-chloro-1-(1-ethyl-1H-pyrazol-4-yl)-7-fluoro-1H-indole (9)

To a stirred solution of 6-chloro-7-fluoro-1H-indole 8 (400 mg, 2.36 mmol) in toluene (10 mL) were added 4-bromo-1-ethyl-1H-pyrazole 4 (Step 3 above; 414 mg, 2.36 mmol), potassium phosphate (1.25 g, 5.91 mmol), N,N'-dimethylethylenediamine (84 mg, 0.95 mmol) and Cu(I)I (45 mg, 0.24 mmol) at RT under inert atmosphere. The resulted solution was purged with argon and sealed the tube. The reaction mixture was then heated to 140° C. for 16 h. After completion of the reaction (monitored by TLC), the reaction mixture was cooled to RT, diluted with hexane (10 mL) and filtered through a short pad of celite. The filtrate was washed with water (2×10 mL), dried over Na$_2$SO$_4$, filtered and concentrated under reduced pressure to obtain the crude. The crude was purified (silica gel chromatography; 8-10% EtOAc/Hexanes) to afford compound 9 (224 mg, 36%) as a light brown thick liquid. $^1$H NMR (500 MHz, CDCl$_3$): δ 7.64 (s, 1H), 7.61 (s, 1H), 7.31 (d, J=8.0 Hz, 1H), 7.12-7.07 (m, 2H), 6.60-6.59 (m, 1H), 4.22 (q, J=7.5 Hz, 2H), 1.55 (t, J=7.5 Hz, 3H); LC-MS (ER): 94.7%; m/z 264.1 (M+H$^+$); (column: X Select C-18, 50×3.0 mm, 3.5 μm); RT 3.87 min; 5 mM NH$_4$OAc: ACN; 0.8 mL/min).

Step 2: Synthesis of ethyl 3-((6-chloro-1-(1-ethyl-1H-pyrazol-4-yl)-7-fluoro-1H-indol-3-yl)thio)-2-fluorobenzoate (10)

To a stirred solution of ethyl 2-fluoro-3-mercaptobenzoate 6 (Step 7 above; 212 mg, 1.06 mmol) in CH$_2$Cl$_2$ (4 mL)

under inert atmosphere was added NCS (156 mg, 1.16 mmol) at 0° C. and allowed to stir at RT for 1 h. The reaction mixture was cooled to 0° C. and compound 3 (280 mg, 1.06 mmol) in CH$_2$Cl$_2$ (1 mL) was added slowly and stirred at RT for 16 h. After completion of the reaction by TLC, the reaction mixture was diluted with CH$_2$Cl$_2$ (15 mL) and washed with water (2×20 mL), dried over Na$_2$SO$_4$, filtered and concentrated under reduced pressure to obtain the crude. The crude was purified (silica gel chromatography; 8-10% EtOAc/Hexanes) to afford compound 10 (300 mg, 61%) as a pale brown solid. $^1$H NMR (500 MHz, CDCl$_3$): δ 7.69-7.64 (m, 3H), 7.44 (s, 1H), 7.27 (t, J=8.0 Hz, 1H), 7.16 (dd, J=8.5, 6.0 Hz, 1H), 7.01-6.94 (m, 2H), 4.39 (q, J=7.5 Hz, 2H), 4.24 (q, J=7.0 Hz, 2H), 1.57 (t, J=7.0 Hz, 3H), 1.40 (t, J=7.5 Hz, 3H); LC-MS (ESI): 98.6%; m/z 462.3 (M+H$^+$); (column: X Select C-18, 50×3.0 mm, 3.5 μm); RT 4.70 min; 5 mM NH$_4$OAc: ACN; 0.8 mL/min).

Step 3: Synthesis of ethyl 3-((2-bromo-6-chloro-1-(1-ethyl-1H-pyrazol-4-yl)-7-fluoro-1H-indol-3-yl)thio)-2-fluorobenzoate (11)

To a stirred solution of compound 10 (200 mg, 0.43 mmol) in CCl$_4$ (10 mL) under inert atmosphere was added NBS (178 mg, 0.99 mmol) at RT and stirred for 16 h. After completion of the reaction by TLC, the reaction mixture was diluted with water (10 mL) and extracted with CH$_2$Cl$_2$ (2×20 mL). The combined organic extracts were washed with brine (10 mL), dried over Na$_2$SO$_4$, filtered and concentrated under reduced pressure to obtain the crude. The crude was purified (silica gel chromatography; 5-7% EtOAc/Hexanes) to afford compound 11 (180 mg, 77%) as an off-white solid. $^1$H NMR (500 MHz, CDCl$_3$): δ 7.70-7.67 (m, 1H), 7.65 (s, 2H), 7.30 (d, J=8.0 Hz, 1H), 7.17 (dd, J=8.5, 6.0 Hz, 1H), 7.00-6.98 (m, 2H), 4.40 (q, J=7.5 Hz, 2H), 4.27 (q, J=7.5 Hz, 2H), 1.58 (t, J=7.5 Hz, 3H), 1.40 (t, J=7.5 Hz, 3H); LC-MS (ESI): 99.5%; m/z 542.4 (M$^+$+2); (column: X Select CSH C-18, 50×3.0 mm, 3.5 μm); RT 4.80 min; 5 mM NH$_4$OAc: ACN; 0.8 mL/min).

Step 4: Synthesis of ethyl 3-((6-chloro-2-cyclopropyl-1-(1-ethyl-1H-pyrazol-4-yl)-7-fluoro-1H-indol-3-yl)thio)-2-fluorobenzoate (7)

A solution of compound 11 (150 mg, 0.27 mmol) in toluene (10 mL) under inert atmosphere was purged with argon at RT for 10 min. To this, cyclopropylboronic acid (48 mg, 0.55 mmol), tricyclohexyl phosphine (16 mg, 0.05 mmol), Pd(OAc)$_2$ (6 mg, 0.02 mmol) and potassium phosphate (202 mg, 0.01 mmol) were added at RT under argon. The resultant solution was purged again with argon at RT for 5 min. The reaction mixture was then heated to reflux temperature and stirred for 3 h. The reaction was monitored by TLC & LC-MS; after completion of the reaction, the reaction was cooled to RT, diluted with EtOAc (20 mL) and filtered. The filtrate was washed with water (2×10 mL) and brine (10 mL), dried over Na$_2$SO$_4$, filtered and concentrated under reduced pressure to obtain the crude. This was purified (silica gel chromatography; 6% EtOAc/Hexanes) to afford 7 as a pale yellow solid. $^1$H NMR (400 MHz, CDCl$_3$): δ 7.66-7.7.60 (m, 3H), 7.18 (d, J=8.4 Hz, 1H), 7.08 (dd, J=8.4, 6.5 Hz, 1H), 6.93 (t, J=8.4 Hz, 1H), 6.79-6.75 (m, 1H), 4.40 (q, J=7.2 Hz, 2H), 4.26 (q, J=7.6 Hz, 2H), 1.74-1.68 (m, 1H), 1.56 (t, J=7.2 Hz, 3H), 1.41 (t, J=7.6 Hz, 3H), 1.08-1.04 (m, 2H), 0.89-0.84 (m, 2H); LC-MS (ESI): 92.9%; m/z 502.5 (M$^+$); (column: X Select CSH C-18, 50×3.0 mm, 3.5 μm); RT 4.85 min; 5 mM NH$_4$OAc: ACN; 0.8 mL/min); HPLC: 93.1%; (column: Acquity BEH C-18 (50×2.1 mm, 1.7μ); RT 3.44 min; ACN: 0.025% TFA (aq); 0.5 mL/min.

Example 2: Synthesis of 3-((2,6-dichloro-7-fluoro-1-(1-propyl-1H-pyrazol-4-yl)-1H-indol-3-yl)thio)-2-fluorobenzoic Acid (Compound B)

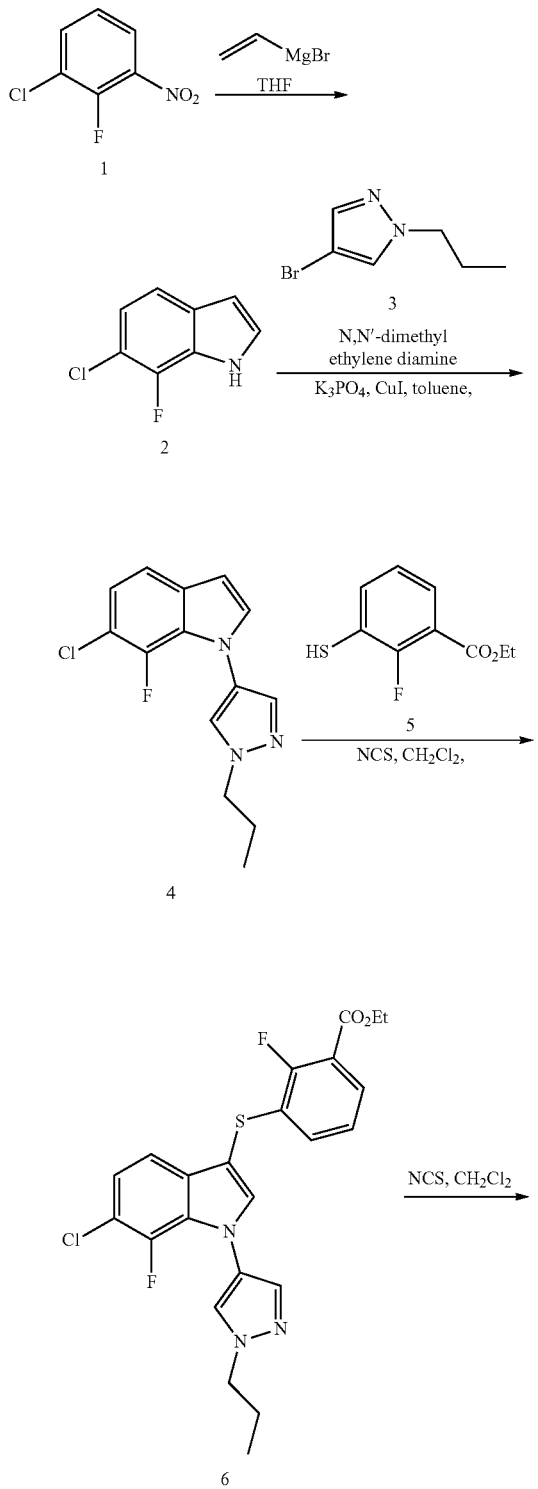

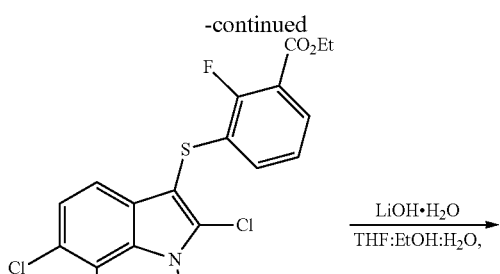

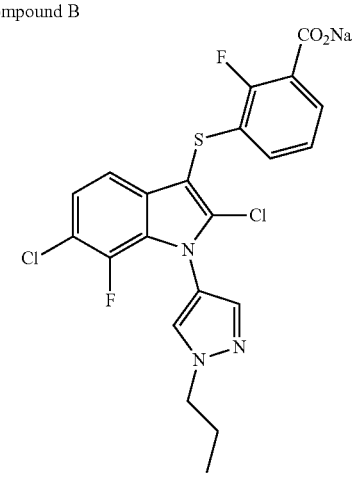

Compound B

Compound B sodium salt

Step 1: Synthesis of 6-chloro-7-fluoro-1H-indole (2)

To a stirred solution of 1-chloro-2-fluoro-3-nitrobenzene 1 (10.0 g, 56.98 mmol) in THF (100 mL) under inert atmosphere was added vinyl magnesium bromide (1M in THF solution; 170 mL, 170.94 mmol) at RT, cooled to −40° C. and stirred for 30 min. The reaction was monitored by TLC; after completion of the reaction, the reaction mixture was quenched with saturated NH$_4$Cl solution (50 mL), extracted with EtOAc (2×50 mL). The combined organic extracts were washed with NH$_4$Cl solution (40 mL), dried over Na$_2$SO$_4$, filtered and concentrated under reduced pressure to obtain the crude. This was purified by silica gel column chromatography using 2% EtOAc/Hexanes to afford compound 2 (1.1 g, 11.4%) as a brown oil. $^1$H NMR (500 MHz, CDCl$_3$): δ 8.36 (br s, 1H), 7.31 (d, J=8.0 Hz, 1H), 7.25-7.22 (m, 1H), 7.08-7.05 (m, 1H), 6.56-6.54 (m, 1H).

Step 2: Synthesis of 6-chloro-7-fluoro-1-(1-propyl-1H-pyrazol-4-yl)-1H-indole (3)

To a stirred solution of compound 2 (1.1 g, 6.48 mmol) in toluene (15 mL) under inert atmosphere were added N,N'-dimethyl ethylene diamine (229 mg, 2.60 mmol), potassium phosphate (3.44 g, 16.27 mmol), 4-bromo-1-propyl-1H-pyrazole 3 (Example 2, Step 3; 1.21 g, 6.50 mmol), CuI (124 mg, 0.65 mmol) at RT, degassed under argon for 15 min; heated to 140° C. and stirred for 20 h in sealed tube. The reaction was monitored by TLC; after completion of the reaction, the reaction mixture was diluted with EtOAc (30 mL), filtered and the filtrate was concentrated under reduced pressure to obtain the crude. This was purified by silica gel column chromatography using 8-10% EtOAc/Hexanes to afford compound 4 (1.3 g, 72%) as brown liquid. $^1$H NMR (500 MHz, CDCl$_3$): δ 7.64 (s, 1H), 7.60 (s, 1H), 7.31 (d, J=7.5 Hz, 1H), 7.12-7.07 (m, 2H), 6.60 (s, 1H), 4.13 (t, J=7.0 Hz, 2H), 1.99-1.91 (m, 2H), 0.97 (t, J=8.0 Hz, 3H); LC-MS (ESI): 93.5%; m/z 278.2 (M+H$^+$); (column: X Select CSH C-18, 50×3.0 mm, 3.5 μm); RT 4.08 min; 5 mM NH$_4$OAc: ACN; 0.8 mL/min).

Step 3: Synthesis of ethyl 3-((6-chloro-7-fluoro-1-(1-propyl-1H-pyrazol-4-yl)-1H-indol-3-yl)thio)-2-fluorobenzoate (6)

To a stirred solution of ethyl 2-fluoro-3-mercaptobenzoate (5; 108 mg, 0.54 mmol) in CH$_2$Cl$_2$ (3 mL) under inert atmosphere was added NCS (72 mg, 0.54 mmol) at RT and stirred for 1 h. To this, compound 4 (150 mg, 0.54 mmol) was added and stirred for 16 h. The reaction was monitored by TLC; after completion of the reaction, the reaction mixture was diluted with water (25 mL) and extracted with CH$_2$Cl$_2$ (2×25 mL). The combined organic extracts were washed with brine (20 mL), dried over Na$_2$SO$_4$, filtered and concentrated under reduced pressure to obtain the crude. This was purified by silica gel column chromatography using 10% EtOAc/Hexanes to afford compound 6 (130 mg, 50%) as an off-white solid. $^1$H NMR (500 MHz, CDCl$_3$): δ 7.69 (s, 1H), 7.67-7.64 (m, 2H), 7.44 (s, 1H), 7.29-7.27 (m, 1H), 7.17-7.14 (m, 1H), 7.01-6.94 (m, 2H), 4.40 (q, J=7.5 Hz, 2H), 4.15 (t, J=8.0 Hz, 2H), 1.98-1.94 (m, 2H), 1.40 (t, J=7.5 Hz, 3H), 0.98 (t, J=8.0 Hz, 3H); LC-MS (ESI): 97.6%; m/z 476.7 (M+H$^-$); (column: X Select CSH C-18, 50×3.0 mm, 3.5 μm); RT 4.84 min; 5 mM NH$_4$OAc: ACN; 0.8 mL/min).

Step 4: Synthesis of ethyl 3-((2,6-dichloro-7-fluoro-1-(1-propyl-1H-pyrazol-4-yl)-1H-indol-3-yl)thio)-2-fluorobenzoate (7)

To a stirred solution of ethyl 3-((6-chloro-7-fluoro-1-(1-propyl-1H-pyrazol-4-yl)-1H-indol-3-yl)thio)-2-fluorobenzoate 6 (100 mg, 0.21 mmol) in CH$_2$Cl$_2$ (3 mL) was added NCS (33.7 mg, 0.25 mmol) at RT under inert atmosphere. After 8 h stirring, additional NCS (33.7 mg, 0.25 mmol) was added at RT and stirred again for 24 h. The reaction was monitored by TLC; after completion of the reaction, the reaction mixture was diluted with water (20 mL) and extracted with CH₂Cl₂ (2×20 mL). The combined organic extracts were washed with brine (15 mL), dried over Na₂SO₄, filtered and concentrated under reduced pressure to obtain the crude. This was purified by silica gel column chromatography using 9-11% EtOAc/Hexanes to afford compound 7 (50 mg, 47%) as an off-white solid. ¹H NMR (400 MHz, CDCl₃): δ 7.71-7.67 (m, 1H), 7.66 (s, 1H), 7.64 (s, 1H), 7.30 (d, J=8.8 Hz, 1H), 7.18 (dd, J=8.4, 6.0 Hz, 1H), 7.04-6.97 (m, 2H), 4.40 (q, J=7.2 Hz, 2H), 4.18 (t, J=7.2 Hz, 2H), 2.04-1.93 (m, 2H), 1.40 (t, J=7.2 Hz, 3H), 0.97 (t, J=7.2 Hz, 3H); LC-MS (ESI): 98.8%; m/z 510.4 (M+H⁺); (column: X Select CSH C-18, 50×3.0 mm, 3.5 µm); RT 4.94 min; 5 mM NH₄OAc: ACN; 0.8 mL/min).

Step 5: Synthesis of 3-((2,6-dichloro-7-fluoro-1-(1-propyl-1H-pyrazol-4-yl)-1H-indol-3-yl)thio)-2-fluorobenzoic Acid (Compound B)

To a stirred solution of compound 7 (50 mg, 0.09 mmol) in THF:EtOH:H₂O (3:1:1, 5 mL) under inert atmosphere was added LiOH.H₂O (12.3 mg, 0.29 mmol) at RT and stirred for 5 h. The reaction was monitored by TLC; after completion of the reaction, the volatiles were removed under reduced pressure. The residue was diluted with water (10 mL), acidified with 1N HCl and extracted with CH₂Cl₂ (2×10 mL). The combined organic extracts were washed with brine (10 mL), dried over Na₂SO₄, filtered and concentrated under reduced pressure to obtain the crude. This was triturated with n-pentane (2×5 mL) to afford the title compound B (15 mg, 34%) as an off-white solid. ¹H NMR (400 MHz, DMSO-d₆): δ 13.24 (br s, 1H), 8.29 (s, 1H), 7.83 (s, 1H), 7.64-7.60 (m, 1H), 7.36-7.34 (m, 2H), 7.15-7.05 (m, 2H), 4.16 (t, J=7.2 Hz, 2H), 1.89-1.80 (m, 2H), 0.85 (t, J=7.2 Hz, 3H); MS (ER): 480.1 (M−H⁺); HPLC: 97.0%; (column: Acquity BEH C-18 (50×2.1 mm, 1.7µ); RT 2.86 min; ACN: 0.025% TFA (aq); 0.5 mL/min.

Step 6: Synthesis of 3-((2,6-dichloro-7-fluoro-1-(1-propyl-1H-pyrazol-4-yl)-1H-indol-3-yl)thio)-2-fluorobenzoic Acid, Sodium Salt (Compound B Sodium Salt)

Ester 7 (27.6 g, 54.0 mmol) was dissolved in THF (400 mL) and EtOH (100 mL). NaOH (54 mL, 1.0 M aq.) was added and the mixture was heated for 1.5 hr at 65° C. An additional 11 mL of NaOH was added and heated for 1.5 hr. The solvent was removed and the residue was dissolved in H₂O/EtOAc. And acidified with saturated citric acid to pH 3. The mixture was extracted 2× with EtOAc and washed with brine and dried over sodium sulphate. After concentrating the product precipitated out and the solids were filtered and washed with 10% EtOAc/Hx. Filtering and evaporation gave the title product Compound B sodium salt as a white powder (23.5 g) MS (ESI): 482.1 (M−H⁺).

Alternatively, Compound B (34.1 g, 71 mmol) was dissolved in THF (313 mL) and cooled in an ice water bath. NaOH (62.6 mL, 1.0 M aq.) was added dropwise over one hour. The solvent was removed and the solid was dried under vacuum to give the title compound as a white solid (31.8 g). MS (ESI): 482.1 (M−H⁺)

Example 3: Synthesis of 4-(2-(6-(4-fluorobenzyl)-1,3-dioxo-5,6,11,11a-tetrahydro-1H-imidazo[1′,5′:1,6]pyrido[3,4-b]indol-2(3H, 5H, 6H)-yl)ethyl)piperidin-1-ium Chloride (Compound C)

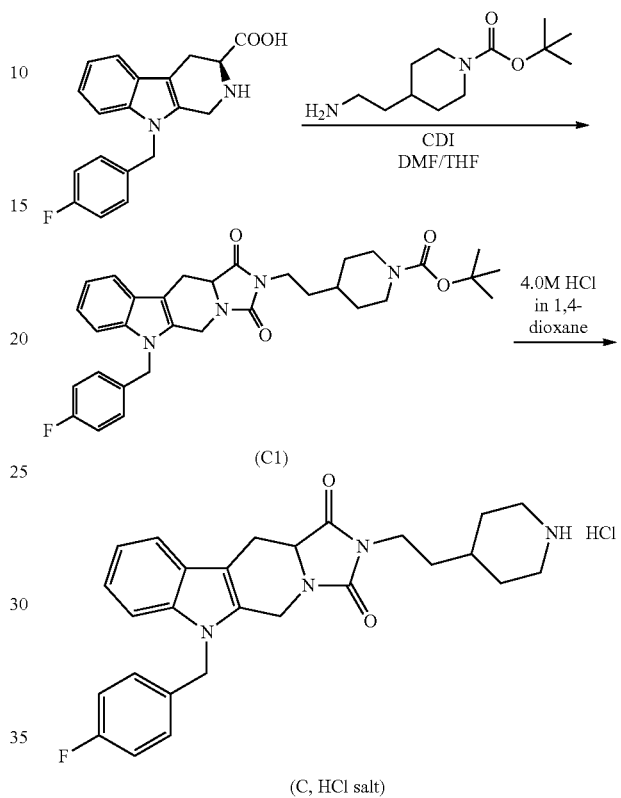

(C, HCl salt)

Step 1: Synthesis of (S)-2,3,4,9-tetrahydro-1H-pyrido[3,4-b]indole-3-carboxylic Acid Formaldehyde (37% aq. solution, 39.7 mL, 490 mmol) was added to a stirred solution of L-tryptophan (100.0 g, 490 mmol) in aqueous NaOH solution (19.6 g in 200 mL of H₂O, 490 mmol) and stirred for 2 hr. The mixture was heated to reflux and stirred for 3.5 hr. The mixture was cooled to 50° C. and carefully acidified to pH 5-6 with 6.0 M HCl₍ₐq₎ solution. The mixture was diluted with water (200 mL). The flask was removed from heat and cooled to room temperature. The precipitates filtered off and washed with water. The solids were resuspended in THF (800 mL), stirred at RT for 1 hr, and filtered to afford (S)-2,3,4,9-tetrahydro-1H-pyrido [3,4-b]indole-3-carboxylic acid (101.3 g, 95%) as beige solid. ¹H NMR (300 MHz, DMSO-d₆): δ 10.93 (s, 1H), 8.88 (br s, 1H), 7.43 (d, 1H), 7.31 (d, 1H), 7.02 (t, 1H), 6.97 (t, 1H), 4.18 (q, 2H), 3.61-3.56 (m, 1H), 3.12 (dd, 1H), 2.83-2.75 (m, 1H); LC-MS [M+H⁺ 217].

Step 2: Synthesis of (S)-2-(tert-butoxycarbonyl)-2,3,4,9-tetrahydro-1H-pyrido[3,4-b]indole-3-carboxylic Acid K₂CO₃ (129.5 g, 937 mmol) dissolved in water (470 mL) was poured into a stirred solution of (S)-2,3,4,9-tetrahydro-1H-pyrido[3,4-b]indole-3-carboxylic acid (101.3 g, 468 mmol) and di-tert-butyl dicarbonate (122.7 g, 562 mmol) in THF (470 mL) at 0° C. The reaction was stirred at room temperature overnight. The next day the THF was removed under reduced pressure and the remaining residue was carefully acidified to pH 3-4 with saturated citric acid solution. The precipitants filtered off and washed with water to afford (S)-2-(tert-butoxycarbonyl)-2,3,4,9-tetrahydro-1H-pyrido[3,4-b]indole-3-carboxylic acid (143.5 g, 97%) as a beige powder. $^1$H NMR (300 MHz, DMSO-$d_6$): δ 12.75 (br s, 1H), 10.88 (s, ½H), 10.83 (s, ½H), 7.40 (d, 1H), 7.28-7.25 (m, 1H), 7.05 (t, 1H), 6.92 (t, 1H), 5.15-5.10 (m, 1H), 4.69 (t, 1H), 4.45-4.29 (m, 1H), 3.30-3.23 (m, 1H), 2.98-2.88 (m, 1H), 1.46 (s, 9×½H), 1.42 (s, 9×½H); LC-MS [M+H$^+$317].

Step 3: Synthesis of (S)-2-(tert-butoxycarbonyl)-9-(4-fluorobenzyl)-2,3,4,9-tetrahydro-1H-pyrido[3,4-b]indole-3-carboxylic Acid (S)-2-(tert-butoxycarbonyl)-2,3,4,9-tetrahydro-1H-pyrido[3,4-b]indole-3-carboxylic acid (20.0 g, 63.2 mmol) in DMF (630 mL) was degassed and the flask was cooled in ice water bath. NaH (60% in mineral oil; 7.8 g, 196.0 mmol) was slowly added portionwise over 45 min at 0° C. and stirred for 1 hr. 4-fluorobenzyl bromide (8.7 mL, 69.5 mmol) was added dropwise over 45 min at 0° C. and stirred for 1.5 hr. The reaction quenched with water. The mixture diluted with water (1.8 L) and washed with EtOAc (1 L). The aqueous layer was acidified to pH 3-4 with solid citric acid. The mixture extracted with EtOAc (3×300 mL). The combined organic extracts were washed with water (900 mL), brine (200 mL), dried over Na$_2$SO$_4$, filtered, and concentrated under reduced pressure. The crude was purified by silica gel column chromatography using 0-30% EtOAc/Hexane to give a solid. The solid was washed with 10% CH$_2$Cl$_2$/hexane to afford (S)-2-(tert-butoxycarbonyl)-9-(4-fluorobenzyl)-2,3,4,9-tetrahydro-1H-pyrido[3,4-b]indole-3-carboxylic acid (19.5 g, 72%) as a white powder. $^1$H NMR (300 MHz, DMSO-$d_6$): δ 12.81 (br s, 1H), 7.48-7.42 (m, 2H), 7.13-6.97 (m, 6H), 5.41-5.28 (m, 2H), 5.14-5.03 (m, 1H), 4.66-4.58 (m, 1H), 4.42-4.27 (m, 1H), 3.32-3.28 (m, 1H), 3.06-2.96 (m, 1H), 1.40 (s, 9×½H), 1.39 (s, 9×½H); LC-MS [M+H$^+$425].

Step 4: Synthesis of (S)-9-(4-fluorobenzyl)-2,3,4,9-tetrahydro-1H-pyrido[3,4-b]indole-3-carboxylic Acid (S)-2-(tert-butoxycarbonyl)-9-(4-fluorobenzyl)-2,3,4,9-tetrahydro-1H-pyrido[3,4-b]indole-3-carboxylic acid (18.9 g, 44.5 mmol), 4M HCl in 1,4-dioxane solution (56 mL, 222.7 mmol), and 1,4-dioxane (85 mL) stirred at RT overnight. The reaction diluted with water (200 mL) and neutralized to pH 7 with Et$_3$N. Water (400 mL) was added and the mixture stirred for 30 min. The solid was collected by filtration and washed with water (300 mL) to afford (S)-9-(4-fluorobenzyl)-2,3,4,9-tetrahydro-1H-pyrido[3,4-b]indole-3-carboxylic acid (13.0 g, 90%) as a pale yellow powder. $^1$H NMR (300 MHz, DMSO-$d_6$): δ 8.95 (br s, 1H), 7.48 (d, 1H), 7.39 (d, 1H), 7.14-6.99 (m, 6H), 5.33 (s, 2H), 4.24 (d, 1H), 4.08 (d, 1H), 3.63-3.58 (m, 1H), 3.17-3.10 (m, 1H), 2.86-2.81 (m, 1H); LC-MS [M+H$^+$325].

Step 5

1,1'-Carbonyl diimidazole (37 mg, 0.23 mmol) in DMF (0.5 mL) was added dropwise to a degassed solution of 4-(aminoethyl)-1-N-Boc-piperidine (53 mg, 0.23 mmol) and THF (0.5 mL). The mixture stirred at RT overnight. (S)-9-(4-fluorobenzyl)-2,3,4,9-tetrahydro-1H-pyrido[3,4-b]indole-3-carboxylic acid (75 mg, 0.23 mmol) and DMF (1 mL) was added and heated at 95° C. overnight. The reaction cooled to RT and diluted with water. The mixture extracted with EtOAc (3 times). The combined organic extracts were washed with brine, dried over Na$_2$SO$_4$, filtered, and concentrated under reduced pressure. The crude material was purified by silica gel column chromatography using 0-50% EtOAc/Hx to afford (C1) as a yellow foam (61 mg, 47%). LC-MS [M+Na 583].

Step 6

(D1) (61 mg, 0.11 mmol) and 4MHCl in 1,4-dioxane solution (1 mL) stirred at RT for 1 hr. The reaction concentrated and then diluted with water (10 mL). It was washed with EtOAc and basified with saturated NaHCO$_{3(aq)}$ solution. The aqueous layer was extracted with EtOAc (2×5 mL). The two organic extracts were combined, washed with brine, dried over Na$_2$SO$_4$, filtered, and concentrated under reduced pressure. The crude material was purified by silica gel column chromatography using 0-10% MeOH/DCM with 2% triethylamine to afford an off white solid. The solid was dissolved in THF (0.5 mL) and 2.0 M HCl in diethyl ether (0.05 mL) was added. The solvent removed to afford (C, HCl salt) as an off white solid (31 mg, 57%). LC-MS [M+H$^+$ 461].

Example 4: Synthesis of 4-(2-(6-(4-fluorobenzyl)-1,3-dioxo-5,6,11,11a-tetrahydro-1H-imidazo [1',5':1,6]pyrido[3,4-b]indol-2(3H, 5H, 6H)-yl)ethyl)piperazin-1-ium Chloride (Compound D)

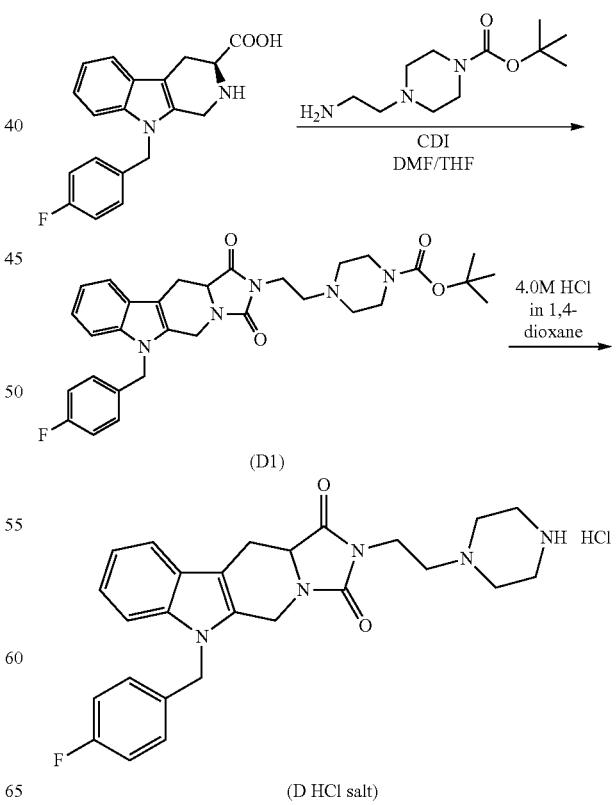

Step 1

1,1'-Carbonyl diimidazole (37 mg, 0.23 mmol) in DMF (0.5 mL) was added dropwise to a degassed solution of tert-Butyl 4-(2-aminoethyl) piperazine-1-carboxylate (53 mg, 0.23 mmol) and THF (0.5 mL). The mixture stirred at RT overnight. (S)-9-(4-fluorobenzyl)-2,3,4,9-tetrahydro-1H-pyrido[3,4-b]indole-3-carboxylic acid (75 mg, 0.23 mmol) and DMF (1 mL) was added and heated at 95° C. overnight. The reaction cooled to RT and diluted with water. The mixture extracted with EtOAc (3 times). The combined organic extracts were washed with brine, dried over Na$_2$SO$_4$, filtered, and concentrated under reduced pressure. The crude material was purified by silica gel column chromatography using 0-100% EtOAc/Hx to afford (D1) as a yellow solid (76 mg, 58%). LC-MS [M+H$^+$562].

Step 2

(D1) (76 mg, 0.14 mmol) and 4MHCl in 1,4-dioxane solution (1 mL) stirred at RT for 1 hr. The reaction concentrated and then diluted with water (10 mL). It was washed with EtOAc and basified with saturated NaHCO$_{3(aq)}$ solution. The aqueous layer was extracted with EtOAc (2×5 mL). The two organic extracts were combined, washed with brine, dried over Na$_2$SO$_4$, filtered, and concentrated under reduced pressure. The crude material was purified by silica gel column chromatography using 0-10% MeOH/DCM with 2% Et$_3$N to afford a pale yellow solid. The solid was dissolved in THF (0.5 mL) and 2.0 M HCl in diethyl ether (0.05 mL) was added. The solvent removed to afford (D, HCl, salt) as a pale yellow solid (37 mg, 55%). LC-MS [M+H$^+$462].

Example 5: Synthesis of 3-((2,6-dichloro-1-(1-ethyl-1H-pyrazol-4-yl)-7-fluoro-1H-indol-3-yl)thio)-2-fluorobenzoic Acid Sodium Salt (Compound E)

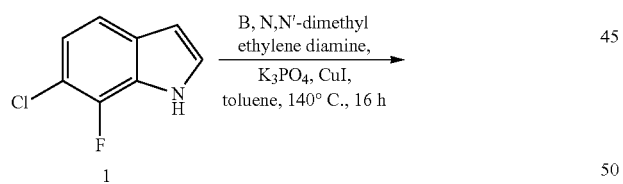

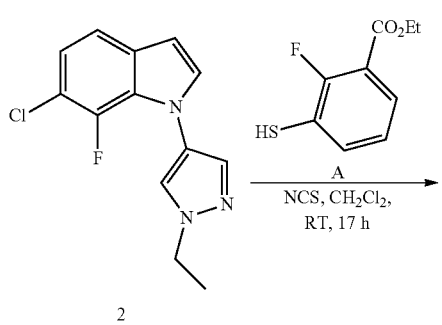

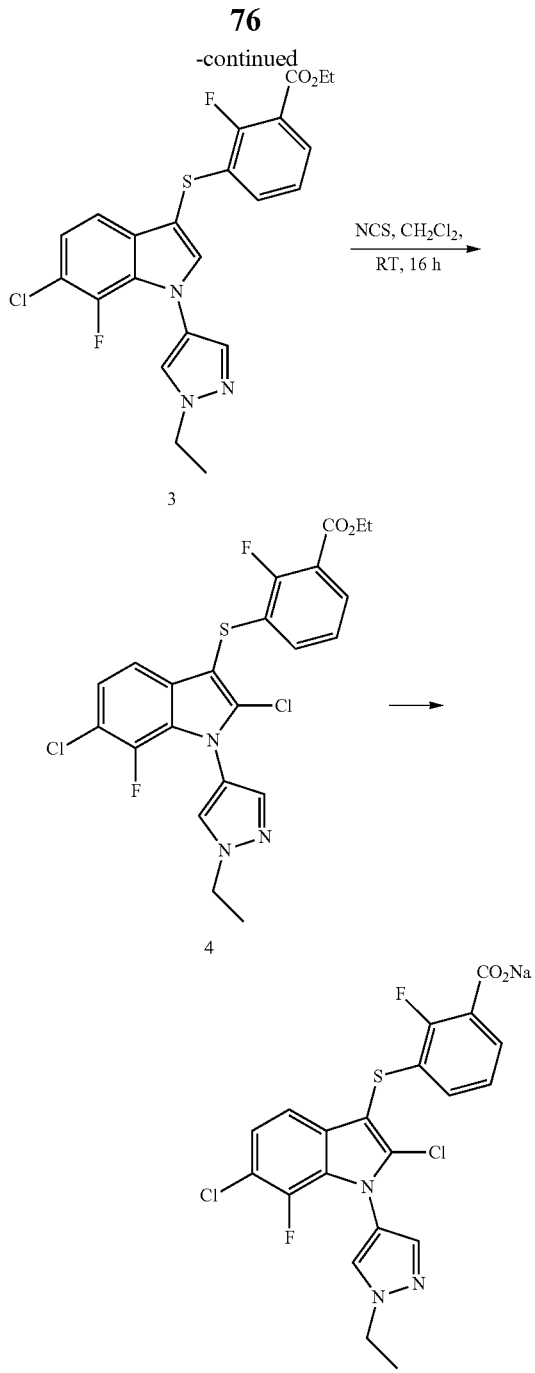

Step 1: Synthesis of ethyl 3-((6-chloro-1-(1-ethyl-1H-pyrazol-4-yl)-7-fluoro-1H-indol-3-yl)thio)-2-fluorobenzoate (3)

Following the procedure of Example 2, Steps 2 and 3 using 4-bromo-1-ethyl-1H-pyrazole B (Example 4, Step 1) in place of 4-bromo-1-propyl-1H-pyrazole 3 in Step 2, the title compound 3 was obtained as a light brown solid. $^1$H NMR (500 MHz, CDCl$_3$): δ 7.69-7.64 (m, 3H), 7.44 (s, 1H), 7.27 (t, J=8.0 Hz, 1H), 7.16 (dd, J=8.5, 6.0 Hz, 1H), 7.01-6.94 (m, 2H), 4.40 (q, J=7.5 Hz, 2H), 4.26 (q, J=8.0 Hz, 2H), 1.57 (t, J=8.0 Hz, 3H), 1.57 (t, J=7.5 Hz, 3H); LC-MS (ESI): m/z 462.5 (M+H$^+$).

Step 2: Synthesis of ethyl 3-((2,6-dichloro-1-(1-ethyl-1H-pyrazol-4-yl)-7-fluoro-1H-indol-3-yl)thio)-2-fluorobenzoate (4)

To a solution of compound 3 (100 mg, 0.21 mmol) in CH$_2$Cl$_2$ (3 mL) under inert atmosphere was added NCS (58 mg, 0.43 mmol) at RT and stirred for 16 h. The reaction mixture was diluted with water (10 mL) and extracted with CH$_2$Cl$_2$ (2×15 mL). The combined organic extracts were dried over Na$_2$SO$_4$ and concentrated under reduced pressure to obtain the crude. The crude was purified (silica gel; 14-17% EtOAc/Hexanes) to afford 4 (35 mg, 33%) as an off-white solid. $^1$H NMR (400 MHz, CDCl$_3$): δ 7.71-7.66 (m, 3H), 7.30 (d, J=7.6 Hz, 1H), 7.19 (dd, J=8.8, 6.4 Hz, 1H), 7.04-6.97 (m, 2H), 4.40 (q, J=7.2 Hz, 2H), 4.27 (q, J=7.6 Hz, 2H), 1.58 (t, J=7.6 Hz, 3H), 1.49 (t, J=7.2 Hz, 3H); LC-MS (ESI): m/z 496.7 (M+H$^-$).

Step 3: Synthesis of 3-((2,6-dichloro-1-(1-ethyl-1H-pyrazol-4-yl)-7-fluoro-1H-indol-3-yl)thio)-2-fluorobenzoic Acid (Compound E)

Following the procedure of Example 1, Step 9 but using Intermediate 4 in place of Intermediate 7, the title Compound E sodium salt was obtained as an off-white solid. LC-MS: m/z 468 (M+1).

Example 6: Synthesis of methyl 6-mercaptopicolinate (Intermediate A)

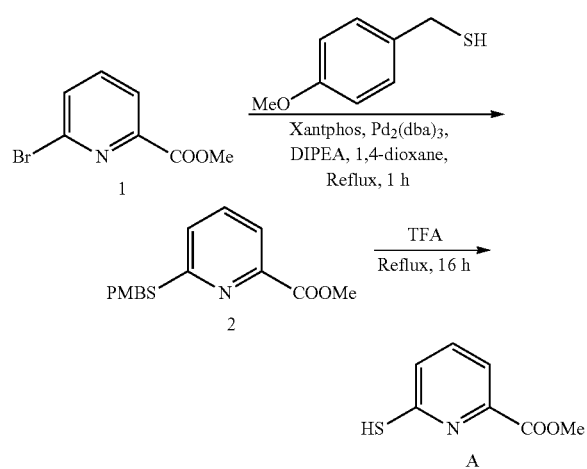

Step 1: Synthesis of methyl 6-((4-methoxybenzyl)thio) picolinate (2)

To a stirred solution of methyl 6-bromopicolinate 1 (8 g, 37.2 mmol) in 1,4-dioxane (110 mL) under inert atmosphere were added (4-methoxyphenyl) methanethiol (5.7 g, 37.0 mmol), xantphos (1.1 g, 1.9 mmol), diisopropyl ethyl amine (13.6 mL, 74.0 mmol), Pd$_2$(dba)$_3$ (847 mg, 0.9 mmol) at RT, degassed under argon for 15 min; heated to reflux and stirred for 1 h. After completion of the reaction (TLC), the reaction mixture was diluted with water (500 mL) and extracted with EtOAc (3×500 mL). The combined organic extracts were dried over Na$_2$SO$_4$, filtered and concentrated under reduced pressure to obtain the crude. The crude was purified (silica gel; 10% EtOAc/hexanes) to afford compound 2 (8 g, 75%) as yellow solid. $^1$H NMR (400 MHz, CDCl$_3$): δ 7.78 (d, J=7.6 Hz, 1H), 7.57 (t, J=8.0 Hz, 1H), 7.42-7.40 (m, 2H), 7.29-7.25 (m, 1H), 6.82 (d, J=8.4 Hz, 2H), 4.44 (s, 2H), 4.00 (s, 3H), 3.77 (s, 3H); LC-MS: 95.7%; 290.3 (M$^+$+1); (column: X Select C-18, 50×3.0 mm, 3.5 μm); RT 4.10 min. 5 mM NH$_4$OAc: ACN; 0.8 mL/min).

Step 2: Synthesis of methyl 6-mercaptopicolinate (Intermediate A)

A stirred solution of compound 2 (6 g, 20.7 mmol) in Trifluoro acetic acid (50 mL) under inert atmosphere was heated to reflux and stirred for 16 h. After completion of the reaction (TLC), the volatiles were removed under reduced pressure. The residue was diluted with EtOAc (500 mL), washed with aqueous NaHCO$_3$ solution (3×250 mL). The organic extract were dried over Na$_2$SO$_4$, filtered and concentrated under reduced pressure to obtain the compound 6 (3.5 g, crude) as pale brown solid. LC-MS: 61.1%; 170 (M$^+$+1); (column: X Select C-18, 50×3.0 mm, 3.5 μm); RT 1.41 min. 5 mM NH$_4$OAc: ACN; 0.8 mL/min).

Example 7: Synthesis of methyl 2-(2-fluoro-3-mercaptophenyl)acetate (Intermediate B)

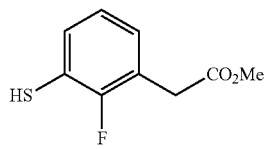

Prepared according to the procedure described in WO2012/024620, Example 154, p 203.

Example 8: Synthesis of 6-((2,6-dichloro-7-fluoro-1-(1-propyl-1H-pyrazol-4-yl)-1H-indol-3-yl)thio) picolinic Acid (Compound F)

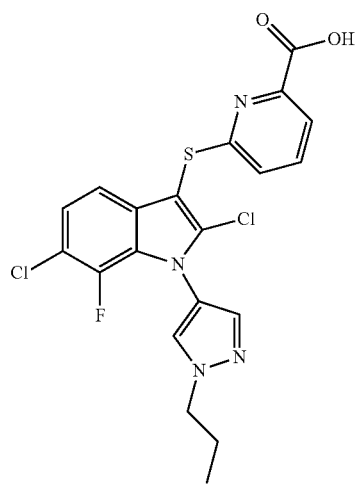 [SMILES: CCCn1cc(-n2c(Cl)c(Sc3cccc(C(=O)O)n3)c3ccc(Cl)c(F)c32)cn1]

Using the procedure in Example 2 but substituting methyl 6-mercaptopicolinate (Intermediate A) for ethyl 2-fluoro-3- mercaptobenzoate in step 3 the title compound was prepared. LC-MS: 465.2 (M$^+$+1).

Example 9: Synthesis of 6-((2,6-dichloro-1-(1-ethyl-1H-pyrazol-4-yl)-7-fluoro-1H-indol-3-yl)thio) picolinic Acid (Compound G)

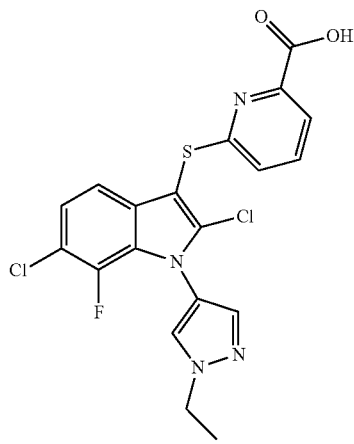 [SMILES: CCn1cc(-n2c(Cl)c(Sc3cccc(C(=O)O)n3)c3ccc(Cl)c(F)c32)cn1]

Using the procedure in Example 5 except substituting methyl 6-mercaptopicolinate (Intermediate A) for ethyl 2-fluoro-3-mercaptobenzoate in step 2 the title compound was prepared. LC-MS: 449.2 (M$^+$+1).

Example 10: Synthesis of 2-(3-((2,6-dichloro-7-fluoro-1-(1-propyl-1H-pyrazol-4-yl)-1H-indol-3-yl)thio)-2-fluorophenyl)acetic Acid (Compound H)

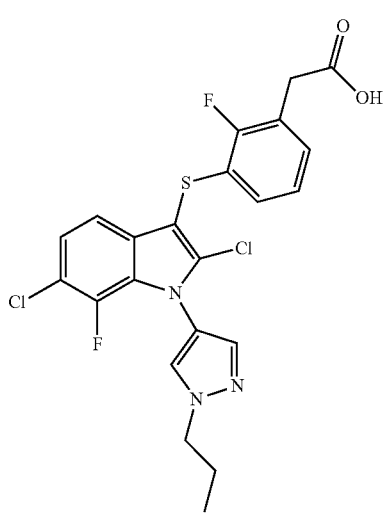 [SMILES: CCCn1cc(-n2c(Cl)c(Sc3cccc(CC(=O)O)c3F)c3ccc(Cl)c(F)c32)cn1]

Using the procedure in Example 2 except substituting methyl 2-(2-fluoro-3-mercaptophenyl)acetate (Intermediate B) for ethyl 2-fluoro-3-mercaptobenzoate in step 3 the title compound was prepared. LC-MS: 496.6 (M$^+$+1).

Example 11: Synthesis of 2-(3-((2,6-dichloro-1-(1-ethyl-1H-pyrazol-4-yl)-7-fluoro-1H-indol-3-yl)thio)-2-fluorophenyl)acetic Acid (Compound I)

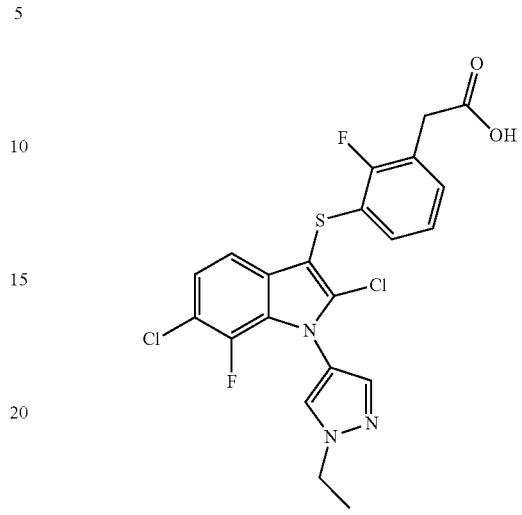

Using the procedure in Example 5 except substituting methyl 2-(2-fluoro-3-mercaptophenyl)acetate (Intermediate B) for ethyl 2-fluoro-3-mercaptobenzoate in step 2 the title compound was prepared. LC-MS: 482.3 (M$^+$+1).

Example 12: Parenteral Pharmaceutical Composition

To prepare a parenteral pharmaceutical composition suitable for administration by injection (subcutaneous, intravenous), 1-100 mg of a water-soluble salt of an autotaxin inhibitor, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection.

Example 13: Oral Solution

To prepare a pharmaceutical composition for oral delivery, a sufficient amount of an autotaxin inhibitor, or a pharmaceutically acceptable salt thereof, is added to water (with optional solubilizer(s), optional buffer(s) and taste masking excipients) to provide a 20 mg/mL solution.

Example 14: Oral Tablet

A tablet is prepared by mixing 20-50% by weight of an autotaxin inhibitor, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example 15: Oral Capsule

To prepare a pharmaceutical composition for oral delivery, 10-500 mg of an autotaxin inhibitor, or a pharmaceutically acceptable salt thereof, is mixed with starch or other suitable powder blend. The mixture is incorporated into an oral dosage unit such as a hard gelatin capsule, which is suitable for oral administration.

In another pharmaceutical composition, 10-500 mg of an autotaxin inhibitor, or a pharmaceutically acceptable salt thereof, is placed into size 4 capsule, or size 1 capsule (hypromellose or hard gelatin) and the capsule is closed.

Example 16: Topical Gel Composition

To prepare a pharmaceutical topical gel composition, an autotaxin inhibitor, or a pharmaceutically acceptable salt thereof, is mixed with hydroxypropyl cellulose, propylene glycol, isopropyl myristate and purified alcohol USP. The resulting gel mixture is then incorporated into containers, such as tubes, which are suitable for topical administration.

Example 17: Human Autotaxin Assay

ATX activity is assayed in concentrated conditioned media from Hep3B human hepatocellular carcinoma cells by measuring the amount of choline released from the substrate, lysophosphatidylcholine (LPC) as it is cleaved to LPA. Conditioned media is collected from confluent Hep3B cells and concentrated 10-20-fold using Centriprep-30 filter devices (Millipore). To assay for autotaxin inhibition, 10-20 µL of the concentrated conditioned media is incubated with 2.5 µL of a test compound in DMSO and 72.5-82.5 µL lyso-PLD buffer (100 mM Tris pH 9, 500 mM NaCl, 5 mM $MgCl_2$, 5 mM $CaCl_2$, 0.05% Triton X-100 in the presence or absence of 0.2% fatty-acid-free human serum albumin) for 15 min at 37° C. After the 15 min incubation, 5 ul of 2 mM LPC (14:0; Avanti Polar Lipids Cat #855575C) diluted in lyso-PLD buffer is added for a final concentration of 100 uM and the incubation continued for 1.5-3 hours at 37° C. 100 µl of a color mix containing 4.5 mM 4-aminoantipyrine, 2.7 mM N-ethyl-N-(2-hydroxy-3-sulfopropyl)-m-toluidine, 21 units/ml horseradish peroxidase and 3 units/ml choline oxidase in 50 mM Tris, pH 8, 4.5 mM $MgCl_2$ is added and the incubation continued for 15 minutes at room temperature before reading the absorbance at 555 nm.

Illustrative biological activity of representative compounds in the human autotaxin assay described herein is presented in the following table:

| Compound | $IC_{50}$ (µM) |
| --- | --- |
| Compound A | A |
| Compound B | A |
| Compound C | A |
| Compound D | A |
| Compound E | A |
| Compound F | A |
| Compound G | A |
| Compound H | A |
| Compound I | A |

A is ≤ 0.5 µM; B is > 0.5 µM but ≤ 1 µM; C > 1 µM.

Example 18: Human Whole Blood Autotaxin Assay

Inhibition of ATX activity in human whole blood is assayed by measuring the concentration of 20:4 LPA in plasma after a prolonged incubation at 37° C. Blood is drawn from consenting human volunteers into heparin vacutainer tubes and 200 µl aliquots are added to 2 µl test compound in DMSO or DMSO alone. Several of the vehicle tubes are centrifuged immediately at 800×g for 10 minutes at 4° C. and the plasma removed for processing to determine the baseline concentration of 20:4 LPA. The remaining blood samples containing vehicle or test compound are incubated at 37° C. for 4 hours before centrifuging at 800×g for 10 minutes at 4° C. to obtain plasma. Plasma is processed for LCMS as follows: 40 ul plasma is removed and 5 volumes of methanol containing 125 ng/ml 17:0 LPA as an internal standard are added and the mixture incubated at −20° C. for 10 min before centrifuging at 4000×g for 10 minutes at 4° C. 150 µl of the supernatant is transferred to a 96-well plate and diluted with 100 µl of an organic solution (90:10:0.1 of water/acetonitrile/ammonium hydroxide) for analysis of 20:4 LPA concentrations by LCMS. LPA 20:4 and the internal standard (LPA 17:0) were analyzed on a quadrupole mass spectrometer (ABI Sciex 4000QTrap) in the negative ion mode (ESI) by multiple reaction monitoring (MRM). The mobile phases contain 0.1% ammonium hydroxide in 90% water/10% acetonitrile (solvent A) and 0.1% ammonium hydroxide in 90% acetonitrile/10% water (solvent B). The flow rate was maintained at 0.8 mL/min and the total run time was 3 min. Analytes were separated using a linear gradient as follows: 1) mobile phase was held for 0.5 min at 10% B; 2) B was increased from 10% to 90% over the next 1 min; 3) B was held constant for 0.5 min at 90%; and 4) B was returned to the initial gradient conditions.

Example 19: Autotaxin-induced Itch Model

Mice are infected with adenovirus expressing autotaxin under control of a CMV (cytomegalovirus) or AFP (alpha-fetoprotein) promoter. Infected mice experience an increased scratch response after infection. After infection with the ATX expressing adenovirus and observation of increased scratch response, mice are treated with an autotaxin inhibitor and monitored for inhibition of itch.

An increased scratch response was seen in mice infected the CMV-ATX adenovirus.

Example 20: Myelin Oligodendrocyte Glycoprotein (MOG)-induced Experimental Autoimmune Encephalomyelitis (EAE) Model EAE is induced in mice by immunization with MOG peptide (35-55) which results in progressive paralysis. Mice are treated with an autotaxin inhibitor at 60 mpk BID either at the time of immunization (prophylactic dosing) or after the first sign of symptoms (therapeutic dosing) and monitored for signs of paralysis.

Example 21: MDA-MB-435 Melanoma Cell Migration Assay

Cells from MDA-MB-435S human melanoma line are maintained in subconfluent culture in media containing FBS and penicillin/streptomycin. The day before the assay, cells are serum-starved overnight in media containing 0.1-0.2% fatty-acid-free BSA. On the day of the assay, the conditioned media is removed from the cells, centrifuged for clarification and set aside. The cells are then harvested by scraping, counted, and pelleted by centrifugation. The cells are resuspended at 1.05× the final desired density in the conditioned media. The assays are performed in duplicate using the Neuroprobe 96-well chemotaxis system with 8 µm pore size and fibronectin-coated filters. 152 µL cells are added to 8 µL test autotaxin inhibitor compound and incubated for 15 min at 37° C. The lower chamber is loaded with 2-10 µM LPC and then 50 µL of the cell/test compound suspension is added to the top of each filter well site. The filters are incubated at 37° C. for 1-24 hours and non-migrated cells removed from the top of the filter by rinsing with PBS and scraping. The filter is air dried then stained before reading the absorbance at 580 nm.

In this cell migration assay, compound A had an $IC_{50}$ of 4 nM and compound B had an $IC_{50}$ of 15 nM.

Example 22: Mouse Carbon Tetrachloride ($CCl_4$)-induced Liver Fibrosis Model

Female or male balb/c mice receive $CCl_4$ (0.8-1.0 ml/kg body weight) diluted in olive oil via intraperitoneal injection twice a week for 6-8 weeks. (Higazi, A. A. et al, Clin Exp Immunol. 2008 April; 152(1):163-73). Control mice receive an equivalent volume of olive oil only. Autotaxin inhibitor or vehicle is delivered orally daily starting at the time of $CCl_4$ injection (prophylactically) or starting at 1-3 weeks after the first $CCl_4$ injection (therapeutically). At the end of the study, mice are sacrificed using inhaled isoflurane and blood is drawn via cardiac puncture for subsequent analysis of ALT/AST levels. The liver is harvested and frozen at −80° C. for the biochemical analysis of liver fibrosis or fixed in 10% neutral buffered formalin for histological assessment of liver fibrosis. For the biochemical assessment of liver fibrosis, liver tissue homogenates are analyzed for collagen concentration using a hydroxyproline assay. For the histological assessment of liver fibrosis, fixed liver tissue is stained with Picrosirius red and liver fibrosis is determined by quantitative, computer-assisted densitometry using light microscopy.

Example 23: Mouse Choline-deficient, L-amino acid-defined, High-fat Diet (CDAA/HFD) Model of Liver Fibrosis Mice are fed a choline deficient diet supplemented with 0.1% methionine and 60% kCal fat (CDAA/HFD) for 12-14 weeks. Mice receive 1, 3, 10, or 30 mpk of autotaxin inhibitor test compound or vehicle starting at the beginning of week 6 after feeding (therapeutically). The following liver enzymes are measured weekly: aspartate transaminase, alkaline phosphatase and bilirubin. At the end of the study, mice are sacrificed and the liver harvested and frozen at −80° C. for the biochemical analysis of liver fibrosis or fixed in neutral-buffered formalin for histological assessment of liver fibrosis. For the biochemical assessment of liver fibrosis, liver tissue homogenates are analyzed for collagen concentration using a hydroxyproline assay. For the histological assessment of liver fibrosis, fixed liver tissue is stained with Picrosirius Red (PSR) stain and severity of liver fibrosis scored using light microscopy. After qualitative scoring of liver fibrosis, quantitation of fibrosis was determined using whole slide images captured at 20× magnification and calculating the percentage of the liver section that was PSR-positive using Indica Labs' Halo® area quantification image analysis software.

In this liver fibrosis model, compound A significantly reduced liver fibrosis when dosed at 30 mpk and compound B significantly reduced liver fibrosis when dosed at 10 mpk. Treatment with either compound A (30 mpk) or compound B (10 mpk) resulted in an approximately 35% decrease in % PSR positive area.

In this animal model, treatment of mice with 3 mg/kg, 10 mg/kg or 30 mg/kg of compound A resulted in about 72%, 76% and 90% inhibition of trough plasma autotaxin activity, respectively (as measured by choline production). Treatment of mice with 1 mg/kg, 3 mg/kg or 10 mg/kg of compound B resulted in about 49%, 67%, and 75% inhibition of trough plasma autotaxin activity, respectively (as measured by choline production).

Example 24: Mouse Diet-induced NASH (Nonalcoholic Steatohepatitis) Liver Fibrosis Model Mice are injected with a low dose of streptozotocin two days after birth and then fed a high-fat diet starting after 4 weeks of age until 12 weeks of age. Mice are treated with test compound starting at 6 weeks of age. At the end of the study, mice are sacrificed and blood drawn for determination of non-fasting blood glucose and ALT/AST. The liver is harvested, weighed and frozen at −80° C. for biochemical analysis of liver fibrosis and liver triglycerides or fixed in neutral-buffered formalin for histological assessment of liver fibrosis, steatosis and inflammation. For the biochemical assessment of liver fibrosis, liver tissue homogenates are analyzed for collagen concentration using a hydroxyproline assay and for liver triglycerides using the Triglyceride E-test kit (Wako, Japan). For the histological assessment of inflammation and steatosis, fixed liver tissue is stained with hematoxylin and eosin (H&E) and severity of inflammation and steatosis is scored using light microscopy. For the histological assessment of liver fibrosis, fixed liver tissue is stained with Picrosirius Red (PSR) stain and severity of liver fibrosis scored using light microscopy.

In this fibrosis model, compound A at 10 mg/kg showed a significant reduction in liver fibrosis and a significant reduction in NAFLD activity score (composite score of inflammation, steatosis and hepatocyte ballooning scores).

Example 25: Rat Diethylnitrosamine (DEN)-induced Liver Fibrosis and Hepatocellular Carcinoma Male Wistar rats receive weekly intraperitoneal injections of 35-100 mg/kg diethylnitrosamine (DEN) for 13-18 weeks in a total volume of 1.5 ml phosphate-buffered saline (PBS) to induce cirrhosis and hepatocellular carcinoma (HCC). Control rats receive weekly injections of an equivalent volume of PBS. An autotaxin inhibitor or vehicle is delivered orally daily starting 6-7 weeks after the initial DEN injection. At the end of the study, rats are sacrificed using inhaled isoflurane and blood is drawn via cardiac puncture for subsequent analysis of ALT/AST levels and drug concentrations. The liver is harvested and frozen at −80° C. for biochemical analysis of fibrosis or fixed in 10% neutral buffered formalin for histological assessment of liver fibrosis. For biochemical assessment of fibrosis, liver tissue homogenates are analyzed for collagen concentration using a hydroxyproline assay. For histological assessment of liver fibrosis and HCC, fixed liver tissue is stained with Picrosirius stain and H&E and liver fibrosis and HCC is determined using light microscopy.

In this animal model, compound A had a positive effect on the reduction of liver fibrosis at 5 mpk.

Example 26: Mouse Model of Bleomycin-Induced Skin Fibrosis

A mouse model of bleomycin-induced skin fibrosis was used to evaluate the effect of autotaxin inhibitors on skin fibrosis. Methods were adapted from (Yamamoto, T et al. The Journal of Investigative Dermatology, 112: 456-462, 1999). C57Bl/6 mice were anesthetized with isoflurane and two areas shaved bilaterally on the lower dorsolateral region. Bleomycin (10-50 µg in 100 µl) prepared in sterile filtered PBS (or PBS control) was administered subcutaneously to each shaved region once daily for 5 to 7 days per week for a total of 4 weeks (28 days).

Compound A and Compound B were prepared in 0.5% methyl cellulose and delivered orally once daily from Day 1-28 (prophylactically) or from Day 7-28 (therapeutically).

On day 28 all animals were sacrificed. The dorsolateral skin removed, trimmed of adherent subcutaneous fat and a 6 mm biopsy punch was used to collect two skin samples from each subject. One sample was fixed in 10% neutral buffered formalin and submitted for histological analysis. The second sample was frozen at −80° C. for further processing of collagen content using a hydroxyproline assay.

In this skin fibrosis model, compound A showed a significant reduction in skin fibrosis when dosed prophylactically or therapeutically.

FIG. 1 shows the average±SEM hydroxproline content in a 6 mm skin punch biopsy. Compound A showed a significant reduction in skin hydroxyproline content when dosed prophylactically or therapeutically.

In this animal model, treatment of mice with 60 mg/kg of compound A resulted in an approximately 95% inhibition of trough plasma autotaxin activity (as measured by choline production).

Example 27: Mouse Unilateral Ureteral Obstruction (UUO) Kidney Fibrosis Model

C57BL/6 mice undergo unilateral ureteral obstruction (UUO) surgery or sham surgery to the left kidney. Briefly, a longitudinal, upper left incision is performed to expose the left kidney. The renal artery is located and silk thread is passed between the artery and the ureter. The thread is looped around the ureter and knotted insuring full ligation of ureter. The kidney is returned to abdomen, the abdominal muscle is sutured and the skin is stapled closed. Test compound or vehicle is delivered orally once or twice daily either prophylactically (starting on Day 0) or therapeutically (starting on Day 3). All animals are sacrificed using inhaled isoflurane 10 days after UUO surgery. Following sacrifice, blood is drawn via cardiac puncture and both kidneys are harvested. Each kidney is either snap frozen at −80° C. for biochemical analysis of fibrosis or fixed in 10% neutral buffered formalin for histological assessment of kidney fibrosis. Kidney tissue homogenates are analyzed for collagen content using a hydroxyproline assay. Fixed kidney tissue is stained using hematoxylin and eosin (H&E) and Picrosirius red and kidney fibrosis is determined using light microscopy.

Figure 2:
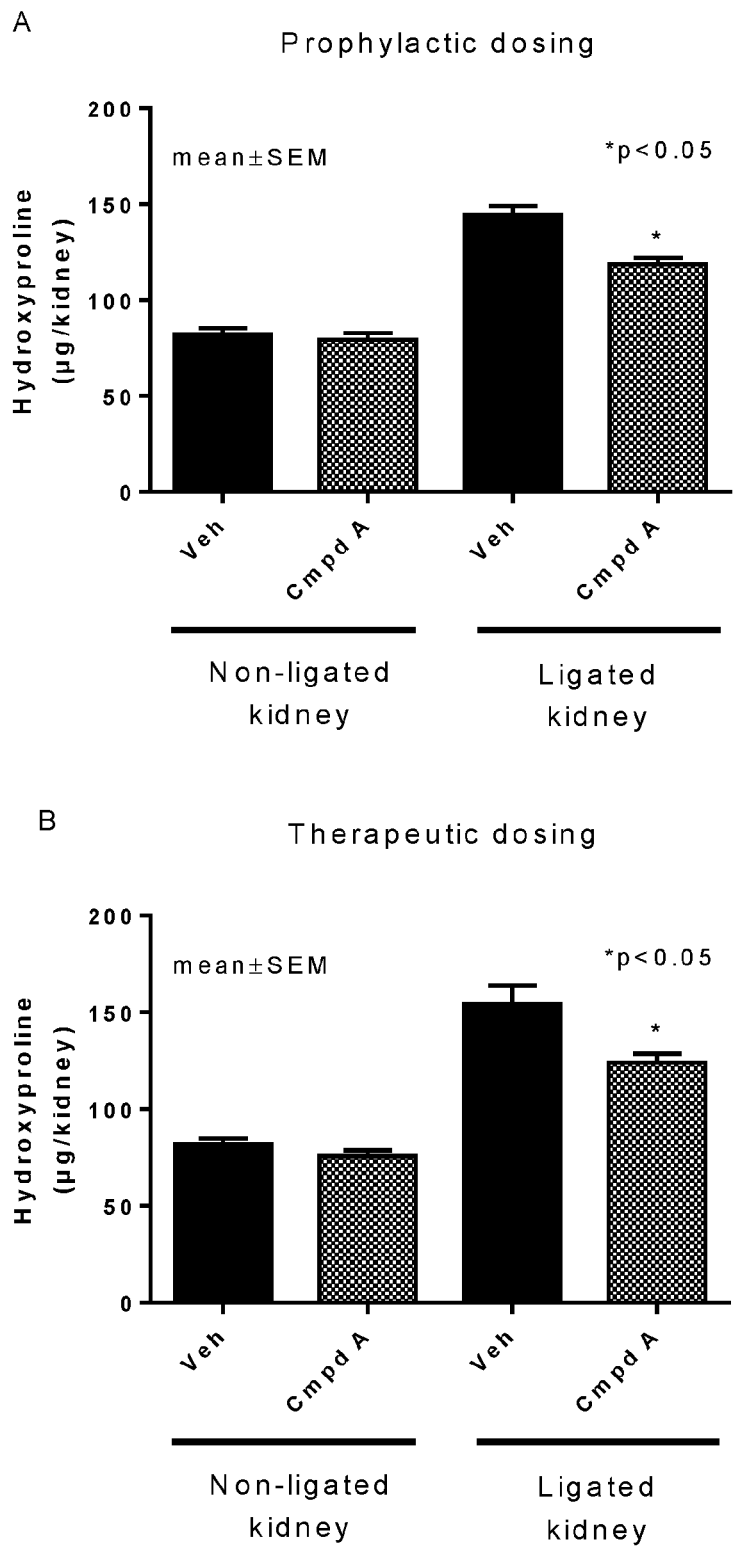
FIG. 2 provides hydroxyproline levels in non-ligated and ligated kidneys from UUO-mice after prophylactic (A) or therapeutic (B) treatment with an autotaxin inhibitor. Cmpd A attenuates renal fibrosis when dosed prophylactically (A) or therapeutically (B) in a mouse UUO model.

FIG. 2 shows the effect of prophylactic dosing (A) and therapeutic dosing (B) of compound A on hydroxyproline content in the non-ligated and ligated kidneys after UUO.

Prophylactic or therapeutic dosing of compound A assay reduced hydroxyproline content in the ligated kidneys of mice by approximately 40%.

Example 28: Mouse Peritoneal Fibrosis Model

Peritoneal fibrosis is induced in mice by injection of 0.1% chlorhexidine gluconate (CG) dissolved in 15% ethanol/PBS into the peritoneal cavity every other day for a period of 21 days. An autotaxin inhibitor or vehicle is delivered orally once or twice daily either prophylactically (starting on the day of the initial CG injection) or therapeutically (starting on Day 7 after the initial CG injection). At the end of the study, mice are sacrificed and peritoneal tissue is excised. Peritoneal fibrosis is determined biochemically using a hydroxyproline assay.

Figure 3:
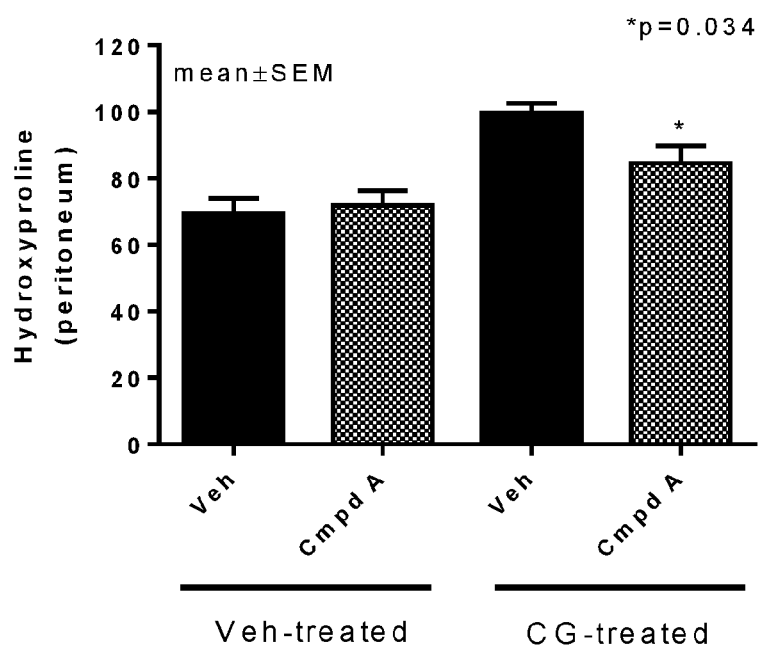
FIG. 3 provides hydroxyproline levels in mice peritoneum from vehicle or chlorhexidine gluconate injected mice treated with an autotaxin inhibitor. Cmpd A attenuates peritoneal fibrosis when dosed prophylactically in a mouse chlorhexidine gluconate model.
Figure 4:
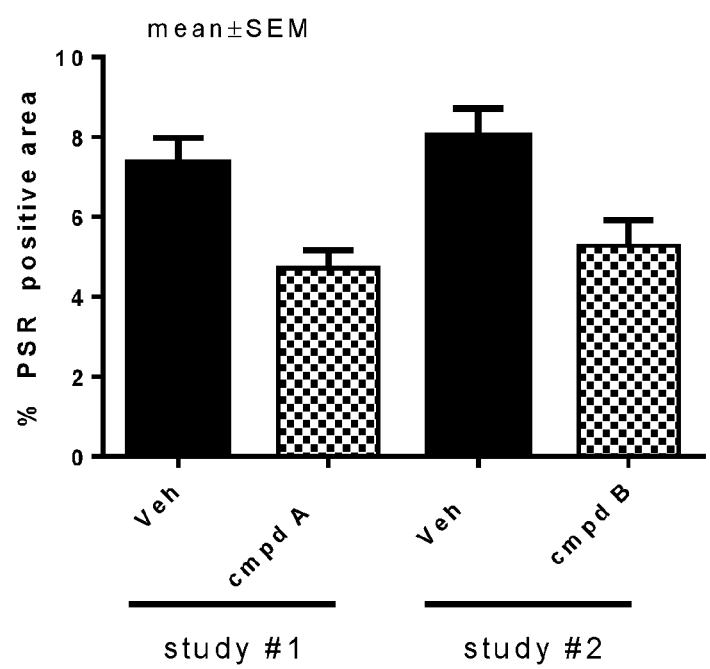
FIG. 4 provides percent PSR positive area in the livers from CDAA/HFD fed mice treated therapeutically with vehicle or autotaxin inhibitors. Cmpd A and cmpd B attenuate hepatic fibrosis when dosed therapeutically in a mouse CDAA/HFD model.

FIG. 3 shows the effect of compound A on hydroxyproline content in the peritoneum of mice at Day 21 after prophylactic dosing.

Compound A dosed at 60 mpk twice daily reduced hydroxyproline content in the peritoneum of mice by approximately 50%.

Example 29: Mouse Dextran Sodium Sulfate (DSS)-Induced Chronic Colitis Model

Female C57BL/6 mice are subjected to 3 cycles of 2% DSS in drinking water for 6 days, followed by drinking water without DSS for 15 days, for a total duration of 64 days. Autotaxin inhibitors are dosed at 30, 60 or 100 mpk PO once or twice daily from Day 0 to 63. For a positive control, Cyclosporin A (CsA) is dosed at 25 mpk on Days 1-7, 22-28, and 43-49. Mouse body weight, stool consistency, bleeding and overall Disease Activity Index (DAI) is recorded daily. After 64 days, mouse colons are removed and their length and weights recorded. Colonic sections are stained with hematoxylin and eosin stain (H&E stain) and scored based on inflammatory cell infiltration and tissue damage. Colonic sections are also stained with trichrome and scored for fibrosis.

In this colitis model, mice treated with compound A or compound B showed a reduction in colon weight/colon length/body weight ratio as compared to mice treated with vehicle. For example, the ratio of (colon weight/colon length/body weight)*100 in mice induced with colitis was at least about 20% lower in mice treated with compound A or compound B as compared to mice treated with vehicle. Mice treated with compound B showed a significant increase in colon length as compared to mice treated with vehicle. For example, the colon length in mice treated with compound B was at least about 30% longer than mice treated with vehicle.

Example 30: Rat Dinitrobenzene Sulfonic Acid (DNBS)-Induced Acute Colitis Model

Male Wistar rats weighing 150-160 g are intracolonically administered 0.5 ml of 50 mg/ml DNBS in 30% ethanol on Day 1 or vehicle control. Autotaxin inhibitors are dosed at 5 mpk in 0.5% MC once daily from Day 0 to Day 6. Sulfasalazine is dosed at 300 mpk in 0.5% CMC-Na from Day 1 to Day 7. The rats are monitored for body weight and stool consistency daily. At study termination, colon length, colon weight, ulcer area and Masson's trichrome staining are assessed. In one DNBS-induced colitis model, compound A and compound B had a positive effect on colitis by reducing ulcer area.

In this acute colitis model, compound A and compound B had no significant effect on body weight loss or stool consistency. Compound A and compound B reduced ulcer area and colon weight similiar to sulfasalazine. For example, treatment with compound A or compound B resulted in a 30 to 60% reduction in ulcer area as compared to mice treated with vehicle.

Example 31: Effects of Autotaxin Inhibitors on Glucose Tolerance in Mice Fed a High Fat Diet C57B16/J male mice are fed a normal diet until 6-10 weeks of age. Mice are then fed either a normal diet (ND)

or high-fat diet (HFD) (20% protein, 35% carbohydrate, 45% fat; Harlan Laboratories) for 8-10 weeks. For determination of blood glucose, mice are administered test compound orally in 0.5% methocel once or twice daily for several days prior to the glucose challenge. On the day of the glucose tolerance test (GTT) mice are fasted for 6-8 hours and a last dose of test compound administered orally 1-3 hours before the intraperitoneal (i.p.) injection of 1 g/kg D-glucose (Sigma). Blood from the tail vein is sampled before the glucose load (baseline glucose) and every 15-30 min over the next 120 min after the glucose challenge to monitor blood glucose concentration. Blood glucose is quantified using a glucose meter (Accu-Chek, Roche Diagnostics or AlphaTRAK, Abbott Animal Health) and plotted vs. time. Total blood glucose area under the curve (AUC) after the i.p. glucose challenge is calculated from the time plot using GraphPad Prism6.

Administration of Compound B (15 mg/kg) twice daily for two days prior to sampling and once on the day of sampling decreased baseline glucose and total blood glucose AUC.

Administration of Compound A (30 mg/kg) once daily for 5 days prior to sampling decreased baseline glucose.

Example 32: Mouse Air Pouch Assay

LPA and autotaxin activity are induced by carrageenan injection into a mouse air pouch. A mouse air pouch assay is utilized to determine pharmacodynamic activity of autotaxin inhibitors in reducing carrageenan-induced autotaxin activity and LPA biosynthesis. An air pouch is formed in mice by instilling 5 mL of 0.2 μm filtered air into the subcutaneous space in the scapular region on Day 1. On Day 3, 3 mL of air is instilled into the pouch and on Day 6, another 3 ml air is instilled into the pouch. On Day 7, test compounds are administered by oral gavage. At the appropriate time (0-24 hr) after compound administration, carrageenan dissolved in sterile saline is injected into the air pouch. Two hours following carrageenan challenge, mice are sacrificed and blood obtained via cardiac puncture. A 0.5-1 mL bolus of ice-cold phosphate buffered saline solution is instilled into the air pouch and after 20 seconds of gentle massaging, the pouch is opened and the fluid removed. An aliquot of the air pouch fluid is analyzed for LPA concentrations by LC-MS as described in the Human Whole Blood Autotaxin Assay (Example 10). A separate aliquot of the air pouch fluid is taken, centrifuged (800×g, 10 min) and assayed for ATX activity using a TOOS method or for drug concentrations by LCMS. Plasma prepared from blood is assayed for drug concentrations by LCMS.

Example 33: Spontaneous Metastasis Mouse Model

A syngeneic mouse model is used to test efficacy of compounds in inhibiting tumor metastases. 4T1 cells are in injected into the #7 mammary fat pad of female Balb/c mice while the mice are anesthetized. The primary tumors are measured by caliper twice weekly until they are resected under isofluorane anesthesia (between days 10-14). Test compound is administered orally daily at various times after the injection of the 4T1 cells. At 8-11 weeks after the 4T1 injection, lymph nodes, lungs, liver and any other organs suspected of harboring metastases are collected for histological analysis.

Example 34: Lung Metastases Model

An experimental lung metastasis model is used to test efficacy of compounds in reducing the number of metastases of injected B16-F 10 mouse melanoma cells to the lung. Briefly, female C57BL/6J mice, female (BALB/cByJ× C57BL/6J)Fi, mice (CByB6Fi/J), athymic nude female and male CByB6Fi/J mice (nu/nu), and control littermates (nu/nu) are used at ages 7-18 weeks, when they weighed between 18 and 28 g. A single-cell suspension of B16F10 cells, harvested in log phase (approx. 5-10×10$^4$ cells) in 0.2 mL of Hanks' balanced salt solution are injected intravenously into the lateral tail vein of the mice. Test compound or vehicle is delivered daily. After 21 days, the mice are sacrificed, and the lungs are removed. Lungs are fixed in 10% buffered formalin overnight and weighed, and tumor colonies at the surface are scored with the aid of a dissecting microscope.

Example 35: Clinical Trial for Liver Fibrosis

A non-limiting example of a liver fibrosis clinical trial in humans is described below.

Purpose:

The purposes of this study are to assess the efficacy of an autotaxin inhibitor, or a pharmaceutically acceptable salt thereof, as single agent or in combination, in the treatment of patients with liver fibrosis, collect information on any side effects the compound may cause as single agent or in combination, and evaluate the pharmacokinetic properties of the compound as single agent or in combination.

Intervention:

Patients are administered 1-100 mg/kg of an autotaxin inhibitor, or a pharmaceutically acceptable salt thereof, per day as single agent or in combination.

Detailed Description:

Patients will be given an autotaxin inhibitor, or a pharmaceutically acceptable salt thereof, orally once or twice a day as single agent or in combination. Prior to each dosing cycle, a physical exam, blood work and assessment of any side effects will be performed.

Primary Outcome Measures:

Liver enzymes (ALT, AST, ALP), liver biopsy

Secondary Outcome Measures:

Pharmacodynamic markers may include: Tissue PD markers through mRNA expression, autotaxin, LOXL2, LOX, Other LOXL proteins, aSMA, Collagen 1A1, NF-κB1, Caspase 1, SMAD, and NOD; Serum and plasma PD markers include: AST-to-platelet ratio index (APRI), autotaxin activity, LOXL2, Osteopontin, Hyaluronic Acid, CXCL 9, 10 and 11, MMP1, MMP3, MMP9, TIMP1, CD4OL, TGF-β1, ET-1, VEGF, GAL3, IL-6/IL-8/TNFα/IFNγ, α2-macroglobulin, Apolipoprotein A1, PINP, PIIINP, PVCP-1230, DGF; Assessing the effects of chronic dosing on liver structure and fibrotic markers; incidence of adverse events resulting from the administration of multiple doses of compound.

Eligibility:

Male and female subjects that are 18 to 60 years old.

Inclusion Criteria:

Stage 1-3 fibrosis by Metavir score on a liver biopsy; Body mass index <36 kg/m2.

Exclusion Criteria:

Any evidence of hepatic decompensation past or present; subjects currently abusing amphetamines, cocaine, opiates, or alcohol; clinically significant cardiac disease; history of cancer, other than non-melanomatous skin cancer, within 5 years prior to screening; systemic fungal, bacterial, viral, or other infection that is not controlled; use of systemic immunosuppressants within 28 days of the Pre-treatment Phase; use of approved therapy for hepatitis C or hepatitis B virus within 28 days of the Pre-treatment Phase; pregnant or lactating; history of bleeding diathesis within the last 6 months of study Day 1.

Example 36: Clinical Trial for Fatty Liver Disease/Steatosis (NAFLD, NASH)

A non-limiting example of a fatty liver disease/steatosis clinical trial in humans is described below.

Purpose:

The purposes of this study are to assess the efficacy of an autotaxin inhibitor, or a pharmaceutically acceptable salt thereof, as single agent or in combination, in the treatment of patients with hepatocellular carcinoma, collect information on any side effects the compound may cause as single agent or in combination, and evaluate the pharmacokinetic properties of the compound as single agent or in combination.

Intervention:

Patients are administered 0.1-100 mg/kg of an autotaxin inhibitor, or a pharmaceutically acceptable salt thereof, per day as single agent or in combination.

Detailed Description:

Patients will be given an autotaxin inhibitor, or a pharmaceutically acceptable salt thereof, orally once or twice a day as single agent or in combination. Prior to each dosing cycle, a physical exam, blood work and assessment of any side effects will be performed.

Eligibility:

Male and female subjects that are 21 to 80 years old.

Inclusion Criteria:

Patients with clinically confirmed diagnosis of non-alcohol fatty liver disease or non-alcohol steatohepatitis; histologic evidence of definite or probable nonalcoholic steatohepatitis (NASH) based upon a liver biopsy obtained no more than 90 days prior to randomization and a nonalcoholic fatty liver disease activity score (NAS) of 4 or greater.

Exclusion Criteria:

Current or history of significant alcohol consumption, use of drugs historically associated with nonalcoholic fatty liver disease (NAFLD) (amiodarone, methotrexate, systemic glucocorticoids, tetracyclines, tamoxifen, estrogens at doses greater than those used for hormone replacement, anabolic steroids, valproic acid, and other known hepatotoxins) for more than 2 weeks in the year prior to randomization, prior or planned (during the study period) bariatric surgery (e.g., gastroplasty, roux-en-Y gastric bypass), uncontrolled diabetes defined as Hemoglobin A1c 9.5% or higher within 60 days prior to enrollment, presence of cirrhosis on liver biopsy, platelet count below 100,000/mm3; Clinical evidence of hepatic decompensation as defined by the presence of any of the following abnormalities: serum albumin less than 3.2 grams/deciliter (g/dL), INR (international normalized ratio) greater than 1.3, direct bilirubin greater than 1.3 milligrams per deciliter (mg/dL), history of esophageal varices, ascites or hepatic encephalopathy; Evidence of other forms of chronic liver disease: hepatitis B as defined by presence of hepatitis B surface antigen (HBsAg), hepatitis C as defined by presence of hepatitis C virus (HCV) ribonucleic acid (RNA) or positive hepatitis C antibody (anti-HCV), evidence of ongoing autoimmune liver disease as defined by compatible liver histology, primary biliary cirrhosis, primary sclerosing cholangitis, Wilson's disease, Alpha-1-antitrypsin(A1AT) deficiency, history of hemochromatosis or iron overload, drug-induced liver disease as defined on the basis of typical exposure and history, known bile duct obstruction, suspected or proven liver cancer, any other type of liver disease other than nonalcoholic steatohepatitis (NASH); serum alanine aminotransferase (ALT) greater than 300 units per liter (U/L); serum creatinine of 2.0 mg/dL or greater; use of ursodeoxycholic acid (Ursodiol, Urso) within 90 days prior to enrollment; inability to safely obtain a liver biopsy, history of biliary diversion, known positivity for Human Immunodeficiency Virus (HIV) infection; pregnancy, planned pregnancy, potential for pregnancy and unwillingness to use effective birth control during the trial, breast feeding Primary Outcome Measures:

liver function tests, liver biopsy, NAS score

Secondary Outcome Measures:

fibrotic biomarkers, liver imaging (ultrasound, MRI), insulin resistance as measure by HOMA-IR, lipid panel.

Example 37: Clinical Trial for Ulcerative Colitis

A non-limiting example of an ulcerative colitis clinical trial in humans is described below.

Purpose:

The purposes of this study are to assess the efficacy of an autotaxin inhibitor, or a pharmaceutically acceptable salt thereof, as single agent or in combination, in the treatment of patients with ulcerative colitis, collect information on any side effects the compound may cause as single agent or in combination, and evaluate the pharmacokinetic properties of the compound as single agent or in combination.

Intervention:

Patients are administered 0.1-100 mg/kg of an autotaxin inhibitor, or a pharmaceutically acceptable salt thereof, per day as single agent or in combination.

Detailed Description:

Patients will be given an autotaxin inhibitor, or a pharmaceutically acceptable salt thereof, orally once or twice a day as single agent or in combination. Prior to each dosing cycle, a physical exam, blood work and assessment of any side effects will be performed.

Primary Outcome Measures:

Improvement in Mayo Score or other suitable disease activity index for colitis and/or IBD Secondary Outcome Measures:

Improvement in histological evaluation by flexible sigmoidoscopy and biopsy; bleeding score; quality of life instruments (IBDQ, SF36); assessing the effects of chronic dosing on inflammation and fibrotic markers; overall safety assessments Eligibility:

Male and female subjects that are 18 to 65 years old.

Inclusion Criteria:

Confirmed diagnosis of colitis for at least 3 months.

Exclusion Criteria:

Any evidence of hepatic decompensation past or present; Crohn's disease; patients hospitalized or exhibiting signs of toxicity; history or colorectal cancer or colorectal dysplasia; ALP, ALT, AST or bilirubin >1.5× normal; pregnant or lactating.

Example 38: Clinical Trial for Cholestatic Pruritus

A non-limiting example of a cholestatic pruritus clinical trial in humans is described below.

Purpose:

The purposes of this study are to assess the efficacy of an autotaxin inhibitor, or a pharmaceutically acceptable salt thereof in the treatment of patients with cholestatic pruritus, collect information on any side effects the compound may cause and evaluate the pharmacokinetic properties of the compound as single agent or in combination.

Intervention:

Patients are administered 1-100 mg/kg of an autotaxin inhibitor, or a pharmaceutically acceptable salt thereof, per day.

Detailed Description:

Patients will be given an autotaxin inhibitor, or a pharmaceutically acceptable salt thereof, orally once or twice a day. Prior to each dosing cycle, a physical exam, blood work and assessment of any side effects will be performed.

Eligibility:

Male and female subjects that are 21 to 80 years old.

Inclusion Criteria:

Patients with pruritus as a result of a cholestatic disorder.

Exclusion Criteria:

Use of cholestyramine; pregnancy; malignancy/life expectancy <6 months.

Primary Outcome Measures:

Normalization of liver enzymes (ALT, AST, ALP), Reduction of pruritus according to visual analogue scores.

Secondary Outcome Measures:

Improvement in quality of life scores; reduction in pruritus score/scratch lesions.

Example 39: Clinical Trial for Pulmonary Fibrosis

A non-limiting example of a pulmonary fibrosis clinical trial in humans is described below.

Purpose:

The purposes of this study are to assess the efficacy of an autotaxin inhibitor, or a pharmaceutically acceptable salt thereof, as single agent or in combination, in the treatment of patients with pulmonary fibrosis, collect information on any side effects the compound may cause as single agent or in combination, and evaluate the pharmacokinetic properties of the compound as single agent or in combination.

Intervention:

Patients are administered 1-100 mg/kg of an autotaxin inhibitor, or a pharmaceutically acceptable salt thereof, per day as single agent or in combination.

Detailed Description:

Patients will be given an autotaxin inhibitor, or a pharmaceutically acceptable salt thereof, orally once or twice a day as single agent or in combination. Prior to each dosing cycle, a physical exam, blood work and assessment of any side effects will be performed.

Primary Outcome Measures:

Progression-free survival, defined as free of death or a decrease from baseline in the FVC of at least 10%.

Secondary Outcome Measures:

Number of Acute Exacerbations of IPF; health related quality of life; $PO_2$ at rest and at exercise from baseline; $P(A-a)O_2$ at rest and at exercise from baseline; Predicted FEV1 from baseline; forced expiratory volume in one second (FEV1) to FVC from baseline; plethysmographic lung volumes from baseline; diffusion capacity for carbon monoxide (DLco) from baseline; Six-Minute Walk test, from baseline: resting and 6 minute SpO2, presence or absence of desaturation to 88% or lower at the end of the six minute walk, walked distance; Pre and post modified Borg dyspnea scores; scoring of extent of lung fibrosis on HRCT, according to two independent chest radiologists, form baseline; number and severity of adverse effects.

Eligibility:

Male and female subjects that are 40 years to 80 years.

Inclusion Criteria:

Clinical symptoms of IPF for at least 3 months; forced vital capacity (FVC) between 50 to 90% of the predicted value; DLco at least 35% of the predicted value; PaO2 >55 mm Hg while breathing ambient air at rest; High-resolution computed tomography (HRCT) showing definite or probable criteria of IPF.

Exclusion Criteria:

Clinically significant exposure to known fibrogenic agents (birds, molds, asbestos, radiation and drugs known to cause pulmonary fibrosis (amiodarone, nitrofurantoin, bleomicin, etc)); history of neurofibromatosis, Hermansky-Pudlak syndrome, metabolic storage disorders, etc.; history of fever, weight loss, myalgias, arthralgias, skin rash, arthritis; active infection within one week before enrollment; alternative cause of interstitial lung disease; ratio of the forced expiratory volume in one second (VEF1) to FVC of less than 0.6 after the use of a bronchodilator; residual volume more than 120% of the predicted value (when available); more than 20% of lymphocytes or eosinophils in bronchoalveolar lavage (BAL) (when available); granulomas, infection or malignancy in the transbronchial or surgical biopsy (when available); previous therapy with azathioprine, prednisolone (>0.5 mg/kg/day or more for at least 3 months), cyclophosphamide or novel biotech drugs; unstable cardiovascular or neurologic disease; uncontrolled diabetes; pregnancy; lactation; likelihood of death, as predicted by the investigator, within the next year; white cell blood count <4000/mm3; platelet count <100000/mm3; Hematocrit <30% or >59%; liver enzymes more than 3 times the upper limit of the normal range; creatinine level >1.5 mg/dL; albumin level <3 g/dL; refusal to sign informed consent by patient or guardian.

Example 40: Clinical Trial for Pancreatic Cancer

A non-limiting example of a pancreatic cancer clinical trial in humans is described below.

Purpose:

The purposes of this study are to assess the efficacy of an autotaxin inhibitor, or a pharmaceutically acceptable salt thereof, as single agent or in combination, in the treatment of patients with pancreatic cancer, collect information on any side effects the compound may cause as single agent or in combination, and evaluate the pharmacokinetic properties of the compound as single agent or in combination.

Intervention:

Patients are administered 1-100 mg/kg of an autotaxin inhibitor, or a pharmaceutically acceptable salt thereof, per day as single agent or in combination.

Detailed Description:

Patients will be given an autotaxin inhibitor, or a pharmaceutically acceptable salt thereof, orally once or twice a day as single agent or in combination. Prior to each dosing cycle, a physical exam, blood work and assessment of any side effects will be performed.

Eligibility:

Male and female subjects that are 21 to 80 years old with advanced pancreatic cancer.

Inclusion Criteria:

Radiographic or clinical evidence of measurable advanced pancreatic carcinoma (Stage II, II, IV). Subjects must have measurable disease at least 2 cm in diameter. ECOG performance status of 0 or 1

Exclusion Criteria:

Prior history of malignancy (except basal cell or squamous cell carcinoma or carcinoma in situ of the breast) unless the subject has been free of disease for > or = to 1 year. Moderate or severe cardiac disease; Active infection; Not pregnant or nursing; Negative pregnancy test; Fertile patients must use effective contraception during and for ≥3 months after completion of study treatment; Able to swallow oral medication; No other malignancy within the past 5 years except for in situ cancers or basal cell or squamous cell carcinoma of the skin; No hypersensitivity or intolerance to statins; no other non-malignant systemic disease that would preclude rosuvastatin administration or prolonged follow-up.

Primary Outcome Measures:

Progression free survival, overall survival, worsening of pain, onset of pain

Secondary Outcome Measures:

tumor size/response (RECIST)

Example 41: Clinical Trial for Hepatocellular Carcinoma (HCC)

A non-limiting example of a hepatocellular carcinoma clinical trial in humans is described below.

Purpose:

The purposes of this study are to assess the efficacy of an autotaxin inhibitor, or a pharmaceutically acceptable salt thereof, as single agent or in combination, in the treatment of patients with hepatocellular carcinoma, collect information on any side effects the compound may cause as single agent or in combination, and evaluate the pharmacokinetic properties of the compound as single agent or in combination.

Intervention:

Patients are administered 1-100 mg/kg of an autotaxin inhibitor, or a pharmaceutically acceptable salt thereof, per day as single agent or in combination.

Detailed Description:

Patients will be given an autotaxin inhibitor, or a pharmaceutically acceptable salt thereof, orally once or twice a day as single agent or in combination. Prior to each dosing cycle, a physical exam, blood work and assessment of any side effects will be performed.

Eligibility:

Male and female subjects that are 21 to 80 years old.

Inclusion Criteria:

Patients with histopathologically or clinically confirmed diagnosis of hepatocellular carcinoma; unresponsive to standard therapy or for whom standard therapy is intolerable, or for whom there is no appropriate therapy; ECOG performance status score of 0-2.

Exclusion Criteria:

Patients with a primary malignant tumor; history of liver transplant; brain metastases; psychiatric disorder that might cause difficulty in obtaining informed consent or in conducting the trial; Not pregnant or nursing; Fertile patients must use effective contraception during and for ≥3 months after completion of study treatment; No other malignancy within the past 5 years except for in situ cancers or basal cell or squamous cell carcinoma of the skin; No hypersensitivity or intolerance to statins; no other non-malignant systemic disease that would preclude rosuvastatin administration or prolonged follow-up.

Primary Outcome Measures:

time to progression, progression free survival, overall response (RECIST)

Secondary Outcome Measures:

liver function tests, tumor biomarkers

Example 42: Clinical Trial for Multiple Sclerosis

A non-limiting example of a multiple sclerosis clinical trial in humans is described below.

Purpose:

The purposes of this study are to assess the efficacy of an autotaxin inhibitor, or a pharmaceutically acceptable salt thereof, as single agent or in combination, in the treatment of patients with multiple sclerosis, collect information on any side effects the compound may cause as single agent or in combination, and evaluate the pharmacokinetic properties of the compound as single agent or in combination.

Intervention:

Patients are administered 1-100 mg/kg of an autotaxin inhibitor, or a pharmaceutically acceptable salt thereof, per day as single agent or in combination.

Detailed Description:

Patients will be given an autotaxin inhibitor, or a pharmaceutically acceptable salt thereof, orally once or twice a day as single agent or in combination. Prior to each dosing cycle, a physical exam, blood work and assessment of any side effects will be performed.

Primary Outcome Measures:

Multiple Sclerosis Functional Composite (MSFC) score, or other suitable for assessing response and relapse of symptoms in MS, Secondary Outcome Measures:

Total number of new GdE lesions, assessed on brain MRIs improvement in one or more signs or symptoms of multiple sclerosis as measured byFunctional Systems Scores (FSS) and Expanded Disability Status Scale (EDSS); Multiple Sclerosis Quality of Life 54 items (MSQOL-54); Timed 25-foot walk; Nine-hole peg test Eligibility:

Male and female subjects that are 18 to 65 years old.

Inclusion Criteria:

Confirmed diagnosis of multiple sclerosis.

Exclusion Criteria:

Pregnant or lactating.

The examples and embodiments described herein are for illustrative purposes only and various modifications or changes suggested to persons skilled in the art are to be included within the spirit and purview of this application and scope of the appended claims.

What is claimed is:

1. A method for treating pruritis, in a mammal, comprising administering to the mammal an autotaxin inhibitor with the following structure:

Compound A
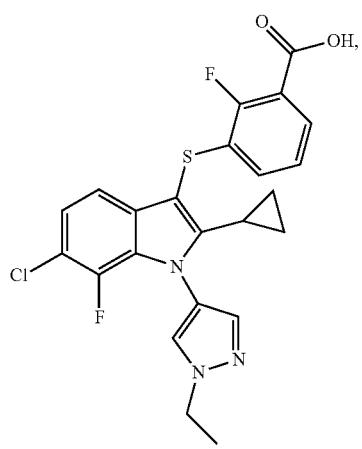
Compound B
Compound E
Compound F
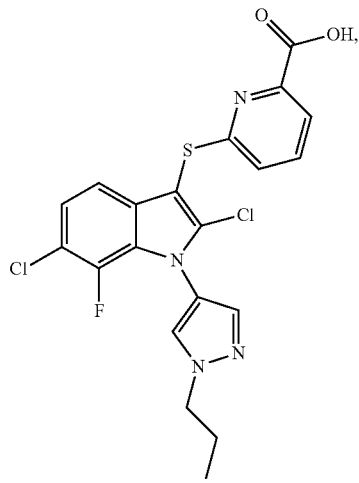
Compound G
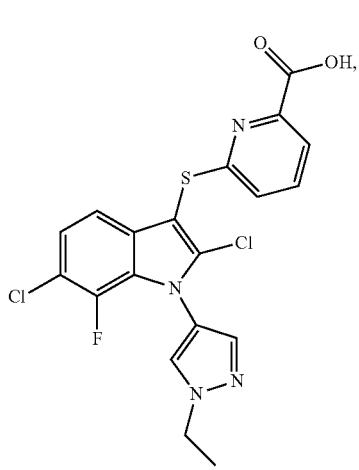
Compound H
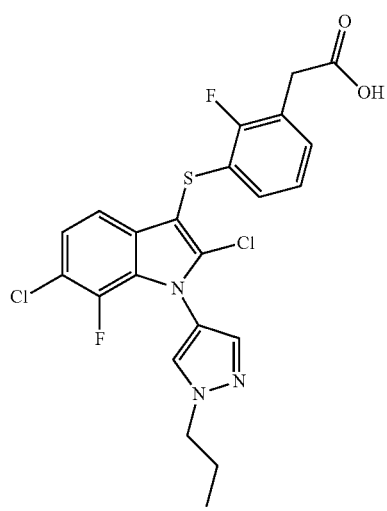
or -continued Compound I

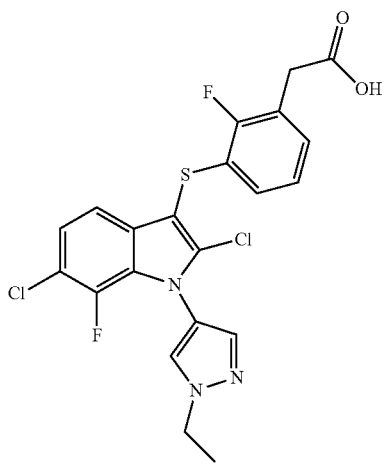 [SMILES: CCn1cc(-n2c(Cl)c(Sc3cccc(CC(=O)O)c3F)c3ccc(Cl)c(F)c32)cn1]

or a pharmaceutical acceptable salt, or solvate thereof.

2. The method of claim 1, wherein Compound A, Compound B, Compound E, Compound F, Compound G, Compound H, Compound I, is administered in the form of a pharmaceutically acceptable salt.

3. The method of claim 2, wherein Compound A, Compound B, Compound E, Compound F, Compound G, Compound H, Compound I, is administered in the form of a sodium salt.

4. The method of claim 1, wherein the autotaxin inhibitor is topically administered, orally administered, or parenterally administered to the mammal.

5. The method of claim 1, wherein the autotaxin inhibitor is systemically administered to the mammal.

6. The method of claim 1, wherein the autotaxin inhibitor is orally administered to the mammal.

7. The method of claim 1, wherein the pruritus is associated with dermatitis herpetiformis, dermatomyositis, pemphigoid, Sjögren's syndrome, Darier's disease, Hailey-Hailey disease, Ichthyoses, Sjögren-Larsson syndrome, dermatophytosis, folliculitis, impetigo and other bacterial infections, insect bites, pediculosis, scabies, viral infection, asteatosis, atopic eczema, contact dermatitis, drug reaction, lichen planus, lichen simplex chronicus, mastocytosis (urticaria pigmentosa), miliaria, psoriasis, scar(s), urticaria, cutaneous T-cell lymphoma or mycosis fungoides, cutaneous B-cell lymphoma, leukemia cutis, pemphigoid gestationis, polymorphic eruption of pregnancy or prurigo gestationis.

8. The method of claim 1, wherein the pruritus is cholestatic pruritis.

9. The method of claim 1, furthering comprising administering at least one additional therapy to the mammal.

* * * * *